United States Patent [19]
Allington et al.

[11] Patent Number: 6,149,814
[45] Date of Patent: Nov. 21, 2000

[54] APPARATUS AND METHOD FOR SUPERCRITICAL FLUID EXTRACTION OR SUPERCRITICAL FLUID CHROMATOGRAPHY

[75] Inventors: Robert W. Allington; Henry LeRoy Walters; Daniel Gene Jameson, all of Lincoln, Nebr.; Yoossef Tehrani, Ashland, Md.

[73] Assignee: Isco, Inc., Lincoln, Nebr.

[21] Appl. No.: 09/074,254

[22] Filed: May 7, 1998

Related U.S. Application Data

[62] Division of application No. 08/804,682, Feb. 25, 1997, Pat. No. 5,750,027, which is a division of application No. 08/542,683, Oct. 13, 1995, Pat. No. 5,614,089, which is a continuation of application No. 08/096,919, Jul. 23, 1993, abandoned, which is a continuation-in-part of application No. 08/027,257, Mar. 5, 1993, Pat. No. 5,268,103, which is a continuation-in-part of application No. 07/908,458, Jul. 6, 1992, Pat. No. 5,198,197, which is a division of application No. 07/795,987, Nov. 22, 1991, Pat. No. 5,160,624, which is a continuation-in-part of application No. 07/553,119, Jul. 13, 1990, Pat. No. 5,094,753.

[51] Int. Cl.$^7$ ................................................ B01D 11/00
[52] U.S. Cl. ................................ 210/634; 210/656
[58] Field of Search .................................. 210/634, 635, 210/656, 659, 198.2, 511; 251/129.15, 331, 335.2; 422/256, 261, 285

[56] References Cited

U.S. PATENT DOCUMENTS

| | | | |
|---|---|---|---|
| 524,702 | 8/1894 | Browning | 251/155 |
| 2,507,851 | 5/1950 | Bryant et al. | 251/155 |
| 3,198,948 | 8/1965 | Olson | 250/106 |
| 3,257,561 | 6/1966 | Packard et al. | 250/106 |
| 3,872,723 | 3/1975 | Busch | 73/194 R |
| 4,032,445 | 6/1977 | Munk | 210/103 |
| 4,064,908 | 12/1977 | Loe | 137/614.17 |
| 4,217,931 | 8/1980 | Jaekel | 137/606 |

(List continued on next page.)

FOREIGN PATENT DOCUMENTS

| | | | |
|---|---|---|---|
| 1357078 | 6/1974 | Canada | 210/634 |
| 124686 | 10/1967 | Czechoslovakia | 210/634 |
| 0 212 999 A1 | 3/1987 | European Pat. Off. | 210/634 |
| 0 236 982 A2 | 9/1987 | European Pat. Off. | 210/634 |

(List continued on next page.)

OTHER PUBLICATIONS

Wright, B.W., et al., 1987, "Analytical Supercritical Fluid Extraction of Adsorbent Materials", Anal. Chem., 59:38–44.

Sugiyama, K., et al., 1985, "New Double–Stage Separation Analysis Method: Directly Coupled Laboratory–Scale Supercritical Fluid Extraction–Supercritical Chromatography, Monitored With A Multiwavelength Ultraviolent Detector", J. Chromatog., 332:107–116.

Hawthorne, S.B., et al., 1986, "Extraction and Recovery of Organic Pollutants from Environmental Solids and Tenax–GC Using Supercritical $CO_2$", J. Chromatog. Science, 24:258–264.

(List continued on next page.)

*Primary Examiner*—Ernest G. Therkorn
*Attorney, Agent, or Firm*—Vincent L. Carney

[57] ABSTRACT

A variable-orifice fluid restrictor for use with a supercritical extractor or chromatograph includes an inlet line for fluid at a pressure above its critical pressure, an extended tubular probe having an inner and an outer surface and a proximal and a distal end. The proximal end of the probe is disposed toward the inlet line. The distal end of the probe includes an adjustable orifice means adapted for metering the fluid and having first and second orifice members and an adjusting stem having first and second ends. The adjustable orifice means is adjacent to the outer surface of the probe and the orifice means is adjustable with the adjusting stem. The end of the adjusting stem is located at the distal end of the probe and is adapted for moving the first orifice member with respect to the second orifice member to control the adjustable orifice for varying the restriction of fluid passing through the adjustable orifice.

5 Claims, 23 Drawing Sheets

U.S. PATENT DOCUMENTS

| | | | |
|---|---|---|---|
| 4,225,290 | 9/1980 | Allington et al. | 417/18 |
| 4,265,860 | 5/1981 | Jennings et al. | 422/280 |
| 4,375,163 | 3/1983 | Yang | 210/198.2 |
| 4,438,370 | 3/1984 | Allington | 315/106 |
| 4,476,732 | 10/1984 | Yang | 73/863.73 |
| 4,477,266 | 10/1984 | Yang | 55/67 |
| 4,483,773 | 11/1984 | Yang | 210/656 |
| 4,564,145 | 1/1986 | Takada et al. | 239/585 |
| 4,597,943 | 7/1986 | Sugiyama et al. | 422/70 |
| 4,600,365 | 7/1986 | Riggenmann | 417/246 |
| 4,676,897 | 6/1987 | Kuze et al. | 210/198.2 |
| 4,705,459 | 11/1987 | Buisine et al. | 417/53 |
| 4,711,764 | 12/1987 | Good | 422/65 |
| 4,724,087 | 2/1988 | Perrut | 210/788 |
| 4,770,780 | 9/1988 | Moses | 210/634 |
| 4,790,236 | 12/1988 | Macdonald et al. | 92/129 |
| 4,814,089 | 3/1989 | Kumar | 210/659 |
| 4,820,129 | 4/1989 | Magnussen | 417/18 |
| 4,851,683 | 7/1989 | Yang | 250/339 |
| 4,871,453 | 10/1989 | Kumar | 210/198.2 |
| 4,892,654 | 1/1990 | Nickerson | 210/198.2 |
| 4,902,891 | 2/1990 | Vestal | 250/281 |
| 4,913,624 | 4/1990 | Seki | 417/2 |
| 4,915,591 | 4/1990 | Funke | 417/18 |
| 4,980,057 | 12/1990 | Dorn | 210/198.2 |
| 4,984,602 | 1/1991 | Saito et al. | 137/487.5 |
| 4,998,433 | 3/1991 | Stumpf et al. | 73/25.01 |
| 5,009,778 | 4/1991 | Nickerson | 210/659 |
| 5,013,443 | 5/1991 | Higashidate et al. | 210/634 |
| 5,031,448 | 7/1991 | Saito | 73/61.1 C |
| 5,075,017 | 12/1991 | Hossain et al. | 210/761 |
| 5,087,360 | 2/1992 | Wright et al. | 210/198.2 |
| 5,094,741 | 3/1992 | Frank et al. | 210/198.2 |
| 5,094,753 | 3/1992 | Allington et al. | 210/634 |
| 5,116,508 | 5/1992 | Kumar et al. | 210/639 |
| 5,133,859 | 7/1992 | Frank et al. | 210/198.2 |
| 5,147,538 | 9/1992 | Wright et al. | 210/198.2 |
| 5,151,178 | 9/1992 | Nickerson et al. | 210/198.2 |
| 5,160,624 | 11/1992 | Clay et al. | 210/198.2 |
| 5,164,693 | 11/1992 | Yokoyama et al. | 335/14 |
| 5,173,188 | 12/1992 | Winter et al. | 210/198.2 |
| 5,178,767 | 1/1993 | Nickerson et al. | 210/656 |
| 5,180,487 | 1/1993 | Saito et al. | 210/198.2 |
| 5,193,991 | 3/1993 | Koebler et al. | 417/571 |
| 5,198,197 | 3/1993 | Clay et al. | 422/256 |
| 5,205,987 | 4/1993 | Ashraf-Khorassani et al. | 422/83 |
| 5,240,603 | 8/1993 | Frank et al. | 210/198.2 |
| 5,241,998 | 9/1993 | Ashraf-Khorassani | 141/67 |
| 5,253,981 | 10/1993 | Yang | 417/3 |
| 5,268,103 | 12/1993 | Jameson et al. | 210/634 |
| 5,271,903 | 12/1993 | Durst et al. | 422/101 |
| 5,316,262 | 5/1994 | Koebler | 251/8 |
| 5,322,626 | 6/1994 | Frank et al. | 210/634 |
| 5,363,886 | 11/1994 | Ashraf-Khorassani | 141/5 |
| 5,372,716 | 12/1994 | Levy et al. | 210/198.2 |
| 5,379,790 | 1/1995 | Bruce et al. | 137/1 |
| 5,453,198 | 9/1995 | Ashruf-Khorassani et al. | 210/198.2 |
| 5,458,783 | 10/1995 | Levy et al. | 210/659 |

FOREIGN PATENT DOCUMENTS

| | | | |
|---|---|---|---|
| 275933A2 | 7/1988 | European Pat. Off. | 210/634 |
| 416326A2 | 3/1991 | European Pat. Off. | 210/634 |
| 450182A2 | 10/1991 | European Pat. Off. | 210/634 |
| 458125A2 | 11/1991 | European Pat. Off. | 210/634 |
| 466 291 A3 | 1/1992 | European Pat. Off. | 210/634 |
| 0 561 114 A1 | 9/1993 | European Pat. Off. | 210/634 |
| 558172A2 | 9/1993 | European Pat. Off. | 210/634 |
| 595 443 A1 | 5/1994 | European Pat. Off. | 210/634 |
| 0 672 831 A2 | 9/1995 | European Pat. Off. | 210/634 |
| 40 02 161 A1 | 8/1991 | Germany | 210/634 |
| 41424 | 3/1907 | Hungary | 210/634 |
| 58-9317 | 2/1983 | Japan | 210/634 |
| 58-38115 | 5/1983 | Japan | 210/634 |
| 63-56425 | 3/1988 | Japan | 210/634 |
| 64-44847 | 2/1989 | Japan | 210/634 |
| 2-8039 | 11/1990 | Japan | 210/634 |
| 3-26531 | 5/1991 | Japan | 210/634 |
| 3-251435 | 8/1991 | Japan | 210/634 |
| 2 348 572 | 9/1973 | Netherlands | 210/634 |
| 463644 | 3/1975 | Russian Federation | 210/634 |
| 1552201 | 9/1979 | United Kingdom | 210/634 |
| 2 254 383 | 10/1992 | United Kingdom | 210/634 |
| WO82/01578 | 5/1982 | WIPO | 210/634 |
| WO 85/04816 | 11/1985 | WIPO | 210/634 |
| 438 184 A1 | 1/1988 | WIPO | 210/634 |
| WO 92/05851 | 4/1992 | WIPO | 210/634 |
| WO92/06058 | 4/1992 | WIPO | 210/634 |
| WO 94 08683 A1 | 4/1994 | WIPO | 210/634 |
| WO 94/20190 | 9/1994 | WIPO | 210/634 |
| WO 95/03106 | 2/1995 | WIPO | 210/634 |

OTHER PUBLICATIONS

Hawthorne, S.B., et al., 1987, "Extraction and Recovery of Polycyclic Aromatic Hydrocarbons from Environmental Solids Using Supercritical Fluids", Anal. Chem., 59:1705–1708.

Schantz, M.M., et al., 1986, "Supercritical Fluid Extraction Procedure for the Removal of Trace Organic Species from Solid Samples", J. Chromatogr., 363:397–401.

Wright, B.W., et al., 1989, "Supercritical Fluid Extraction of Coal Tar Contaminated Soil Samples", Energy & Fuels, 3:474–480.

Lee, M.L., et al., 1979, "Retention Indices for Programmed–Temperature Capillary–Column Gas Chromatography of Polycyclic Aromatic Hydrocarbons", Anal. Chem., 51(6):768–774.

Vassilaros, D.L., et al., 1982, "Linear Retention Index System For Polycyclic Aromatic Compounds", J. Chromatogr., 252:1–20.

Czubryt, J.J., et al., 1970, "Solubility Phenomna in Dense Carbon Dioxide Gas in the Range 270–1900 Atmospheres", J. Phys. Chem., 74(24):4260–4266.

Wise, S.A., et al., 1988, "Determination of Polycyclic Aromatic Hydrocarbons in a Coal Tar Standard Reference Material", Anal. Chem., 60:887–894.

Villaume, J.F., 1984, "Coal Tar Wastes: Their Environmental Fate and Effects", *Hazardous and Toxic Wastes: Technology, Management, and Health Effects,* Chapter 25, S.K. Majumdar and E.W. Miller, Eds., pp. 362–375.

Maxwell, R.J., et al., 1992, "Improved SFE Recovery of Trace Analytes from Liver Using an Intergral Micrometering Valve–SPE Column Holder Assembly", J. High Resolution Chromatogr., 15:807–811.

Levy, J.M., et al., 1990, "Qualitative Supercritical Fluid Extraction Coupled to Capillary Gas Chromatography", J. High Resolution Chromatogr., 13:418–421.

Levy, J.M., et al., 1991, "The Use of Alternative Fluids in On–Line Supercritical Fluid Extraction–Capillary Gas Chromatography", J. High Resolution Chromatog., 14:661–668.

Wright, B.W., et al., 1992, "Evaluation of a Field–Portable Supercritical Fluid Extraction Apparatus for Rapid Characterization of Contaminated Soils", *Waste Testing and Quality Assurance: Third Volume,* D. Friedman, Eds., pp. 3–14.

Richter, B.E., 1985, "Modified Flame Ionization Detector for the Analysis of Large Molecular Weight Polar Compounds by Capillary Supercritical Fluid Chromatography", J. High Resolution Chromatogr. & Chromatogr. Communications, 8:297–300.

Daimon, H., et al., 1991, "Directly Coupled Supercritical–Fluid Extraction/Capillary Supercritical–Fluid Chromatography of Polymer Additives", Chromatographia, 32:549–554.

Levy, J.M., et al., 1989, "Quantitative Supercritical Fluid Extraction Coupled to Capillary Gas Chromatography", Chromatographia, 28:613–616.

Nielen, M.W.F., et al., 1989, "On–line System for Supercritical Fluid Extraction and Capillary Gas Chromatography with Electron–Capture Detection", J. Chromatog., 474:388–395.

Raynor, M.W., et al., 1988, "Supercritical Fluid Extraction/ Capillary Supercritical Fluid Chromatography/Fourier Transform Infrared Microspectrometry of Polycyclic Aromatic Compounds in a Coal Tar Pitch", J. High Resolution Chromatog. & Chromatog. Communications, 11:766–775.

Hawthorne, S.B., et al., 1989, "Coupled SFE–GC: A Rapid and Simple Technique for Extracting, Identifying, and Quantitating Organic Analytes from Solids and Sorbent Resins", J. Chromatog. Science, 27:347–354.

Berger, T.A., et al., 1989, "Linear Velocity Control in Capillary Supercritical Fluid Chromatography by Restrictor Temperature Programming", J. Chromatog., 465:157–167.

Lipsky, S.R., et al., 1986, "High Temperature Gas Chromatography: The Development of New Aluminum Clad Flexible Fused Silica Glass Capillary Columns Coated with Thermostable Nonpolar Phases: Part 1", J. High Resolution Chromatog. & Chromatog. Communications, 9:376–382.

Green, S., et al., 1988, "Simple Restrictors for Capillary Column Supercritical Fluid Chromatography", J. High Resolution Chromatog. & Chromatog. Communications, 11:414–415.

Raynor, M.W., et al., 1988, "Preparation of Robust Tapered Restrictors for Capillary Supercritical Fluid Chromatography", J. High Resolution Chromatog. & Chromatog. Communications, 11:289–291.

Jinno, K., et al., 1991, "Coupling of Supercritical Fluid Extraction with Chromatography", Anal. Sci., 7:361–369.

Jentoft, R.E., et al., 1972, "Apparatus for Supercritical Fluid Chromatography with Carbon Dioxide as the Mobile Phase", Anal. Chem., 44:681–686.

Campbell, R.M., et al., 1986, "Supercritical Fluid Fractionation of Petroleum–and Coal–Derived Mixtures", Anal. Chem., 58:2247–2251.

Nam, K.S., et al., 1990, "Supercritical Fluid Extraction and Cleanup Procedures for Determination of Xenobiotics in Biological Samples", Chemosphere, 20:873–880.

Campbell, R.M., et al., 1989, "Supercritical Fluid Extraction of Chlorpyrifos Methyl from Wheat at Part per Billion Levels", J. Microcolumn Separations, 1:302–308.

Onuska, F.I., et al., 1989, "Supercritical Fluid Extraction of 2,3,7,8–Tetrachlorodibenzo–p–dioxin from Sediment Samples", J. High Resolution Chromatog., 12:357–361.

Aida, T., et al., 1987, "Organic Chemisty in Supercritical Fluid Solvents: Photoisomerization of trans–Stilbene", ACS Symposium Series 329, *Supercritical Fluids: Chemical and Engineering Principles and Applications,* T.G. Squires and M.E. Paulaitis, Eds., American Chemical Society, Chapter 5, pp. 58–66.

Barber, T.A., et al., 1990, "Solubility of Solid $Ccl_4$ in Supercritical $CF_4$ Using Directly Coupled Supercritical Fluid Extraction–Mass Spectrometry", Separation Science and Technology, 25:2033–2043.

Bond, N.D., 1981, "H–Coal Pilot Plant High Pressure and Temperature Letdown Valve Experience", Proc.of the 1981 Symposium on Instrumentation and Control for Fossil Energy Processes, Argonne National Lab. Report ANL 81–62, Jun. 8–10, pp. 654–679.

Bowman, L.M., 1976, "Dense Gas–Chromatographic Studies", Dissertation, Chapter 3, pp. 35–42.

Driskell, L., 1976, "Coping with High–Pressure Letdown", Chemical Engineering, 83:113–118.

Gardner, J.F., 1980, "Critical Valve Specifications and METC Valve–Testing Projects", Proc. of the 2nd Symposium on Valves for Coal Conversion and Utilization, DOE/ MC/14522–1, Sec. 19.

Giddings, J.C., et al., 1977, "Exclusion Chromatography in Dense Gases: An Approach to Viscosity Optimization", Anal. Chem., 49:243–249.

Grancher, et al., 1973, "The SNPA–DEA Process for the Desulfurization of High Pressure Gases", Proc. of the International Conference on Control of Gaseous Sulphur Compound Emission, Apr. 10–12.

Hartmann, W., et al., 1977, "Fluid Chromatography of Oligomers", Proc. of the 6th AIRAPT International High Pressure Conference, *High–Pressure Science and Technology,* K.D. Timmerhaus and M.S. Barber, Eds., pp. 573–582.

Hawthorne, S.B., et al., 1990, "Quantitative Analysis Using Directly Coupled Supercritical Fluid Extraction–Capillary Gas Chromatography (SFE–GC) With a Conventional Split/ Splitless Injection Port", J. Chromatogr. Science, 28:2–8.

Hawthorne, S.B., et al., 1987, "Directly Coupled Supercritical Fluid Extraction–Gas Chromatographic Analysis of Polycyclic Aromatic Hydrocarbons and Polychlorinated Biphenyls from Environmental Solids", J. Chromatogr., 403:63–76.

Hirata, Y., et al., 1989, "Supercritical Fluid Extraction Combined with Microcolumn Liquid Chromatography for the Analysis of Polymer Additives", J. Microcolumn Separations; vol. 1, No. 1, 1989, pp. 46–50.

Illing, H.H., 1982, "Design Principles of Low Impingement Type Slurry Letdown Valves", Proc. of the 1982 Symposium on Instrumentation and Control for Fossil Energy Processes, Argonne National Lab. Report ANL 82–62, pp. 461–468.

Klesper, E., 1978, "Chromatography with Supercritical Fluids", Angew. Chem. Int. Ed. Eng., 17:738–746.

Klesper, E., et al., 1978, "Apparatus and Separations in Supercritical Fluid Chromatography", European Polymer Journal, 5:77–88.

Lapple, C.E., 1943, "Isothermal and Adiabatic Flow of Compressible Fluids", Trans. American Institute of Chemical Engineers, 39:385–432.

Liepmann, H.W., et al., 1957, "Flow in Ducts and Wind Tunnels", *Elements of Gasdynamics,* Chapter 5, pp. 124–143.

I. Moradinia, et al., 1987, "Solubilities of Five Solid n–Alkanes in Supercritical Ethane", ACS Symposium Series 329, *Supercritical Fluids,* T.G. Squires and M.E. Paulaitis, Eds., American Chemical Society, Chapter 11, pp. 130–137.

Nair, J.B., et al., "On–Line Supercritical Sample–Preparation Accessory for Chromatography", LC–GC, 6:1071–1073.

Nilsson, W.B., et al., 1989, "Supercritical Fluid Carbon Dioxide Extraction in the Synthesis of Trieicosapentaenoylglycerol from Fish Oil", ACS Symposium Series 406, *Supercritical Fluid Science and Technology,* K.P. Johnston and J.M.L.Penninger, Eds., Chapter 5, pp. 89–108.

Platt, R.J., 1981, "High–Pressure Slurry–Letdown Valve Designs for Exxon Coal–Liquefaction Pilot Plant", Proc. of the 2nd Symposium on Valves for Coal Conversion and Ultilization, DOE/MC/14522–1, Sec. 6.

Rizvi, et al., 1988, "Concentration of Omega–3 Fatty Acids from Fish Oil Using Supercritical Carbon Dioxide", ACS Symposium B.A. Charpentier and M.R. Sevenants, Eds., Chapter 5, pp. 89–108.

Saito, M., et al., "Fractionation by Coupled MicroSupercritical Fluid Extraction and Supercritical Fluid Chromatography", (Royal Soc. Chem. Chromatography Monographs), *Supercritical Fluid Chromatography,* R.M. Smith, 1988, Chapter 8, pp. 203–230.

Saito, M., et al., 1989, "Enrichment of Tocopherols in Wheat Germ by Dirdctly Coupled Supercritical Fluid Extraction with Semipreparative Supercritical Fluid Chromatography", J. Chromatogr. Sci., 27:79–85.

Smith, R.D., et al., 1986, "Performance of Capillary Restrictors in Supercritical Fluid Chromatography", Anal. Chem., 58:2057–2064.

Temelli, F., et al., 1988, "Supercritical Carbon Dioxide Extraction of Terpenes from Orange Essential Oil", ACS Symposium Series 366, *Supercritical Fluid Extraction and Chromatography,* B.A. Charpentier and M.R. Sevenants, Eds., Chapter 6, pp. 109–126.

Wright, B.W., et al., 1988, "Analytical Supercritical Fluid Extraction Methodologies", ACS Symposium Series 366, *Supercritical Fluid Extraction and Chromatography,* B.A. Charpentier and M.R. Sevenants, Eds., Chapter 3, pp. 44–62.

Conoflow Corp. Valve Catalog sheets for 1968 and 1969.

Greibrokk, T., et al., 1984, "New System for Delivery of the Mobile Phase in Supercritical Fluid Chromatography", *Anal. Chem.,* 56:2681–2684.

Wheeler, J.R., et al., "Is SFC Worth the Effort?", *Res. & Dev.;* Chromatography; Feb:134–138.

Hirata, Y., et al., "Direct Sample Injection in Supercritical Fluid Chromatography with Packed Fused Silica Column", *Journal of High Resolution Chromatography & Chromatography Communications,* vol. 11, Jan. 1988; pp. 81–84.

Berger, T.A., et al., "A New Supercritical Fluid Chromatograph", Paper 255, HPLC–92, 16th International Symposium on Column Liquid Chromatography, Lafayette, IN.

Thiebaut, D., et al., "Supercritical–Fluid Extraction of Aqueous Samples and On–Line Coupling to Supercritical–Fluid Chromatography", *On–Line Coupling of SFE and SFC,* 1989 Elsevier Science Publishers B.V.; pp. 151–159.

Wheeler, J. R., et al., "Supercritical Fluid Extraction and Chromatography of Representative Agricultural Products with Capillary and Microbore Columns", *Journal of Chromatographic Science,* vol. 27, Sep. 1969; pp. 534–539.

Lopez–Avila, Viorica, et al., "SFE/IR Method for the Determination of Petroleum Hydrocarbons in Soils and Sediments", Environmental Monitoring Systems Laboratory, Contract No. 69–C1–0029, Section 4, p. 8, Undated.

Levy, Joseph M., et al., "Multidimensional Supercritical Fluid Chromatography and Supercritical Fluid Extraction", *Journal of Chromatographic Science,* vol. 27, Jul. 1989, pp. 341–346.

Schwartz, H.E., et al., "Gradient Elution Chromatography with Microbore Columns", *Analytical Chemistry,* vol. 55, No. 11, Sep., 1983, pp. 1752–1760.

Schwartz, H.E., et al., "Comparison of Dynamic and Static Mixing Devices for Gradient Micro–HPLC", *Journal of Chromatographic Science,* vol. 23, Sep., 1985, pp. 402–406.

SFE–Plus Supercritical Fluid Extraction System brochure, Micro–Tech Scientific, Undated.

Kalinoski, Henry T., et al., "Supercritical Fluid Extraction and Direct Fluid Injection Mass Spectrometry for the Determination of Trichothecene Mycotoxins in Wheat Samples", *Anal. Chem.* 1986, 58, 2421–2422.

Ramsey, Edward D., et al., "Analysis of Drug Residues in Tissue by Combined Supercritical–Fluid Extraction–Supercritical–Fluid Chromatography–Mass Spectrometry–Mass Spectrometry", *Journal of Chromatography,* 464 (1989) 353–357.

Sims, Marc, et al., "Design and Control of CO2 Extraction Plants", presented at 2nd International Symposium on Supercritical Fluids, May 20–22, 1991, Boston, MA; pp. 1–8.

Lack, E., et al., "Findings and Experience Acquired in Operating Industrial High Pressure Extraction Plants with Supercritical CO2", pp. 473–480, Undated.

Engineered Pressure Systems Inc. "Supercritical Fluid Extraction" brochure, Undated.

SITEC brochure on HP–Spray Drying/Micronisation/Supercritical Extraction and pilot plants, Undated.

Brochure from Extract Company GMBH on "Extraction with supercritical gases" production plants, Undated.

Brochure "Hochdruck–Extraktion—$CO_2$ " from UHDE, Undated.

Korner, J.P., New Developments in the Design and Construction Symposium on Supercritical Fluids, Tome 1, Nice France, Oct. 17, 18, 19, 1988; pp. 633–641.

"Instruments for Separation and Analysis" Product Guide 12, Isco, Inc., Brochure 9501, Jan. 1995.

Suprex Corporation brochure "MPS/225".

Specs for Chassis for Ultra Plus Extrapolator by Micro–Tech Scientific, by F. Yang, Sep. 1994.

Yang, F. J., et al., "Design Concepts for a New Generation Supercritical Fluid Extraction System", Micro–Tech Scientific, Undated.

McNally, Mary Ellen P., et al., "Supercritical Fluid Extraction Coupled with Supercritical Fluid Chromatography for the Separation of Sulfonylurea Herbicides and Their Metabolites from Complex Matrices", *Journal of Chromatography,* 435 (1988) 63–66.

Hawthorne, Steven, et al., "Analysis of Flavor and Fragrance Compounds Using Supercritical Fluid Extraction Coupled with Gas Chromatography", *Anal. Chem.,* 1988, 60, 472–473.

Marc Sims S–F–E brochure on "Dense Gas Management System for Supercritical Fluid Extraction and Processing", Undated.

Cassat, D., et al., "Extraction of PCB from Contamined Soils by Supercritical $CO_2$", International Symposium on Supercritical Fluids, Tome 2, Nice France, Oct. 17, 18, 19, 1988, pp. 771–776.

De Ruiter, C., et al., "Design and Evaluation of a Sandwich Phase Separator for On–Line Liquid/Liquid Extraction", *Analytica Chimica Acta,* 192(1987) pp. 267–275.

Advertisement "SFE Analyser 3000", Fisons Instruments SpA; LPI Mar./Apr. 1993.

"RIA" Bulletin 7250, Beckman Instruments, Undated.

"Concept 4" brochure; Micromedic Systems, Undated.

"The HP 7680A Supercritical Fluid Extractor" brochure; Hewlett–Packard, Undated.

"Supercritical Fluid (Dense Gas) Chromatography/Extraction with Linear Density Programming" Lyle M. Bowman, Jr., Marcus N. Myers, and J. Calvin Giddings; *Separation Science and Technology,* 17(1) (1982) 271–287.

"Microscale Supercritical Fluid Extraction and Coupling of Microscale Supercritical Fluid Extraction with Supercritical Fluid Chromatography" Muneo Saito, Toshinobu Hondo, Masaaki Senda, *Progress in HPLC* vol. 4 (1989) Yoshioka, et al. (Eds) pp. 87–110.

"Fractionation of Anhydrous Milk Fat by Superficial Carbon Dioxide" by Joseph Arul, Armand Boudreau, Joseph Makhlouf, Rene Tardif, and Madhu R. Sahasrabudhe, *Journal of Food Science* vol. 52, No. 5, 1987, pp. 1231–1236.

"Grobtenchnische Anlagen zur Extraktion mit uberkritischen Gasen" by Von R. Eggers; Angew. Chem. 90, 1978, pp. 799–802.

"New Pressure Regulating System for Constant Mass Flow Supercritical–Fluid Chromatography and Physico–Chemical Analysis of Mass–Flow Reduction in Pressure Programming by Analogous Circuit Model" by M. Saito, et al.; *Chromatographia* vol. 25, No. 9, Sep. 1988, pp. 801–805.

"Extraction with supercritical fluids: Why, how, and so what" Gale G. Hoyer; CHEMTECH, Jul. 1985; pp. 440–448.

Suprex AutoPrep 44 brochure (The AutoPrep 44 was on Sale on or around late 1992.).

"Portable Thermal Pump for Supercritical Fluid Delivery", *Analytical chemistry* 67 (1995) Jan. 1, No. 1, pp. 212–219.

Suprex PrepMaster manual, pp. 8–1 to 8–12, May 1995.

Suprex AutoPrep 44 brochure, p. 6, Undated.

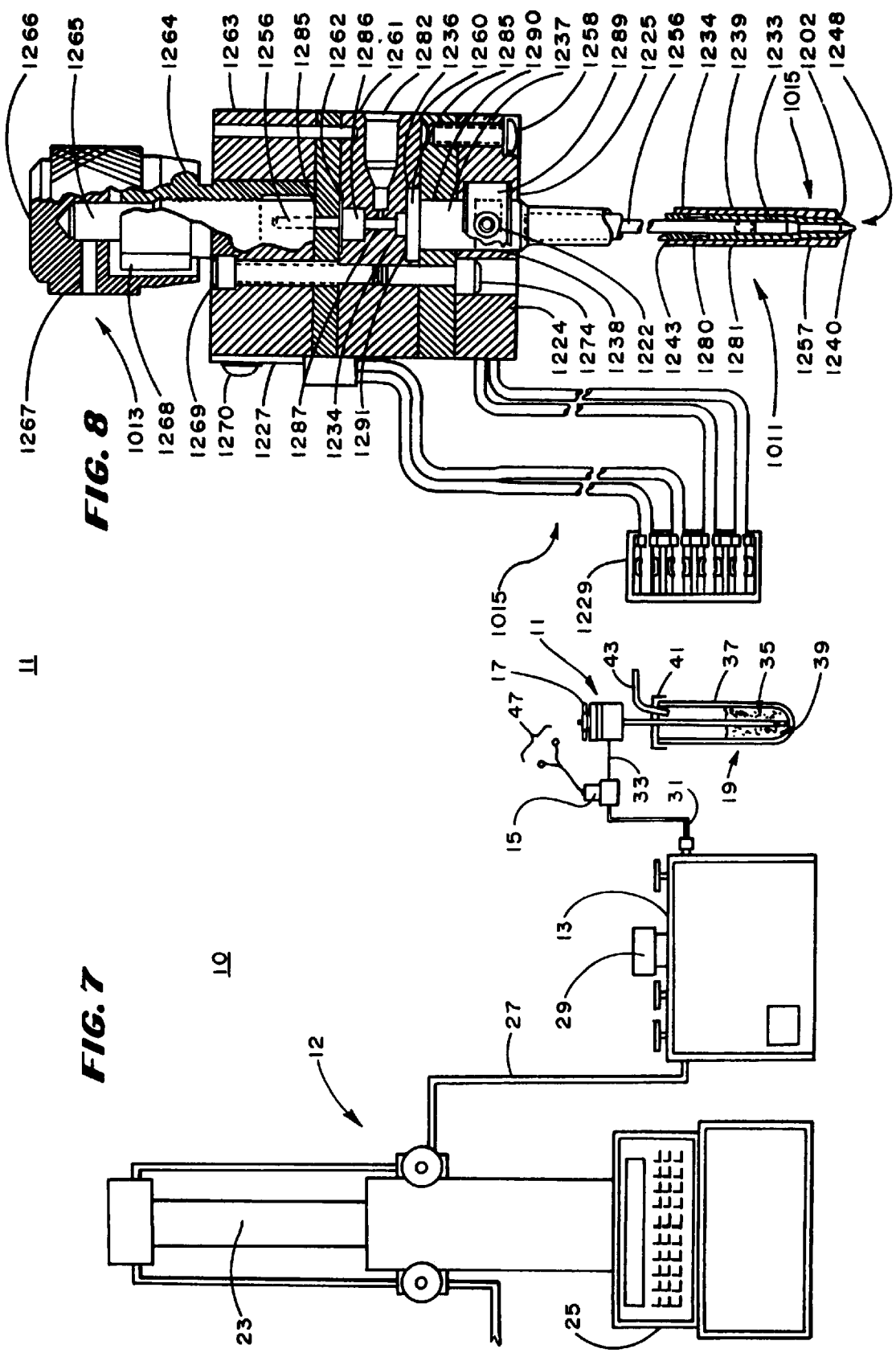

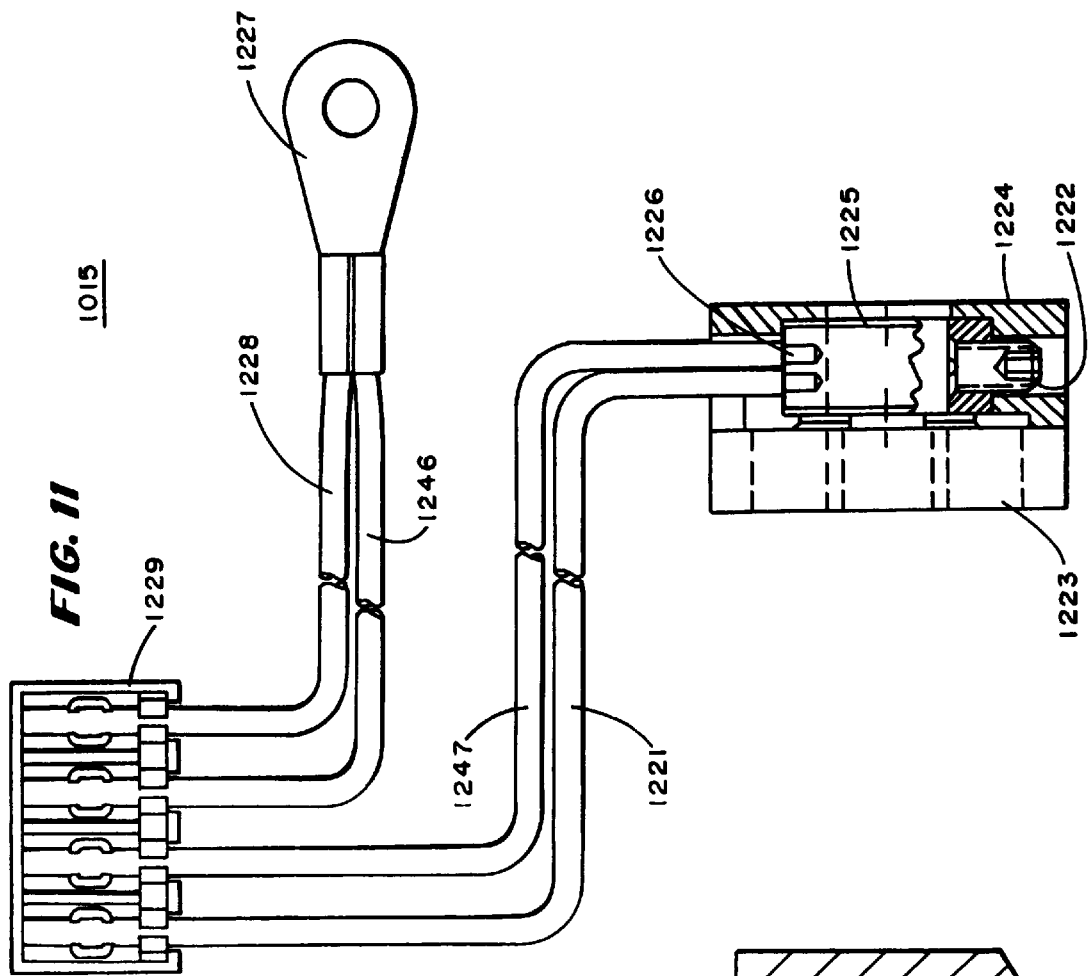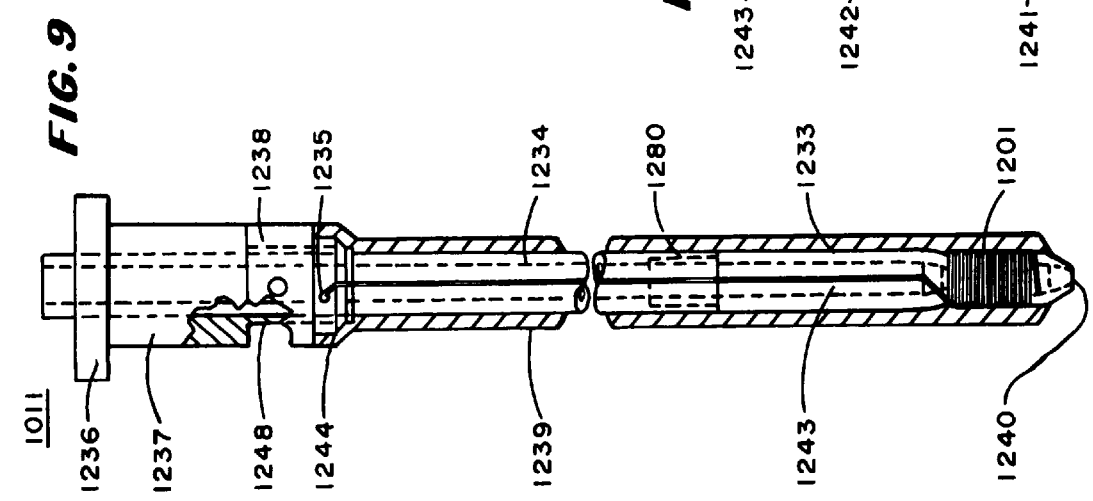

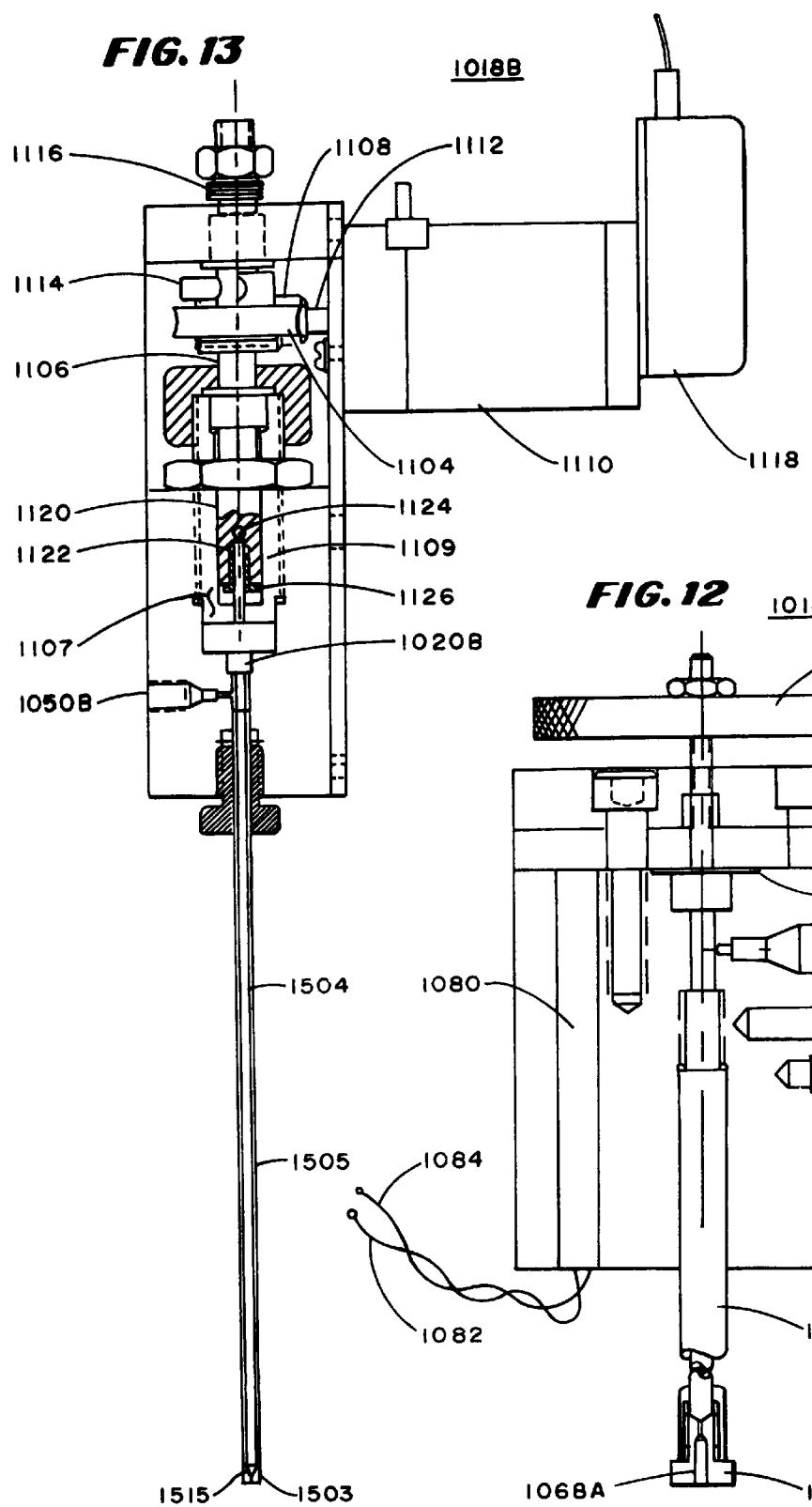

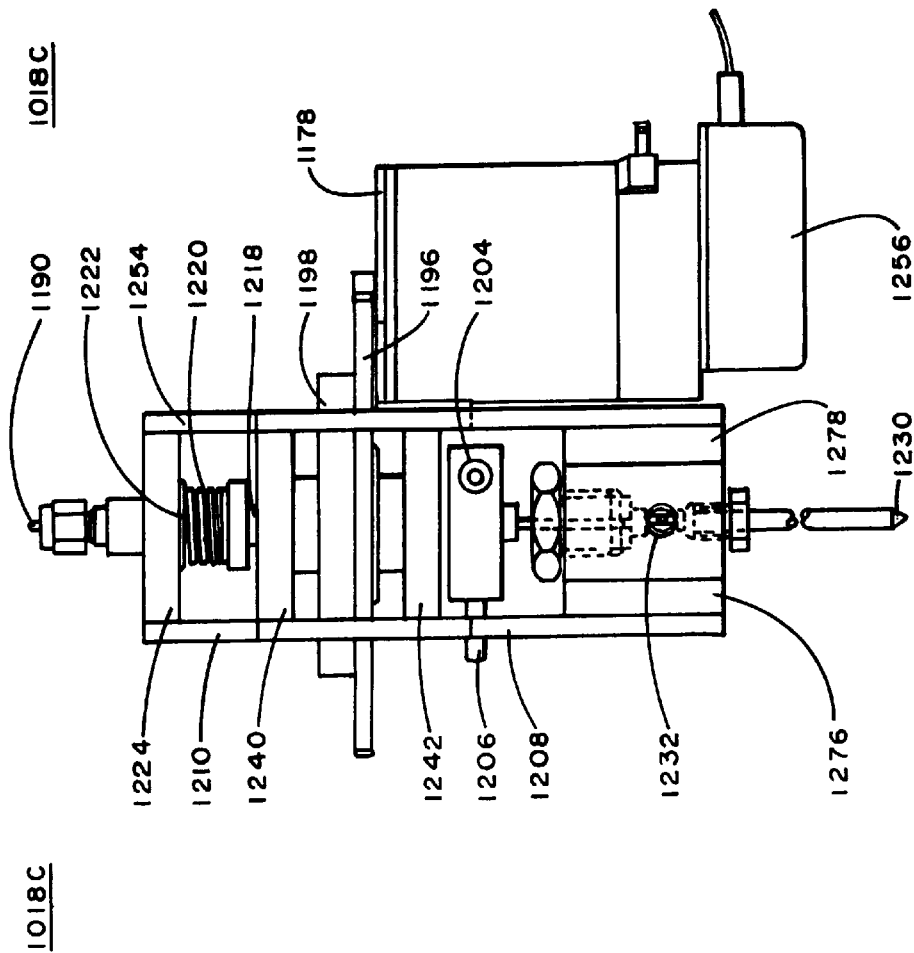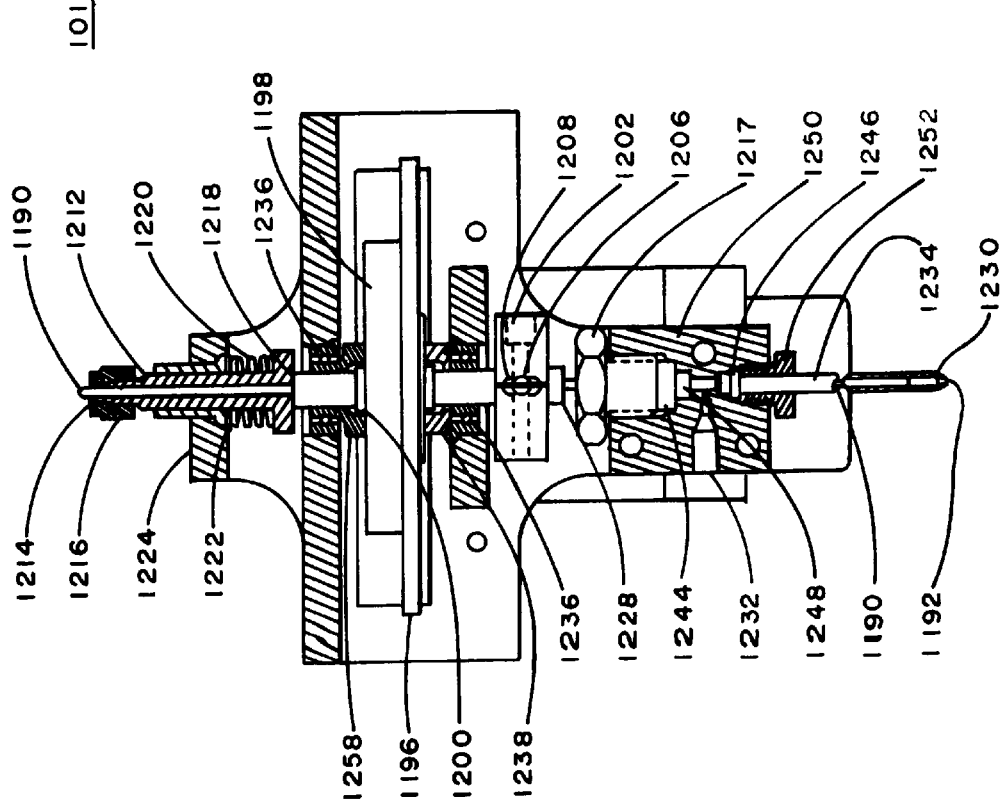

APPARATUS AND METHOD FOR SUPERCRITICAL FLUID EXTRACTION OR SUPERCRITICAL FLUID CHROMATOGRAPHY

RELATED CASES

This application is a divisional of U.S. application Ser. No. 08/804,682, filed Feb. 25, 1997, now U.S. Pat. No. 5,750,027, which is a divisional of U.S. application Ser. No. 08/542,683, filed Oct. 13, 1995, now U.S. Pat. No. 5,614,089 which is a continuation of U.S. application Ser. No. 08/096,919 filed Jul. 23, 1993, now abandoned, which is a continuation-in-part application of U.S. application Ser. No. 08/027,257, filed Mar. 5, 1993, now U.S. Pat. No. 5,268,103, which is a continuation-in-part application of U.S. application Ser. No. 07/908,458 filed Jul. 6, 1992, now U.S. Pat. No. 5,198,197, which is a division of U.S. application Ser. No. 07/795,987, filed Nov. 22, 1991, now U.S. Pat. No. 5,160,624, which is a continuation-in-part of U.S. application Ser. No. 07/553,119, filed Jul. 13, 1990, now U.S. Pat. No. 5,094,753, for APPARATUS AND METHOD FOR SUPERCRITICAL FLUID EXTRACTION.

BACKGROUND OF THE INVENTION

This invention relates to supercritical fluid extraction and supercritical fluid chromatography and more particulary to the collection of extracted or separated sample in supercritical fluid extraction or supercritical fluid chromatography.

In supercritical fluid extraction, an extraction vessel is held at a temperature above the critical point and is supplied with fluid at a pressure above the critical pressure. Under these conditions, the fluid within the extraction vessel is a supercritical fluid. In supercritical fluid chromatography, a similar process is followed except that the supercritical fluid moves the sample through a column, separates some of the components of the sample one from the other and removes the components from the column.

In one class of supercritical fluid extraction of chemical components from a sample using a supercritical fluid, the components dissolved in the extraction fluid are separated from the fluid for further analysis by allowing the extraction fluid to vaporize.

In a prior art type of supercritical fluid extraction apparatus, the analyte precipitates on the surfaces of the expansion device, such as for example, along the walls of a linear capillary tube restrictor or on the walls of tubing beyond the limiting orifice of a point restrictor as the extraction fluid vaporizes. Commercially available metering valves as point restrictors require the analyte to be removed from the internal surface area of the connecting conduit or in tubing downstream from the valve in which it precipitates.

The analyte is collected in a collection solvent located in a collection vessel. In the prior art, one key advantage is achieved by collecting the analyte in collection solvent within the collection vessel which advantage is that volatile analytes are less likely to be lost by their own vaporization.

This loss occurs because, as the extraction fluid vaporizes, volatile analytes may also tend to vaporize and be lost with the extraction fluid. By collecting the effluent in supercritical fluid extraction and in supercritical fluid chromatography in a collection solvent, volatile compounds tend to be dissolved in the collection solvent rather than being lost with the expanded supercritical fluid, which is a gas after expansion. The higher recovery rate of volatile analytes is advantageous when the content of volatile compounds in the sample is small and when the volatile content is to be quantified.

The prior art apparatuses and methods for collecting sample have the disadvantages of requiring an excessive amount of time and equipment to remove analytes from tubing and of losing some analytes.

In collecting sample (analytes) during supercritical fluid extraction and supercritical fluid chromatography, a fluid flow restrictor is included to maintain high pressure in an extraction chamber or column while allowing a controlled flow rate through the sample being extracted. One type of restrictor is a length of small internal diameter tubing, often referred to as a capillary restrictor or capillary.

To avoid freezing or deposition of water or other extracted substances dissolved in the fluid on the wall of the tubing, the capillary is heated. The need for heating is especially great when using a cold collection trap comprising a cold collection liquid solvent in which the outlet end of the capillary is immersed and through which gasified extractant is bubbled.

In one prior art heated restrictor, the capillary is heated by thermal conduction along its length and by heat or enthalpy added to the fluid within the capillary, which moves along with the fluid flow to the outlet end of the capillary. The fluid discharges into a cold, dry tube of relatively large inside diameter. This larger tube then dips into the cold solvent trap. Ice and extracts build up on this tube but do not plug it because of the large diameter. This is described in international patent application number WO 92/06058, dated Apr. 14, 1992.

This arrangement is disadvantageous because it is often difficult to remove extract solidified on the inside of the large tube for assay.

It is known to directly resistance heat a member and to control the heat with a feedback system using the electrical resistance of the member to measure its temperature and compare it to a reference temperature. This technique is taught for use in a gas tube by U.S. Pat. No. 4,438,370; the disclosure of which is incorporated herein by reference.

In another restrictor-collector system that may or may not be prior art, a heated variable restrictor is mounted within a heating block. A tube extends from the heated variable restrictor into the collection trap.

This type of variable restrictor may still have the disadvantage of depositing extract on the tubular walls of the tube that extends from the heated variable restrictor into the collection trap. A system of this type is described by Maxwell, et al. in "improved SFE Recovery of Trace Analytes from Liver Using an Integral Micrometering Valve-SPE Column Holder Assembly" *Journal of High Resolution Chromatorgraphy* v. 15, December 1992, pp. 807–811.

SUMMARY OF THE INVENTION

Accordingly, it is an object of the invention to provide a novel technique and apparatus for supercritical fluid extraction or supercritical fluid chromatography.

It is a further object of the invention to provide a novel technique for reducing the loss of sample in supercritical fluid extraction and supercritical fluid chromatography.

It is a still further object of the invention to provide a novel technique and apparatus for reducing time lost in recovering sample that has formed a coat in tubing during collection.

It is a still further object of the invention to provide a novel variable orifice fluid restrictor for use with a supercritical fluid extractor or chromatograph.

It is a still further object of the invention to provide a novel variable orifice fluid restrictor whose orifice is located at the end of a long, thin probe.

It is a still further object of the invention to provide a novel technique for controlling the pressure in a supercritical fluid extractor or chromatograph.

It is a still further object of the invention to provide a novel supercritical extraction apparatus that processes a series of samples automatically.

It is a still further object of the invention to provide a novel supercritical extraction apparatus that can use different sizes of collection vials through the use of a variable orifice restrictor whose orifice is located at the end of a long, thin probe.

It is a still further object of the invention to provide a novel supercritical extraction apparatus that allows the vials to be interchanged during the extraction process.

It is a still further object of the invention to provide a novel supercritical extraction collection apparatus that improves trapping efficiency by controlling the temperature and pressure of the collection vial and yet is automatically loaded without the need for handling by an operator.

It is a still further object of the invention to provide a novel supercritical extraction collection apparatus that reduces collection solvent loss by controlling the temperature and pressure of the vial and yet is automatically loaded without the need of handling by an operator.

It is a still further object of the invention to provide a novel supercritical extraction collection apparatus that avoids plugging of the variable orifice restrictor by locating the orifice at the outlet of the restrictor with no significant connecting tubing between the orifice and the outlet.

It is a still further object of the invention to provide the location of the orifice of a variable orifice restrictor directly within a collecting trap for the purpose of trapping extracted substances.

It is a still further object of the invention to provide a variable orifice restrictor having a heated orifice located within the trap for the purpose of trapping extracted substances while also avoiding plugging of the restrictor.

It is a still further object of the invention to provide a novel collecting trap using reduced temperature for the purpose of trapping extracted substances but which nonetheless does not cause the restrictor orifice to plug through cooling the orifice.

It is a still further object of the invention to provide a novel method of maintaining a hot orifice which is immersed in a trap without heating the trap.

It is a still further object of the invention to provide a novel method of maintaining the temperature of an elongated restrictor heated by electrical and/or thermal conduction along some part of its length.

It is an object of the invention to provide a novel restrictor tubing outlet end thermally insulated from the surrounding collection solvent into which it is immersed.

In accordance with the above and further objects of the invention, a controlled variable expansion of supercritical fluid used in supercritical fluid extraction or supercritical fluid chromatography is provided by a restrictor. This restrictor: (1) permits the analyte, which had been dissolved in the supercritical fluid to be deposited directly into an external environment, such as a collection vessel, instead of first depositing it into a connecting conduit that leads to an external collecting vessel; (2) can be used without a connecting conduit; and (3) allows independent control of the fluid back pressure to change the solvating power of the supercritical fluid independently of the flow rate.

The restrictor is variable and incorporates controllable metering means with at least part of said metering means being movable and controllable by an adjusting means extending out of the region comprising the analyte collection means to effect its said control and with its outlet being substantially immediately surrounded by a region comprising an analyte collection means.

In the preferred embodiment, the variable restrictor is a point (orifice) restrictor as opposed to a linear (capillary tube) restrictor. It produces expansion of the supercritical fluid at the point of discharge to a collection system. By eliminating the connecting conduit, the analyte is prevented from precipitating inside the apparatus. The variable restrictor incorporates controllable metering means with at least part of said metering means being movable to effect its said control. The metering means outlet is substantially immediately surrounded by a region comprising an analyte collection means. The metering means is controlled by an adjusting means extending out of the region comprising the analyte collection means.

The apparatus presented here provides an abrupt expansion of the supercritical fluid, and controls the location at which the analytes come out of solution to a location near or at the point where the fluid flow reaches the outside environment. This eliminates the necessity of secondary flushing of the restrictor and associated connecting conduit to move the analytes from the restrictor system and convey them to the outside environment.

The novel restrictor includes a metering valve having an adjustable metering orifice at the end of a long, narrow external probe in contact or nearly in contact with its external surroundings, such as a collection solvent in a collection vessel. This apparatus provides for expansion of the supercritical fluid or liquid to a gas at the tip of a probe, which can be inserted into a collection vessel. The expanded extraction fluid is allowed to bubble as a gas through a collection solvent. Alternatively, it may spray as a liquid or gas entraining a liquid or solid into a chilled or pressurized empty collection vessel. Supercritical pressures are maintained upstream of the tip of the probe, preventing the precipitation of extracted analytes in the restrictor.

Regulation of back pressure (pressure upstream of the tip of the probe) is achieved by a variable orifice created at the tip of the probe. The variable orifice allows control of the flow rate of the fluid independent of pressure, and therefore variable control over the extraction process. Once the extraction fluid is allowed to expand to a gas, its ability to carry the analyte is lost and the analyte precipitates. Because this expansion occurs at the tip of the probe, the analyte precipitates directly into the collection solvent or vessel.

More specifically, a variable-orifice fluid restrictor for use with a supercritical extractor or chromatograph includes an inlet line for fluid at a pressure above its critical pressure and an extended tubular probe having an inner and an outer surface and a proximal and distal end. The proximal end of the probe is disposed toward the inlet line and the distal end is disposed toward the collection environment such as in a collection chamber or the like. The distal end of the probe contains an adjustable orifice means adapted for metering the fluid, which orifice means is comprised of first and second orifice members and an adjusting stem having first and second ends.

The adjustable orifice means is located within the inner surface of the probe adjacent to the outer surface of the probe tip with at least part of the orifice means being movable to effect its said control. Its outlet is substantially immediately surrounded by a region comprising an analyte collection means and is controlled by the adjustable stem that serves as an adjusting means in the preferred embodiment, extending out of the region comprising the analyte collection means. The adjusting stem has first and second ends, the first end of the stem being adapted to movably control the metering means and said second end of the stem carrying a feature which provides for independent control of the metering means.

The orifice means is adjustable by moving the adjusting stem. For this purpose, the second end of the adjusting stem is located at the proximal end of the probe and the first end of the adjusting stem is located at the distal end of the probe and is connected to and adapted for moving the first orifice member with respect to the second orifice member, thereby controlling the adjustable orifice for varying the restriction of fluid passing through the adjustable orifice. The second end of the adjusting stem extends past the proximal end of the probe and cooperates with an orifice adjustment control.

To automate the operation under the control of a microprocessor, a motor operated fraction collector, a motor operated sample source and a motor operated sample injector automatically move samples and collection containers into an extraction station, inject samples into the extraction pressure vessel, perform extraction and collect extractant in different appropriate collection containers in a timed sequence to permit extracting of a series of samples with minimum human handling.

In the preferred embodiment, a movable motor member is aligned: (1) with an opening in a sample cartridge reel that moves sample cartridges carrying samples into the extraction station; and (2) with an opening in the extraction pressure vessel. The movable member is dimensioned to be capable of sealing a correspondingly sized opening in the pressure vessel and adapted to move the sample cartridge into the pressure vessel and seal the pressure vessel. Motors are provided to operate the valves to permit the extraction operation on the cartridge. The movable member is removed from the pressure vessel after extraction and returns the sample cartridge back to the sample reel.

In operation, the sample to be extracted is placed within the cartridge and the cartridge inserted into and sealed within a pressure vessel. Upon insertion, one of two outlet fittings communicates with the interior of the cartridge and the other with the interior of the pressure vessel outside the cartridge. An inlet to the pressure vessel communicates with the outlet of a pump which pumps the supercritical fluid along a path that heats it and through a programmable valve into the interior of the pressure vessel and extraction cartridge. For each extraction, the valve is automatically opened by a computer controlled motor that releases a valve element to permit flow and closes it to prevent further flow.

To remove any contaminants from outside of the cartridge, the outlet communicates within the inside of the pressure vessel and outside of the cartridge and thus, permits the supercritical fluid to cleanse the outside of the cartridge and the inside walls of the pressure vessel from contaminants as it flows outwardly to a contaminant collector.

For extraction, the cartridge includes an outlet that cooperates with an extractant outlet of the pressure vessel and is connected to the fraction collector so that supercritical fluid flows into the cartridge, out of a fitting that communicates with the interior of the cartridge and into an appropriate collection container.

In the operation of an automatic supercritical fluid extractor, sample cartridges are disposed in the sample changer and are automatically transported to the pressure vessel for extraction by a supercritical fluid.

In the preferred embodiment, this transport is first horizontal in a reel of successive sample vials and then vertical through an opening into the pressure vessel. The transport mechanism seals the pressure vessel and is locked in place and motor-driven valves automatically apply extracting fluid first through a purge cycle and then through one or more extracting cycles to extract fluid. A fraction collector, which in the preferred embodiment is a reel holding container, moves the fraction collector containers into position for collection. In the alternative, extractant fluid tubing may be moved from container to container.

An embodiment of collection vial piercing mechanism includes means for adding temperature and positive internal pressure control for the vial. Positive pressure in the vial suppresses misting of the collection solvent and dissolved extract. Also, excess gas from the vial is contained and then routed to a remote location for collection and disposal.

To collect sample, one embodiment of collection system includes multiple collecting vials partially filled with collection solvent through which the restrictor bubbles $CO_2$ with entrained extractant. Each vial has a slitted septum on its upper, open end to allow passage of the end of the restrictor into the vial. In one embodiment, the restrictor is lowered into the restrictor by a rod connected directly to the extraction cartridge elevator.

In still another embodiment, the vial is lifted by a vial lifter that is separate from the cartridge elevator. To permit changing of the vial during the extraction process, a lift that functions separately from the sample cartridge elevator is required.

This embodiment has the advantage over moving restrictor embodiments of not causing wear and breakage of the restrictor by flexing its connecting tubing repeatedly. It has the advantages of the embodiments in which the vial lifter is directly connected to the cartridge elevator of: (1) allowing the vials to be changed during the extraction process without depressurizing the extraction chamber; (2) better trapping efficiency; (3) lower extract/solvent losses; (4) reduced freezing and plugging of the restrictor; and (5) reduced icing up of the outside of the vial.

The ability to change vials during the extraction process has several advantages, such as for example: (1) it makes it relatively easy to change the conditions of the extraction, such as temperature and pressure or to remove certain substances from the sample matrix and deposit each substance in a separate vial; (2) it is useful for investigating extraction kinetics; and (3) if a separate lift is used, different size vials may be accommodated since the stroke is no longer tied to the extraction cartridge elevator.

Changing a vial after an extraction without having to depressurize the extraction chamber makes using multiple wash stations easier. Wash stations are used to clean the outside of the restrictor. Several vials are used in sequential washes of the restrictor to dilute any possible contamination from one extraction to another to acceptable levels. Without a separate vial lift, the chamber would have to be depressurized and repeatedly loaded with a blank for each washing step.

Trapping efficiency and low collection solvent losses can be gained by several techniques. One such technique requires reduced collection solvent temperature during extraction on the order of five degrees Centigrade or less. However, reduced temperature, while improving trapping and reducing losses, may also create problems with restrictor plugging and icing up of the vial. Ice on the outside of a vial may interfere with the via being lowered into the vial rack after collection. To prevent these problems, heat must be supplied to the vial to maintain a minimum temperature. Ideally, a system would precool the vial before the extraction begins and then add heat to maintain this temperature.

To improve trapping and reduce losses, a sealed system is used with a regulator to maintain pressure, and the collection vials are pressurized sufficiently to reduce the mist and vapors resulting from the violent expansion of the gas exiting the restrictor in an unpressurized vial and to prevent loss of gas through the vial's vent. The pressure is sufficiently elevated to decrease the vaporization rate of collection solvent and extract so that at a given mass flow rate of gas, the gas volume and bubble size are reduced. In the sealed system, the gases and vapors may be routed for proper and safe disposal.

To maintain an adequate solvent level, a liquid level control system with optical sensing of the liquid level in the vial is provided. This system activates a collection solvent replenishment means when the collection vial loses too much collection solvent due to evaporation. The fluid level sensing system benefits from the pressurized system because increased pressure reduces the violent bubbling and this makes optical sensing easier.

In one embodiment, the collector includes means for receiving the fluid from the extractor and supplying it to a collection liquid at a temperature that permits partition between the extract and the extractant by avoiding freezing of the extractant before partition but at a temperature not so high as to cause the bubbling away of the extract with the extractant. This usually involves cooling the collection liquid.

The means for supplying the fluid to the collection liquid is a variable orifice pressure release restrictor with the orifice immersed in the collecting fluid. To this end, the orifice is located at the end of a long, thin probe. Because the fluid often carries entrained water and because the region of the orifice is cooled through fluid expansion, ice can form at the orifice and plug it. To prevent this from happening the metal walls around the orifice are heated. The probe, especially including the heated area, is insulated to decrease the heating effect on the cold collection fluid. The heat and insulation minimize the transfer of heat to the collection liquid while maintaining the orifice which is immersed in a cold solvent at the proper higher temperature to avoid freezing or internal deposition.

As can be understood from the above description, the supercritical extraction technique has several advantages, such as for example: (1) it automates the sample injection and fraction collection part of the extraction process as well as automating the extraction itself; (2) it allows the vials to be changed during the extraction process without depressurizing the extraction chamber; (3) it provides good trapping efficiency; (4) it provides low extract/solvent losses; (5) it provides reduced freezing and plugging of the restrictor while allowing the vial to be operated at a lower temperature to increase collection efficiency; (6) it reduces icing up of the outside of the vial; (7) it permits the conditions of the extraction, such as temperature and pressure, to be changed such as to remove certain substances from the sample matrix and deposit each substance in a separate vial; (8) it is also useful for investigating extraction kinetics by changing the vial during the extraction for examination; (9) it permits the use of different size vials because the stroke of a lift is no longer tied to the extraction cartridge elevator; and (10) it permits the use of multiple wash stations to clean the outside of the restrictor.

From the above description, it can be understood that the variable restrictor of this invention has several advantages, such as for example: (1) it avoids loss of volatile analytes by dissolving the sample in a solvent; (2) the analytes are not deposited on the walls of the restrictor or its connecting tubing when expanding controllable supercritical fluid, and thus flushing of the expansion device to recover the analyte is not required; (3) the extraction conditions can be controlled with a controllable expansion device downstream from the extractor by modifying the pressure (density and solvating power) of the supercritical fluid independently of flow rate; and (4) the necessity of secondary flushing of a restrictor and associated connecting conduit to move the analytes from the restrictor system and convey them to the outside environment is eliminated.

DESCRIPTION OF THE DRAWINGS

The above noted and other features of the invention will be better understood from the following detailed description when considered with reference to the accompanying drawings in which:

FIG. 7 is a schematic drawing of a supercritical fluid extraction system in accordance with an embodiment of the invention;

FIG. 8 is a partly-schematic, partly-sectioned view of variable restrictor assembly in accordance with an embodiment of the invention;

FIG. 9 is a partly broken away, partly sectioned view of a variable restrictor forming a portion of the assembly of FIG. 8;

FIG. 10 is an enlarged fragmentary sectional view of the restrictor of FIG. 9;

FIG. 11 is a a schematic view of electrical connections included in the assembly of FIG. 7 to control the temperature of the variable restrictor;

FIG. 12 is a front elevational view, partly broken away and sectioned of a variable restrictor used in the embodiment of FIG. 7;

FIG. 13 is a front elevational view, partly broken-away and sectioned of another embodiment of variable restrictor modified for automatic operation in accordance with an embodiment of the invention;

FIGS. 15 and 16 are front and side elevational sectional views of variable restrictors in accordance with an embodiment of the invention;

DETAILED DESCRIPTION

Figure 1:
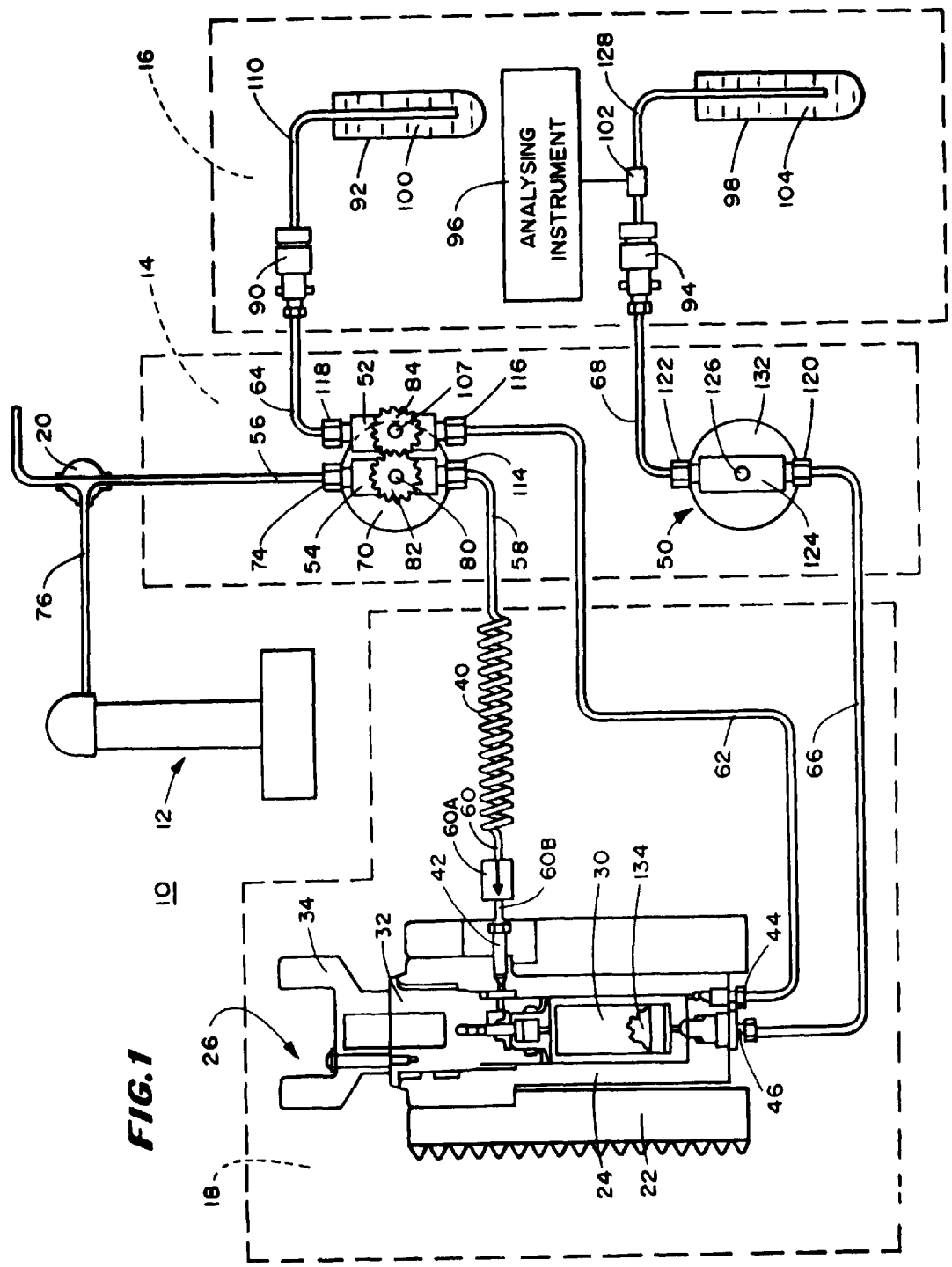
FIG. 1 is a schematic diagram illustrating the operation of a single supercritical fluid extraction system according to the invention.

In FIG. 1, there is shown a schematic fluidic diagram of one channel of a dual-channel supercritical fluid extraction system 10 having a pumping system 12, a valve system 14, a collector system 16 and a pressure vessel and fluid-extraction assembly 18. The pumping system 12 communicates with two extraction cartridges within the pressure vessel and fluid-extraction assembly 18 and for this purpose is connected through a tee joint 20 to two identical valve systems, one of which is shown at 14. Each valve system communicates with a different one of two inlets for the corresponding one of two extraction cartridges.

The valve system 14 and a second valve system (not shown in FIG. 1) which is connected to the other branch of the tee joint 20 are each connected to two different collector systems 16, one of which is shown in FIG. 1, and to different ones of the two extraction cartridges in the pressure-vessel and fluid-extraction assembly 18 so that, two extraction operations can be performed at the same time using the same pumping system 12.

With this arrangement, the valve system 14 causes: (1) supercritical fluid to flow from the pumping system 12 into a space between a cartridge and the interior of the pressure vessel of the pressure-vessel and fluid-extraction assembly 18 for purging the outside of the cartridge and the inside of the pressure vessel; and (2) applies supercritical fluid through the cartridge for extraction of a sample 134 therein. Because the fluid is applied both to the interior of the cartridge and the exterior, the cartridge does not have to withstand a high pressure difference between its interior and exterior and can be made economically.

In addition to controlling the flow of fluid into the pressure-vessel and fluid-extraction assembly 18, the valve system 14 controls the flow of: (1) purging supercritical fluid from the space between the cartridge and interior of the vessel to the collector system 16 or to a vent; and (2) the extractant from the interior of the cartridge to the collector system 16 for separate collection.

To hold sample 134 during an extraction process, the pressure-vessel and fluid-extraction assembly 18 includes a heating block 22, a pressure vessel 24 and a cartridge and plug assembly 26 with the cartridge and plug assembly 26 extending into the pressure vessel 24. The pressure vessel 24 fits within the heating block 22 for easy assembly and disassembly. With this arrangement, the heating block 22 maintains the fluids within the pressure-vessel and fluid-extraction assembly 18 at supercritical fluid temperature and pressure for proper extraction.

The cartridge and plug assembly 26 includes an extraction cartridge assembly 30, a breech plug 32 and a knob 34 which are connected together so that: (1) the pressure vessel 24 is easily sealed with the breech plug 32; (2) the extraction cartridge assembly 30 snaps onto the breech plug 32 and the assembly may be carried by the knob 34; and (3) the knob 34 serves as a handle to insert and fasten the assembly to the tube pressure vessel with the extraction tube communicating with an outlet aligned with its axis and an inlet for the space between the internal walls of the pressure vessel 24 and the exterior of the extraction cartridge 30 and for the interior of the extraction cartridge 30 being provided through a groove circumscribing the assembly inside the pressure vessel 24.

With this arrangement the extraction cartridge assembly 30 may be easily sealed in the pressure vessel 24 by threading the breech plug 32 into it and may be easily removed by unthreading the breech plug 32 and lifting the knob 34. The extraction cartridge assembly 30 contains a hollow interior, an inlet and an outlet so that a sample to be extracted may be placed in the hollow interior and supercritical fluid passed through the inlet, the hollow interior and to the outlet to a collector. The extraction cartridge assembly 30 serves as an extraction chamber or tube, the pressure vessel 24 serves as an extraction vessel and the heating block 22 serves as an oven as these terms are commonly used in the prior art.

In the preferred embodiment, the knob 34 is of a low heat conductivity material and it should include in all embodiments at least a heat insulative thermal barrier located to reduce heating of the handle portion of the knob 34. It extends outside of the pressure vessel 24 and is adapted to aid in the sealing of the pressure vessel 24 and the breech plug 32 together so that the extraction cartridge assembly 30 is within the pressure vessel 24 for maintaining it at the appropriate temperature and the knob 34 is outside the pressure vessel 24 so as to remain cool enough to handle.

Although, in the preferred embodiment, the knob 34 is a heat insulative material, it only needs to be insulated against heat conducted from the interior of the pressure vessel 24 and this may also be done by a thermal barrier separating the pressure vessel 24 from the knob 34 such as an insulative disc having a width of at least 1 millimeter and extending across the cross-section of the knob 34 to the extent of at least 80 percent of the cross-section to effectively block any considerable amount of transfer of heat between the cartridge and the knob 34. It should have a heat conductivity no greater than 0.05 calories/cm. sec. degree C at 30 degrees Centigrade.

The extraction cartridge assembly 30 has an opening which permits some supercritical fluid to enter the pressure vessel 24 to follow one path passing into the extraction tube and out through an outlet of the extraction tube into a conduit leading to a collector. Other supercritical fluid follows a second path around the outside of the cartridge to remove contaminants from the pressure vessel 24, equalize pressure and flow from another outlet. One of the inlet and outlet of the extraction cartridge assembly 30 enters along the central axis of the extraction cartridge assembly 30 and the other from the side to permit rotation of parts with respect to each other during seating of the pressure vessel 24 and yet permit communication of the extraction cartridge assembly 30 with the fluid source and with the collector. To reduce wasted heat and fluid, the space between the outside of the cartridge and the inside walls of the pressure vessel 24 is only large enough to accommodate the flow of purging fluid and to equalize pressure between the inside and outside of the cartridge. The volume between the outside of the cartridge and the inside of the pressure vessel 24 is less than 10 cubic centimeters.

In the preferred embodiment, the inlet opens into an annular space between the internal wall of the pressure vessel 24 and the cartridge and plug assembly 26. The fluid follows two paths from the annular space, both of which include an annular manifold with narrow holes and a passageway that communicates with the recess in the breech plug 32. One path opens into the extraction cartridge assembly 30. The other passes alone the narrow space outside the extraction cartridge assembly 30. Thus, supercritical fluid enters the extraction tube through a labrythian like path and at the same time passes outside the extraction tube so that the pressure inside the extraction tube is always substantially the same as that inside the pressure vessel 24. Because the pressures are substantially the same, the tube itself may be formed of relatively inexpensive plastics notwithstanding that a high pressure is desirable for extraction from the sample within the extraction tube.

The pressure vessel 24 is generally formed of strong material such as metal and is shaped as a container with an open top, an inlet opening and two outlet openings. The inlet opening is sized to receive an inlet fitting 42, the inlet fitting 42 being shown in FIG. 1 connected in series with check valve 60A to corresponding heat exchanger 40. Each of the two outlet openings are sized to receive a different one of a corresponding purge valve fitting 44, and a corresponding extractant fluid fitting 46. With these fittings, the pressure vessel 24 is able to receive the cartridge and plug assembly 26 in its open end and permit communication between the cartridge and the extractant fluid fittings, such as shown at 46. The inlet fittings, such as shown at 42, and purge valve fitting, such as 44, permit communication with the inside of the pressure vessel 24.

To control the flow of fluids to and from the pressure vessel and fluid-extraction assembly 18, the valve system 14 includes an extractant valve 50, a purge fluid valve 52 and an extracting fluid valve 54.

To introduce extracting fluid into the pressure vessel and fluid-extraction assembly 18, the extracting fluid valve 54 communicates with one branch of the tee joint 20 through tube 56 and with one end of the heat exchanger 40 through tube 58, the other end of the heat exchanger 40 communicating with the inlet fitting 42 through tube 60, check valve 60A and tube 60B. With these connections, the extracting fluid valve 54 controls the flow of fluid from the pumping system 12 through the heat exchanger 40 and the pressure vessel 24 through the inlet fitting 42.

To remove purge fluid from the pressure vessel 24, the purge fluid valve 52 communicates at one port with the purge valve fitting 44 through tube 62 and with its other port through tube 64 (not shown in FIG. 1) with the collector system 16 or with a vent (not shown) to remove fluid containing contaminants from the exterior of fluid extraction cartridge assembly 30 and the interior of the pressure vessel 24.

To remove extractant from the extraction cartridge assembly 30, the extractant valve 50 communicates at one of its ports through tube 66 with the extractant fluid fitting 46 and through its other port with the collector system 16 through tube 68 for the collecting of the extracted material, sometimes referred to as analyte or extractant, from the sample within the pressure vessel and fluid-extraction assembly 18.

For convenience, the valves 52 and 54 are mounted to be operated by a single manual control knob 70. To supply fluid to the valve system 14: (1) the tube 56 carries pressurized fluid from the pumping system 12 to tee joint 20; (2) tube 76 is connected to one arm of tee joint 20 to carry pressurized fluid to another liquid extraction system unit not shown on FIG. 1; and (3) the remaining arm of the tee joint 20 is connected through the tube 56 to an inlet fitting 74 of extracting fluid valve 54. The valves 50, 52 and 54 are, in the preferred embodiment, SSi type 02-0120.

The extracting fluid valve 54 has a rotary control shaft 80 that is rotated to open and close its internal port. This shaft is operated by hand control knob 70 and carries spur gear 82 pinned to the control shaft 80. Spur gear 84, which is pinned to control shaft 107 of purge fluid valve 52, meshes with spur gear 82 so that when control knob 70 is rotated clockwise, extracting fluid valve 54 is closed, but since the control shaft 107 of purge fluid valve 52 is geared to turn in the opposite direction, the clockwise rotation of knob 70 opens purge fluid valve 52.

The relative locations of the two gears on the two shafts are such that, in the first (clockwise) position of the knob 70, the extracting fluid valve 54 is shut and the purge fluid valve 52 is open. Turning the control knob 70 counterclockwise 130 degrees from this first position opens extraction fluid valve 54 while allowing purge fluid valve 52 to remain open. Thus, both valves are open when the knob 70 is rotated 130 degrees counterclockwise from the first position. When the knob 70 is rotated 260 degrees counterclockwise from the first position, extraction fluid valve 54 is open and purge fluid valve 52 is shut. Thus, there are three definable positions for control knob 70: (1) clockwise with valve 54 shut and valve 52 open; (2) mid position with both valves open; and (3) full counterclockwise with valve 54 open and valve 52 shut.

The extractant valve 50 includes an inlet fitting 120, outlet fitting 122, manual control knob 132 and control shaft 126. The rotary control shaft 126 is attached to control knob 132. When the extractant valve 50 is opened by turning the control knob 132 counterclockwise from its closed position, fluid flows from the extraction cartridge assembly 30, through the extractant fluid fitting 46, the conduit 66, the valve inlet fitting 120, the outlet fitting 122, through the tube 68 and into the collector system 16.

The collector system 16 includes a purge coupling 90, a purge fluid collector 92, an extractant coupling 94, an analyzing instrument 96, and an extractant fluid collector 98. The purge fluid flowing through the valve 52, flows through purge coupling 90 into the capillary tube 110 and from there into the purge fluid collector 92 where it flows into a solvent 100. Similarly, the extractant flowing through valve 50 flows through tube 68 to the extractant coupling 94 and from there to the capillary tube 128 and extractant fluid collector 98 which contains an appropriate solvent 104 in the preferred embodiment.

The analyzing instrument 96 may be coupled to the capillary tube 128 through an optical coupling 102 in a manner known in the art. The optical coupling 102 is a photodetector and light source on opposite sides of a portion of the capillary tube 128, which portion has been modified to pass light. This instrument 96 monitors extractant and may provide an indication of its passing into the extractant fluid collector 98 and information about its light absorbance. Other analytical instruments may also be used to identify or indicate other characteristics of the extractant.

Figure 2:
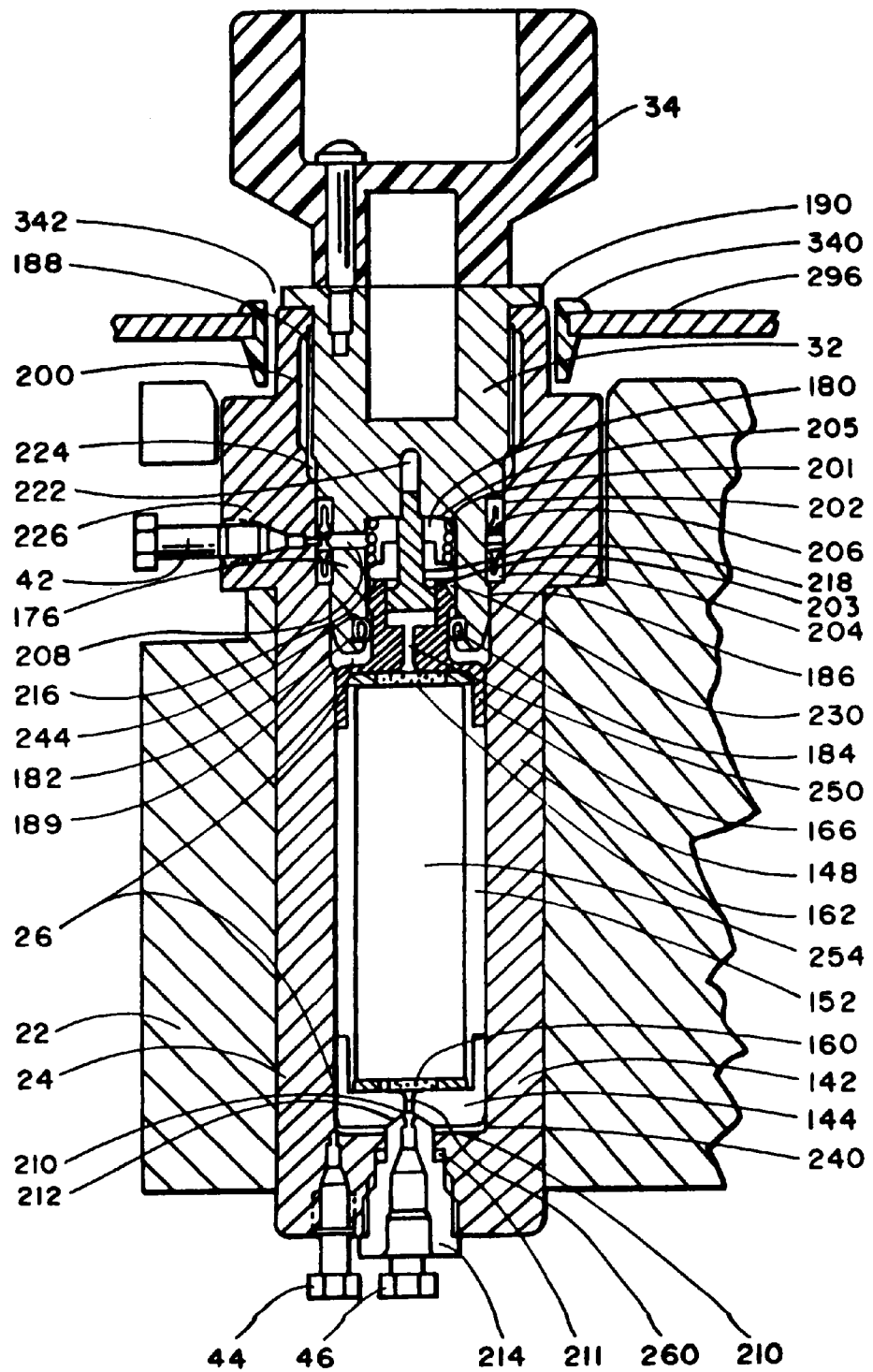
FIG. 2 is a fragmentary sectional view of the extraction cartridge, breech plug pressure vessel and heating block.

In FIG. 2, there is shown a sectional view of the clipped-together extraction cartridge 26, knob 34 and breech plug 32 replaceably installed in pressure vessel 24 which in turn has previously been permanently force fit into heating block 22. The pressure vessel 24 is fabricated of type 303 stainless steel for good machinability and corrosion resistance and has within it a cylindrical central opening sized to receive the extraction cartridge 26, two openings for outlet fittings in its bottom end, an opening in its cylindrical side wall to receive an inlet fitting and an open top with internal threads sized to engage the external threads 188 of the breech plug 32. The heating block 22 is fabricated from aluminum for good thermal conductivity and includes a cylindrical opening sized to tightly receive the pressure vessel 24. The breech plug 32 and the extraction cartridge assembly 30 are a slip fit within the pressure vessel 24. External threads 188 on breech plug 32 engage in internal threads 200 within pressure vessel 24.

An annular self-acting high pressure seal 202 cooperates with a sealing surface 186 to seal high pressure supercritical fluid from the atmosphere and an annular low pressure seal 204 spaced from the annular high pressure seal 202 prevents contaminated supercritical fluid in the space between the interior of the pressure vessel 24 and the exterior of the extraction cartridge assembly 30 from getting back to the supercritical fluid supply. These two annular seals 202 and 204 form between them a torroidal inlet chamber into which the outlet of the fluid inlet 42 extends to introduce fluid. Contamination may arise from fingerprints or other foreign material on the outside wall of extraction cartridge assembly 30 and the low pressure seal 204 protects against this contamination. Seals 202 and 204 are Bal-Seal type 504MB-118-GFP.

Supercritical fluid is supplied to fluid inlet 42 and circulates in the annular space between high pressure seal 202 and low pressure seal 204, and then follows two paths into the pressure vessel 24 and extraction cartridge 30: one path for purging and one path for extraction. An annular spacer 206 within the torroidal opening between seals 202 and 204 has an hour-glass shaped cross section with radial holes through it and distributes incoming supercritical fluid from the inlet of fitting 42 to the opposite side of the spacer 206 from which it flows to passageway 208 drilled in breech plug 32.

Because the passageway 208 extends radially from the recess 180 in the breech plug 32 to the annular ring, it provides an open path for fluid between the two regardless of the orientation of passageway 208. The passageway 208 opens at an uncontrolled angular location with respect to the inlet fixture 42 (inner side). Fluid flows from one side of the inwardly curved portion of the hour glass shaped spacer 206 that communicates with the outlet of fitting 42 to the other side of the inwardly curved portion and from there to the passageway 208.

When the cartridge and plug assembly 26 are inserted into the pressure vessel 24 as shown in FIG. 2, the knob 34 is rotated and the external threads 188 of the breech plug 32 which form an eight thread per inch connector engage internal threads 200 in the pressure vessel 24, screwing the breech plug 32 and attached cartridge and plug assembly 26 down into the pressure vessel 24. When conical recess 210 in the bottom cap 144 reaches the external conical tip 212 of fitting adapter 214, the cartridge and plug assembly 26 is prevented from moving further down.

Screwing the breech plug 32 in further after the cartridge and plug assembly 26 has bottomed causes the upper flat annular surface of fitting nipple 176 to bear upon the flat lower surface of a hat-shaped washer 216. At this time, the hat-shaped washer 216 is residing against the upper surface of the head of a shoulder screw 218 which is threaded into cylindrical hole 222 in breech plug 32.

Further screwing of the breech plug 32 into the pressure vessel 24 causes the nipple 176 to lift the washer 216 off of the screw head and compress a coil spring 201 between annular surface 205 and the ridge of the washer 216. Continued screwing of the breech plug 32 into the pressure vessel 24 causes annular flange 190 of breech plug 32 to bear upon the upper surface of the pressure vessel 24. This provides a limit stop with the coil spring 201 compressed, as shown in FIG. 2.

The force of the compression spring 201 is enough to provide a low pressure seal between the hat-shaped washer 216 and the upper annular surface 203 of the fitting nipple 176. More importantly, this force also provides a low pressure seal on the mating concical surfaces of the recess 210 of lower cap 144 and the external conical tip 212 of the fitting adapter 214.

The sealing surface 186 acts as a pilot during the initial part of insertion to insure that the internal threads 188 do not get cross-threaded. A taper 189 at the end of the cylindrical sealing surface 186 pilots the breech plug 32 past seals 202 and 204 so that they are not damaged during insertion of the breech plug 32.

The locations of recess 224, passageway 208, high pressure seal 202 and the engaging threads 188 and 200 are chosen such that if the breech plug 32 is inadvertently removed when the interior of the pressure vessel 24 is pressurized, fluid within the pressure vessel 24 leaks past high pressure seal 202 and runs up the flights of the engaging screw threads 188 and 200, and depressurizes the system while there is still adequate screw engagement to ensure safety at the maximum rated operating pressure. The maximum rated operating pressure of the embodiment shown in FIG. 2 is 10,000 psi. The maximum operating temperature is 150 degrees Centigrade. The equipment need not be designed for operating temperatures above 300 degrees Centigrade and pressure above 30,000 pounds per square inch.

After the breech plug 32 and the cartridge and plug assembly 26 are assembled into the pressure vessel 24 as described above, but before an extraction, the space between the cartridge and plug assembly 26 and the pressure vessel 24 is purged of contaminants. During such a purge or cleaning cycle supercritical fluid enters fluid inlet 42, is distributed by the annular spacer 206 and goes through passageway 208. It passes between the outer diameter of hat-shaped washer 216 and the inside cylindrical diameter 230 of the recess within breech plug 32. Fluid then continues down and passes the annular space between the outside diameter of engaging nipple 176 and inside diameter 230 of the recess 180 in breech plug 32. The fluid passes garter spring 184 and circulates with even circumferential distribution around the outside of top cap 148, the extraction tube 152, and the bottom cap 144. The flow is collected in the annular space below the bottom cap 144 and above the bottom 240 of pressure vessel 24 and exits through vent discharge fitting 44, carrying contaminants with it.

Contaminated fluid between the exterior of extraction cartridge 26 and the interior of high pressure vessel 24 does not make its way into the interior of the extraction vessel. Low pressure seal 204 prevents contaminated fluid from reaching passageway 208. A labyrinth seal consisting of the narrow gaps between the major diameter of fitting nipple 176 and the inside diameter 230 of recess 180, and between inside diameter 230 and the outside diameter of the hat-shaped washer 216, prevents contaminants from reaching the space above the hat-shaped washer 216 by diffusion.

During a purge or cleaning cycle, there is downward flow of supercritical fluid through these gaps, and since the gaps are small, this downward fluid flow prevents eddies of contaminated fluid from passing up through the gaps. These gaps are only a few thousandths of an inch. Because the top of nipple 176 and the conical recess 210 at the bottom of the extraction cartridge are sealed by spring pressure, contamination cannot enter in these ways.

For extraction, supercritical fluid entering fitting 42 is distributed in the space occupied by spacer ring 206, flows through passageway 208 and flows down the few thousandths of an inch radial gap between the shoulder of shoulder screw 218 and the inside diameter of washer 216. The fluid continues to flow down and flows through passageway 250, porous frit 162 and into extraction volume 254 where it passes through material to be extracted. Extraction volume 254 is shown sized in FIG. 2 for a 10 cubic centimeter volume to receive sample. After passing the extraction volume fluid, it is exhausted for sample collection through frit 160, passageway 260, fitting adapter 214 and out through fitting 46.

All tubing, except tubing designated as capillary tubing, in this disclosure is 300 series stainless steel with an outside diameter of 1/16 inch and inside diameter 0.02 inch.

In operation after assembly, the fluid flow associated directly with the pure fluid valve 54 (FIG. 1) exiting its port 114 (FIG. 1) flows through tube 58 through the heat exchanger 40, which is formed by coiling a contiguous segment of tubing into a helix, through the check valve 60A and through the tube 60B to the inlet fitting 42 of pressure vessel 24. The heat exchanger 40 actually resides in a longitudinal bore through heating block 22 so that the heat exchanger is at the same temperature as pressure vessel 24 and extraction tube 30. This preheats any fluid flowing into inlet fitting 42 to essentially the same temperature as the extraction cartridge assembly 30. This temperature is above the critical temperature for the fluid. Assuming that the pump 12 is set to produce a constant fluid pressure greater than the critical pressure, fluid entering the pressure vessel 24 will be a supercritical fluid.

The check valve 60A prevents backflow of supercritical fluid out of the pressure vessel 24 and extraction cartridge 26 of a first channel of a dual channel supercritical extraction system if there is a momentary drop in pressure of the supercritical fluid at the location of the tee 20. Such a pressure fluctuation could occur if the second channel of a dual channel extraction system is suddenly purged while the first channel is extracting. Each channel requires such a check valve.

During a purge cycle, contaminated supercritical fluid leaves fitting 44, flows through a tube 62 and enters the inlet fitting 116 of the purge fluid valve 52. Then it exits the outlet fitting 118 and passes through the tube 64 to the coupling 90 (FIG. 1). The coupling 90 couples the quartz capillary tube 110 so that contaminated purge gas exits through it. The bore of the capillary tube is small enough, such as 75 micrometers, and its length long enough, on the order of a few inches, to provide enough fluid resistance to limit the flow to a convenient rate: for example 5 milliliters per minute with respect to displacement of pump 12, at a pressure of 3,000 psi. Pump 12 is a constant pressure pump so this fluid flow does not affect the pressure within pressure vessel 24 once the flow stabilizes.

The outer end of capillary 110 may be immersed a purge fluid collector 92 (FIG. 1) containing an appropriate solvent 100 such as isopropyl alcohol to serve as a collector. Bubbles through this solvent indicate proper flow and the solvent tends to prevent the end of the capillary tube 110 from being plugged by the exhausted contaminants. A solvent is chosen in a manner known in the art to dissolve contaminants so the end of the capillary tube 110 does not plug and so the solvent may later be analyzed if desired to determine whether there was any contaminants on the exterior of the extraction cartridge.

During an extraction cycle, extractant exits fitting 46 on pressure vessel 24 and passes through tube 66. This tubing extends to inlet fitting 120 of extractant valve 50 which has rotary control shaft 126 attached to control knob 132. When the extractant valve 50 is opened by turning it counterclockwise from its closed position, fluid exits from its fitting 122, through tube 68 to fitting 94. Fitting 94 couples to quartz capillary tube 128.

Capillary tube 128 has a small enough bore, such as 50 micrometers, and a long enough length, on the order of several inches, to produce a flow rate, relative to the displacement of constant pressure pump 12, of a convenient amount. For example, this may be two milliliters per minute. The end of the capillary tube 128 dips into solvent 104 in the extractant collector 98.

Isopropyl alcohol is under some circumstances used for solvent 104. This solvent 104 must be a good solvent for the extractant since it must trap the extractant by dissolving it from the gas bubbling through it and must prevent plugging at the end of the capillary tube 128.

The solvent 104 is removed after extraction and is analyzed to determine the composition and amount of the extractant. Because of the pressure and temperature drop along the length of capillary 128 (and also capillary 110) fluid entering the capillary as a supercritical fluid (or a liquid if fitting 90 or fitting 94 is not heated) changes to a gas by the time it reaches the far end where it dips into the solvent which is at room temperature.

Before using the extraction system 10, the pump 12 is set to the desired pressure and the heater block 22 is set to the desired temperature. The bottom cap 144 (FIG. 2) with the frit 160 is screwed onto the bottom of extraction tube 152. The internal cavity 158 is then filled or partly filled with sample to be extracted. The frit 162 and top cap 174 are then screwed on to the top of extraction tube 152 forming the cartridge and plug assembly 26. The cartridge and plug assembly 26 is then clipped into breech plug 32 by shoving the fitting nipple 176 on the extraction cartridge past garter spring 184 located within breech plug 32. Knob 70 is set to the vent position closing valve 54 and opening valve 52 (FIG. 1). Valve 124 is set to the clockwise closed position.

The assembled breech plug and extraction cartridge are inserted into preheated pressure vessel 22 and manually screwed with knob 34 into pressure vessel 24 until annular flange 190 contacts the top of pressure vessel 24 (FIG. 2). The pressure vessel has been preheated under control of a thermocouple temperature controller to the desired temperature. The cartridge and plug assembly 26 within pressure vessel 24 rapidly rises to the required temperature.

After insertion of the cartridge and plug assembly 26 into the sample block 24, valve knob 70 is rotated to the purge position. In this position, both valves 54 and 52 are open. Since the pump 12 has already been set to the desired fluid pressure, fluid flows through tubes 76, 56, valve 54, tube 58, heat exchanger 40, tube 60, check valves 60A and 60B and inlet fitting 42 into the cavity 180. Since valve 124 is closed, supercritical fluid preheated to the correct temperature by heat exchanger 40, flows past hat-shaped washer 216, fitting nipple 176 and around the outside of cartridge and plug assembly 26. This supercritical fluid dissolves any contaminants on the outside of extraction cartridge assembly 30 and any contaminants inside pressure vessel 24. The hot supercritical fluid also insures that the extraction cartridge assembly 30 is at the proper operating temperature. The supercritical fluid flushes the contaminants from fitting 44, through tube 62, valve 52, tube 64, the fitting 90 and the capillary tube 110.

After a short purge cycle, control knob 70 is set to the extract position. This sets valves 54 and 52 so that valve 54 is open and valve 52 is closed. Immediately after making this setting, the operator opens valve 124 by rotating knob 132 counterclockwise in the extract direction. Pressurized fluid flows through valve 54 into heat exchanger 40 so that it is at the desired supercritical temperature, and flows into fitting 42. It then flows into cavity 180 and past the annular space between shoulder screw 218 and the inside diameter of hat-shaped washer 216, after which it passes through the interior of fitting nipple 176, through passageway 250 and into the extraction vessel 26. This supercritical fluid flowing through the interior sample cavity 254 of the extraction cartridge extracts analyte from the sample 134 contained within the cavity 254.

Supercritical fluid with the analyte in solution passes out through the fitting 46, the tube 66, the valve 124, the tube 68, the coupling 94 and the capillary tube 128 which leads into the collecting solvent 104 within test tube 98. The analyte is dissolved in the solvent 104 for later analysis. When the extraction is complete, knob 132 is rotated clockwise in the closed direction, closing valve 124. This stops the flow of supercritical fluid into the extraction cartridge 26. Knob 70 is then rotated clockwise to the vent position. This closes valve 54 and opens valve 52, depressurizing the pressure vessel 24 and cartridge and plug assembly 26 through capillary tube 110. When bubbles stop issuing through the end of capillary tube 110, depressurization is complete. Knob 34 is rotated counterclockwise to unscrew the breech plug 32 and the attached cartridge and plug assembly 26 from pressure vessel 24. Extraction cartridge assembly 30 may now be open to empty spent sample.

Figure 3:
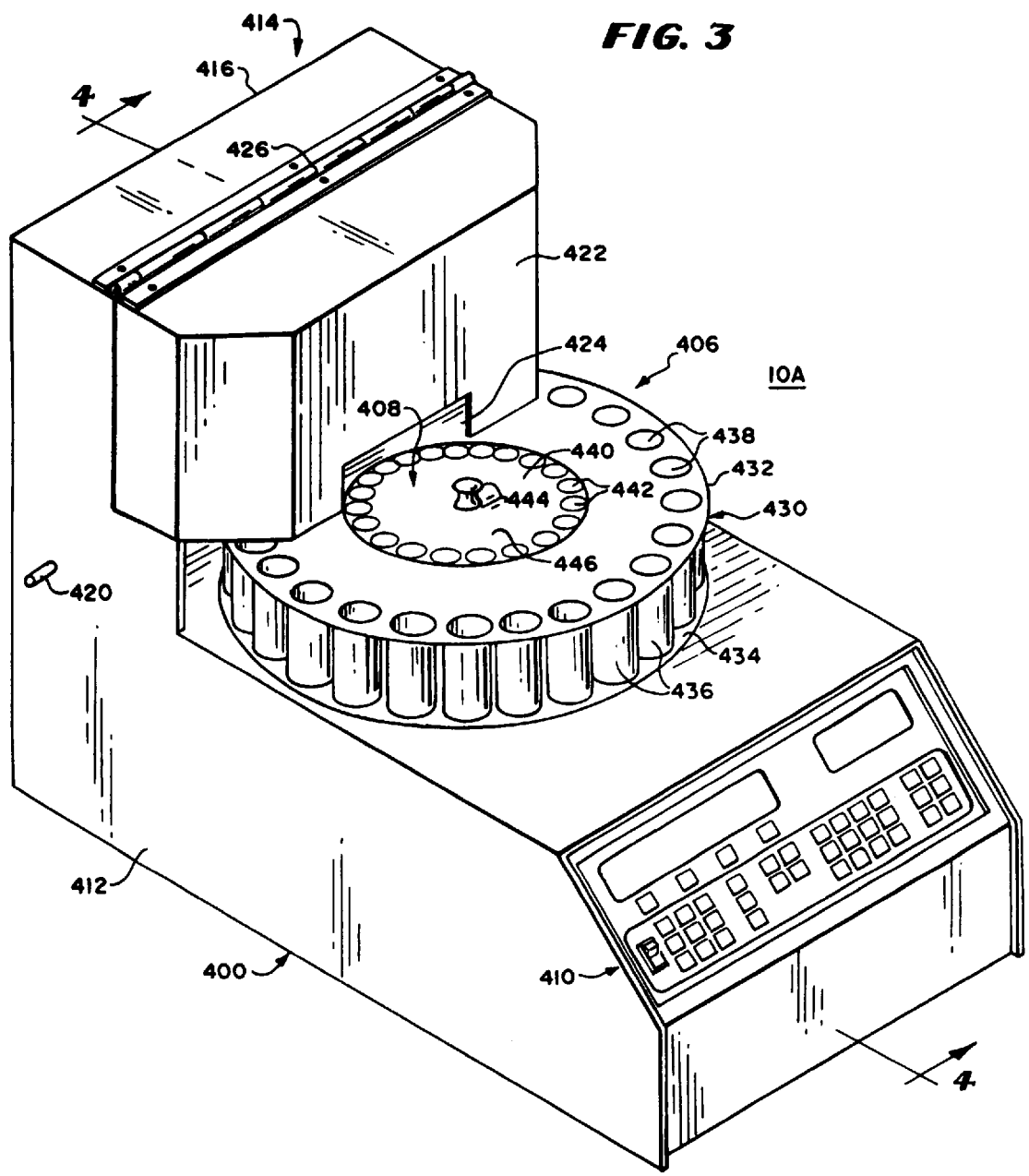
FIG. 3 is a perspective view of another embodiment of the invention capable of automatic extraction of a series of samples.

In FIG. 3, there is shown a simplified perspective view of another embodiment 10A of supercritical fluid extraction system having a cabinet 400 containing a drive section in its lower portion (not shown in FIG. 3), an extraction section in the upper portion of the cabinet (not shown in FIG. 3), a sample injection section 406 and a fraction collection section 408. The supercritical liquid extraction system 10A is controlled from a panel 410 on the front of the cabinet 400 and the drive section operates the extraction section, the sample injection section 406, and the fraction collection section 408, which cooperate together to extract a plurality of samples sequentially and collect the extractant from the samples in separate containers with minimum intervention by an operator.

The liquid extraction system in the embodiment 10A operates in a manner similar to that of the embodiment of FIG. 1 but is adapted to cooperate with the novel sample injector and fraction collector. With this arrangement, a series of samples to be extracted are preloaded into a means for holding the samples and the samples are automatically injected one at a time into the extractor. In the extractor, supercritical fluid is supplied to the samples and an extractant is removed from the samples one by one. To aid in correlating the embodiment 10 and the embodiment 10A, similar parts have the same reference numerals but in the embodiment of FIG. 10A, the numerals include the suffix "A".

The extractant is supplied to individual containers or individual compartments of one container in a fraction collector. Thus, a plurality of extractions are performed on a plurality of different preloaded samples without the need for manually loading samples or initiating the flow of the supercritical fluid for each individual sample. The samples are automatically mechanically moved one by one into the extractor for extraction instead of being individually physically injected by an operator.

The cabinet 400 has a lower portion 412 generally shaped as a right regular parallelopiped with an angled control panel 410 and upstanding upper portion 414 which is another right regular parallelopiped extending upwardly to create a profile substantially shaped as an "L" having a common back portion or rear panel 416 which may contain fans and connections for supplementary pumps and the like. A fluid fitting 420 extends from one side to permit near supercritical fluids to be introduced into the cabinet 400. The L-profiled cabinet 400 has an angled front panel 410 for convenient use of controls and a top surface on the foot of the "L" for manipulation of samples to be injected and extractants that are collected.

To permit access to the interior of the cabinet 400, the upper portion 414 includes a hinged front access panel 422 having hinges 426 at its top so that it can be pivoted upwardly. It includes an opening 424 near its bottom to permit the entrance of fraction collector receptacles that are relatively tall. It extends downwardly to a point spaced from the top surface of the lower portion 412 of the cabinet 400 a sufficient distance to permit the entrance of normal receptacles used in the sample injector and the fraction collector.

The sample injection section 406 includes a sample reel 430 which is formed of upper and lower rotatable plates 432 and 434 spaced vertically from each other and containing holes in the upper plate 432 and openings in the lower plate 434 which receive cylindrical tubular sleeves 436 having vertical longitudinal axes and open ends. The upper open end 438 permits samples to be received and to be removed as the sample reel 430 is rotated into the extractor.

With this arrangement, the sample reel 430 may be rotated to move samples one by one into the extractor for processing. The sample reel 430 is horizontal and extends into the upper portion 414 of the cabinet 400 and into the extractor assembly with its vertical center of rotation being outside of the upper portion 414 to permit ready access to a number of the sleeves 436 by users and yet to permit sequential rotation by automatic means into the extractor. In the preferred embodiment, there are 24 sleeves for containing 24 distinctly different samples which can, without human intervention, be moved into the extractor.

To receive extractant, the fraction collection section 408 includes a horizontal fraction collector reel 440 mounted concentrically with the sample reel 430 but having a smaller diameter to be inside the sample reel 430 having a plurality of openings 442 circularly arranged in spaced apart relationship with each other about the periphery of a top plate 446 of the fraction collector reel 440 and having in its center a knob 444 by which the fraction collector reel 440 may be lifted and removed from the cabinet 400. With this arrangement, the fraction collector reel 440 may be lifted and removed or reinserted after the hinged access panel 422 is pivoted upwardly about the hinges 426.

When the fraction collector reel 440 is in place, it is rotated automatically through the opening 424 into a location in which one or more individual containers 442 may receive extractant. The fraction collector reel 440 is moved alternately with the sample reel 430 and independently of it so that, after a sample injection and extraction, one or more of the openings 442 are moved into position to receive the extractant prior to the injection of another sample for extraction.

Because the reels 430 and 440 rotate within the upper portion 414 of the cabinet 400 with a portion of its periphery outside of the cabinet 400, the collected extractant may be removed and new sample added during operation of the equipment. For this purpose, the receptacles for the fractions and the receptacles for the samples have upward open ends and are mounted with their axes vertical.

Figure 4:
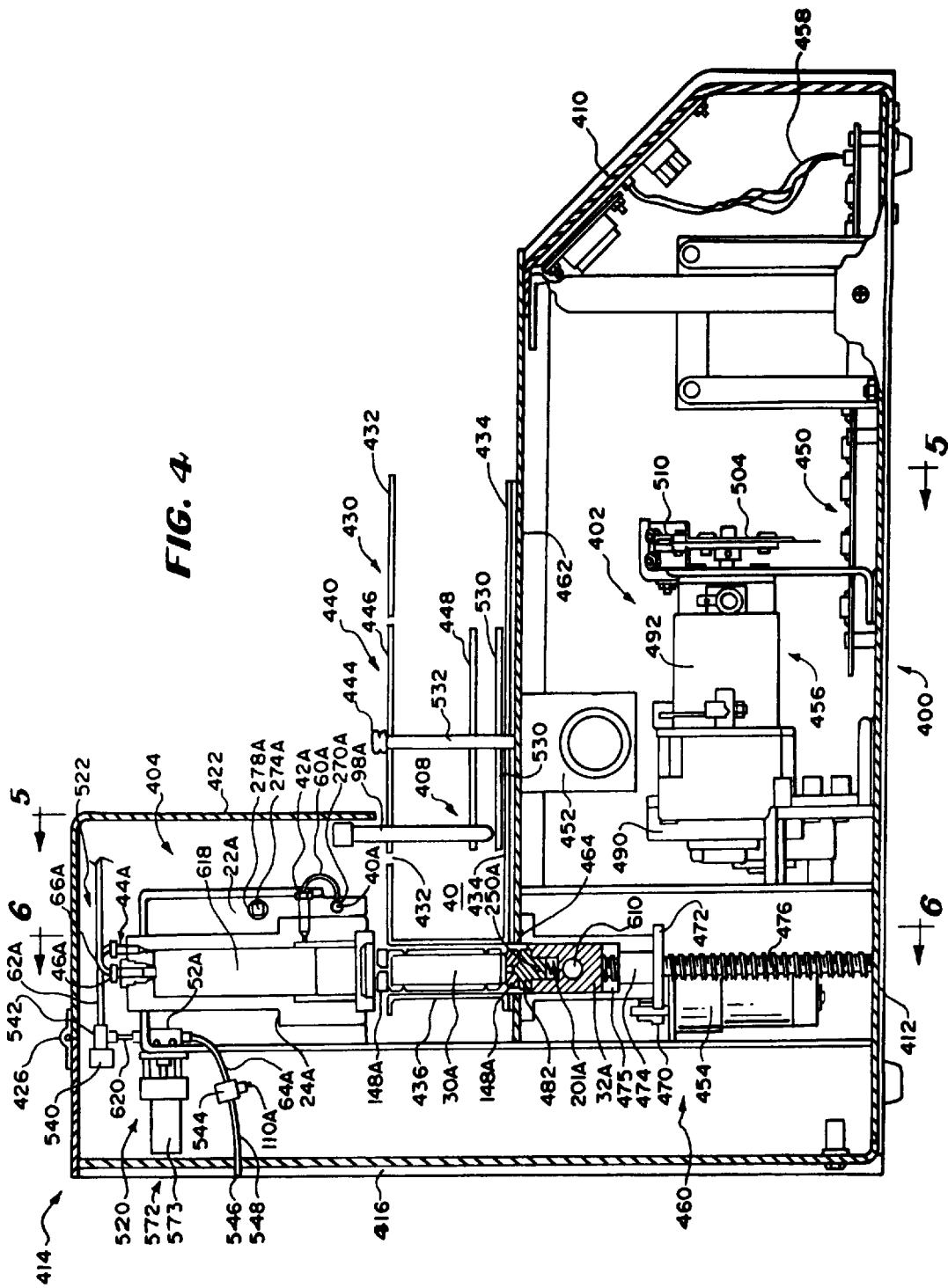
FIG. 4 is a sectional view taken through lines 4—4 of FIG. 3.

In FIG. 4, there is shown a longitudinal sectional view through lines 4—4 of FIG. 3 showing the cabinet 400, the drive section 402 within the cabinet 400, the extraction section 404, the sample injection section 406 and the fraction collection section 408. The drive section 402 includes a control system 450, a sample-and-extractant container reel drive assembly 452, a sample injector drive 454 and a fluid drive or pump 456. The control system 450 receives information from the control panel 410 and conveys information to it through a cable 458. It also controls the pump 456, the sample-and-extractant container reel drive assembly 452 and the sample injector drive 454, which cooperate together to move samples into position, inject them into the extractor, pump fluids through the extractor to extract the samples and collect the samples in sequence one by one.

To inject samples into the extraction section 404, the sample injection section 406 includes the sample-and-extractant container reel drive assembly 452, the sample reel assembly 430, and a cartridge injector assembly 460. The sample-and-extractant container reel drive assembly 452 drives the sample reel assembly 430 to carry a cartridge assembly 30A onto the cartridge injector assembly 460 which lifts it under the control of the sample injector drive 454 upwardly into a pressure vessel 24A for the purpose of extracting a sample within the cartridge assembly 30A. The cartridge assembly 30A and the pressure vessel 24A are similar to the cartridge assembly 30 and pressure vessel 24 of the embodiment of FIGS. 1–14 and are only adapted such as by having their top and bottom sides reversed to permit the cartridge assembly 30A to be inserted from the bottom into the pressure vessel 24A and be more easily sealed therein for extraction and removed by gravity after extraction.

To drive the sample reel assembly 430, the sample-and-extractant container reel drive assembly 452 includes a central transmission and motors on each side that drive the transmission under the control of the control system 450 to drive either one or both the sample injector reel assembly 430 and the fraction collector reel 440.

The sample injector reel assembly 430 includes the top plate 432, the bottom plate 434, both of which are rotatable together to carry a plurality of sleeves 436 sequentially, one at a time, into position for the repeated injecting of cartridges one by one into the pressure vessel 24A and the removal of the cartridges from the pressure vessel 24A and the return of them to the reel assembly 430 one by one so that only one cartridge is in the pressure vessel 24A at a time.

Within the extraction section 404, a stationary bottom plate 462 has a hole 464, with the hole being aligned with the open-bottom end of the pressure vessel 24A and the upper end of the cartridge injector assembly 460. Consequently, the cartridge assemblies such as 30A are rotated one by one above the open end 464 in the bottom plate 462 for movement upwardly into the pressure vessel assembly 24A by the cartridge injector assembly 460 under the control of the sample injector drive 454 for extraction of the sample therein. With this arrangement, a stationary plate 462 holds the cartridge assemblies 30A in place as they are rotated by the upper and lower plates 432 and 434 until they are sequentially brought over the opening 464 through the stationary plate 462 for elevation into the pressure vessel 24A.

To inject cartridges into the pressure vessel 24A, the cartridge injector assembly 460 includes the sample injector drive 454, a pinion 470, a gear 472, a multi-threaded, fast action nut 474, a corresponding screw 476, and piston or plug 32A. The pinion 470 is mounted to the output shaft of the drive gear motor 454 and engages the teeth of gear 472. The gear 472 is fastened to or integrally formed with the drive nut 474 which, as it rotates, moves the screw 476 upwardly or downwardly. The support platform 475, piston or plug 32A and sample container 30A are carried by the top of the screw 476 and are moved upwardly and downwardly. The top surface of the plug 32A, which is supported by the screw 476 in its lower position is flush with the bottom of the opening 464 in the fixed plate 462 to support a cartridge such as 30A therein and in its top position positions the piston or plug 32A at the bottom of the pressure vessel 24A. Plug 32A carries self-actuated, spring-biased, cylinder seals, such as those made by the Bal-Seal Corporation. These seals provide a high pressure fluid-tight seal between the plug 32A and the inner wall of the pressure vessel 24A.

With this arrangement, the piston or plug 32A is sealable against the walls of the pressure vessel 24A during the extraction process after moving the cartridge assembly 30A upwardly into the pressure vessel 24A, and after extraction, can move the cartridge assembly 30A downwardly back to the sample reel assembly 430 for rotation out of the upper injector housing 414 as a new cartridge is moved into position for injecting into the pressure vessel 24A. A bearing mount rotatably supports the nut 474 while maintaining it in the same vertical position so as to move the rapid-advance screw or other screw 476 upwardly and downwardly.

The plug 32A serves a function similar to the breech plug 32 in the embodiment of FIGS. 1–14 and contains within it an opening supporting a spring 201A and a support block 482 so that the support block 482 is biased inwardly against the cartridge end 148A to move the cartridge 30A into place against fittings for supercritical fluid.

To extract the sample in the cartridge 30A after it has been moved into position and the breech plug 32A fastened in place for a seal, extracting fluid is applied through the fitting 42A in a manner similar to the embodiment of FIG. 1, so that the extracting fluid flows through one path into the cartridge 30A and through another path over the outside of the cartridge 30A into the fitting 44A and from there to a purge collector or vent. The extractant, after passing through the cartridge and the sample, exits from a fitting 46A and proceeds to the sample collector in a manner to be described hereinafter.

To pump fluid such as carbon dioxide into the pressure vessel 24A at a temperature proper for supercritical extraction: (1) the pump 456 includes a pump head 490 and an electrical motor 492; and (2) the pressure vessel 24A has an aluminum heating block 22A over it, an opening 278A in the aluminum heating block, a rod-shaped heating element 274A in the aperture 278A, the extracting fluid fitting 42A and a heat exchanger 40A entering the aluminum heating block 22A at aperture 270A. The motor 492 drives the pump mechanism 490 to pump fluid into the aperture 270A, through the heat exchanger 40A within the aperture 270A, through the connecting tubing 60A and the fitting 42A and into the cartridge 30A and the pressure vessel 24A. The aluminum block 22A controls the temperature of the fluid, which may be carbon dioxide or any other useful extracting fluid to keep it above the supercritical temperature for that fluid, and for that purpose, the heating rod 274A within the aperature 278A is used when necessary to heat the aluminum block 22A.

The pump 456 may be any suitable pump, but one appropriate pump for carbon dioxide is the pump used in the Isco model 2350 HPLC Pumping System sold by Isco, Inc., Lincoln, Nebr. However, for best results when using carbon dioxide, the stroke of this pump is modified from ten millimeters to fifteen millimeters, and smaller, lower trapped-volume check valves are used. These modifications increase the compression ratio of the pump from 1.7:1 to 2.6:1 and increase the displacement by a multiple of 1.5. An additional change is to use Carpenter Technologies 182FM stainless steel in the pump head, instead of type 316, for better thermal conducting. The pumphead and inlet line to the pump are preferably thermoelectrically cooled.

To collect extractants, the fraction collector section 408 includes the fraction collection reel 440, the sample-and-extractant container reel drive assembly 452, a purge fluid outlet system 520 and an extractant fluid outlet system 522. The fraction collection reel 440 moves receptacles such as 98A into position within the housing 414 where the extractant fluid outlet system, 522 to be described in greater detail hereinafter, causes fluid from the fitting 46A in the pressure vessel 24A to flow outwardly and into the receptacle 98A after piercing a seal therein. The purge fluid system 520 causes purge fluid to flow from the purge fluid fitting 44A to a pressure control unit and finally to an exhaust or collection unit.

To move the collection receptacles 98A into position, the fraction collection reel 440 includes a knob 444, an intermediate plate 448, an upper plate 446, a lower disk plate 530 and a drive rod 532. The drive rod 532 rotates within the fixed disk 530 and carries above them the upper and lower plates 446 and 448. The upper and lower plates 446 and 448 have aligned circumferentially spaced holes through them, each of which can receive a collection vial such as 98A. The lower disk 530 does not have holes and supports the plates as they are moved. The knob 444 may be used to lift the fraction collector reel 440 from the center of the sample injector reel 430 after the hinged front access panel 422 has been opened about its hinge 426.

The sample-and-extractant container reel drive assembly 452 moves the collection vials one by one inside the upper portion of the housing 414 to receive extractant. One or more such vessels 98A may be moved in place each time a sample cartridge 30A is extracted so that the receptacles 98A are moved alternatively with the sample cartridges 30A, although several receptacles 98A may be moved in the time between moving one of the sample cartridges 30A into a pressure vessel 24A and the time the sample cartridge is removed from the pressure vessel 24A. The extractant passes through fitting 46A and into the fraction collector receptacles 98A in a manner to be described hereinafter. The purge fitting 44A communicates with the extraction volume in the cartridge 30A and is connected to a Tee-joint tube 542 through tubing 62A. A second arm of the Tee-joint tube 542 is connected to an over-pressure safety diaphram 540 calibrated to burst at 12,500 pounds per square inch. This is an excess of the maximum rated working pressure of 10,000 pounds per square inch for pressure vessel 24A. The remaining arm of the Tee-joint tube 542 is connected to the purge valve 52A. The other side of the purge valve 52A is connected to the first side of a second Tee-joint tube 544 through the tube 64A. The second side of the Tee-joint tube 544 is connected to an exterior vent port 546 through a tube 548. The third arm of the Tee-joint tube 544 is connected to the exhaust tube 110A which vents the fraction collection vial 98A. With this arrangement, the purge fluid flowing through fitting 44A is removed and a tube connected to the vent port 546 is also used to vent the sample receptacle 98A in a manner to be described hereinafter.

Figure 5:
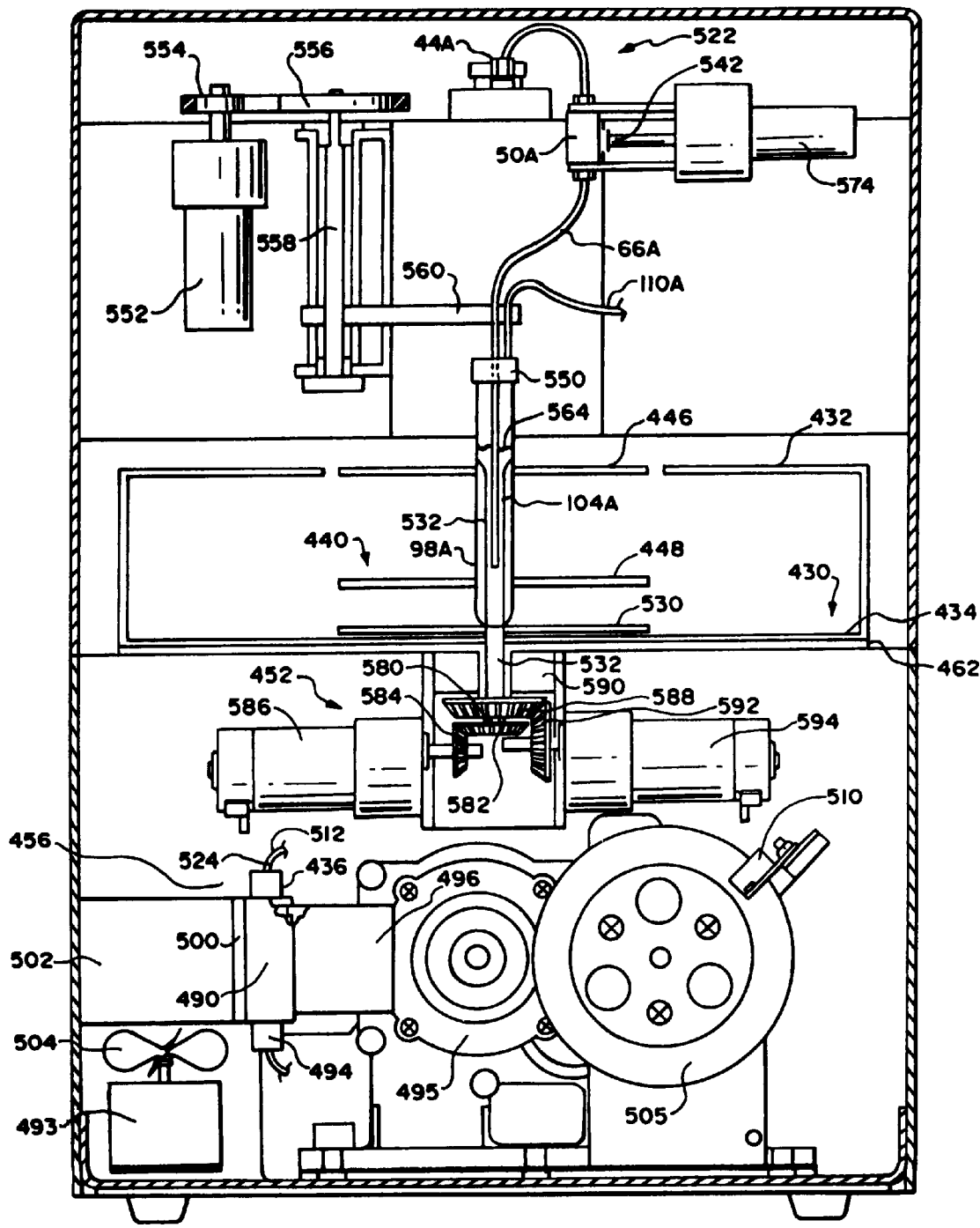
FIG. 5 is a sectional view taken through lines 5—5 of FIG. 4.

In FIG. 5, there is shown a simplified sectional elevational view of the embodiment 10A of supercritical fluid extractor taken through lines 5—5 of FIG. 4 having the sample-and-extractant container reel drive assembly 452, the pump 456 and the extractant fluid outlet system 522. The sample-and-extractant container reel drive assembly 452 may selectively move either the sample reel 430 or the fraction collection reel 440 under the control of the controller 450 (FIG. 4).

To selectively drive the fraction collection reel 440, the sample-and-extractant container reel drive assembly 452 includes a fraction collection spindle 532, a tubular shaft 580, a bevel gear 582, a bevel gear 584 and a gear motor 586. The controller 450 controls the gear motor 586 to rotate the fraction collection reel 440. For this purpose, the spindle 532 is held by the tubular shaft 580. The bevel gear 582 is fastened at the end of the spindle 532 and meshes with the bevel gear 584 on gear motor 586. The controller 450 moves these gears into meshing position and causes the motor 586 to rotate its output shaft so as to drive the collection reel 440 (FIGS. 15 and 16) and not the sample injector reel 430 (FIGS. 3 and 4).

To move the sample injector reel 430, the sample-and-extractant container reel drive assembly 452 includes the tubular shaft 580 supported by bearing block 590, fraction collection spindle 532, bevel gear 588, bevel gear 592 and gear motor 594. The controller 450 actuates gear motor 594 to cause the bevel gear 592 to rotate. The bevel gear 592 meshes with the bevel gear 588 which is attached to the bottom end of the fraction collection spindle 532.

To cause extractant to flow into the fraction collection vial 98A, the extractant fluid outlet system 522 includes a gear motor 552, a pinion 554, a gear 556, a lead screw 558, an arm 560, and a restrictor tube 66A. The vials 98A have a seal 550 over the top, which seal can be pierced.

To cause the seal 550 to be pierced and extractant to flow into the vial 98A, the controller 450 starts the gear motor 552 which rotates its pinion 554 which is in engagement with the gear 556. The pinion 554 rotates the gear 556, which engages and is fastened to the rotating lead screw 558. The arm 560 is mounted for movement by the lead screw 558 and lowers it into a position where the restrictor tube 66A pierces the cap 550 on the collection vial 98A and moves its tip below the surface 564 of the collection fluid within the vial 98A. As the extractant flows into the tube, exhaust is removed from the tube through an exhaust tube 110A (FIG. 4 in addition to FIG. 5).

If either the tube 66A or the tube 110A are stiff or otherwise inconvenient to bend, it is advantageous to raise the collecting vial 98A up to tubes 66A and 110A, instead of lowering the tubes into the collecting vial. This alternate arrangement does not pose any difficulty as the collecting vial 98A may be raised by a support similar to plug 32A, which support is connected directly to plug 32A so that it moves synchronously with plug 32A.

With either arrangement, extractant flows through the fitting 46A (FIG. 4) from the sample cartridge 30A (FIG. 4) through the tubing 522 (FIG. 4), the valve 50A and the restrictor tube 66A. Extractant residing in bubbles from the tube are captured through trapping fluid 104A whereby extractant is trapped in the trapping fluid 104 in the vial 98A and extracting fluid passes out through the exhaust tube 110A, Tee-joint tube 544 (FIG. 4), tube 66A and exhaust port 546 (FIG. 4). After collection of the extractant, the motor 552 moves in the reverse direction and raises arm 560 which removes the restrictor tube 66A and exhaust tube 110A from the vial 98A.

Because the pump head 490 is heated by pumping at high compression, both the pump head 490 and incoming fluid line are preferably cooled. In the preferred embodiment, they are cooled thermoelectrically (Peltier effect). The pump head 490, the inlet check valve housing 494 are formed of Carpenter 182FM stainless steel rather than type 316 stainless steel to increase their thermal conductivity.

In pumping, the pump drive motor 492 (FIG. 4) drives a cam within cam housing 495 through appropriate gear train within the gear housing 496. The rotating cam within the cam housing 495 operates a pump plunger which cooperates with the pump head 490 (FIG. 5) to draw liquid carbon dioxide through inlet check valve assembly 494 and discharge it through outlet check valve assembly 436. In one embodiment, the Peltier cooling plate 500 is mounted to the flat face of the pump head 490 (FIG. 5) with cooling fins 502 mounted for good thermal contact to the opposite side of the Peltier cooling plate 500.

When an electric current is passed in the proper direction through the Peltier cooling plate 500, heat is withdrawn from the pump head 490 (FIG. 5) and rejected into the cooling fins 502. A fan 504 driven by an electric motor 493 (FIG. 4) withdraws heat from the fins 502. Another Peltier-effect cooled heat exchanger is also utilized in the inlet line.

To control the speed of the motor 492 (FIG. 4), a tachometer wheel 505 is mounted to the shaft of motor 492 (FIG. 4) with a photoelectric tachometer sensor 510 mounted to provide signals reading indicia on the wheel. The signals from the photoelectric tachometer 510 indicate the speed of motor 492 and thus the pumping speed of pump 456. These signals are compared in the controller 450 and utilized to control the speed of the motor 492.

To control the pressure on the outlet line 512 from the pump, a pressure transducer 514 (FIG. 6) generates a signal indicating the pressure. This signal is used as a feedback signal to control the pumping speed. This structure is provided by existing pumps such as the Isco model 260D pump.

Figure 6:
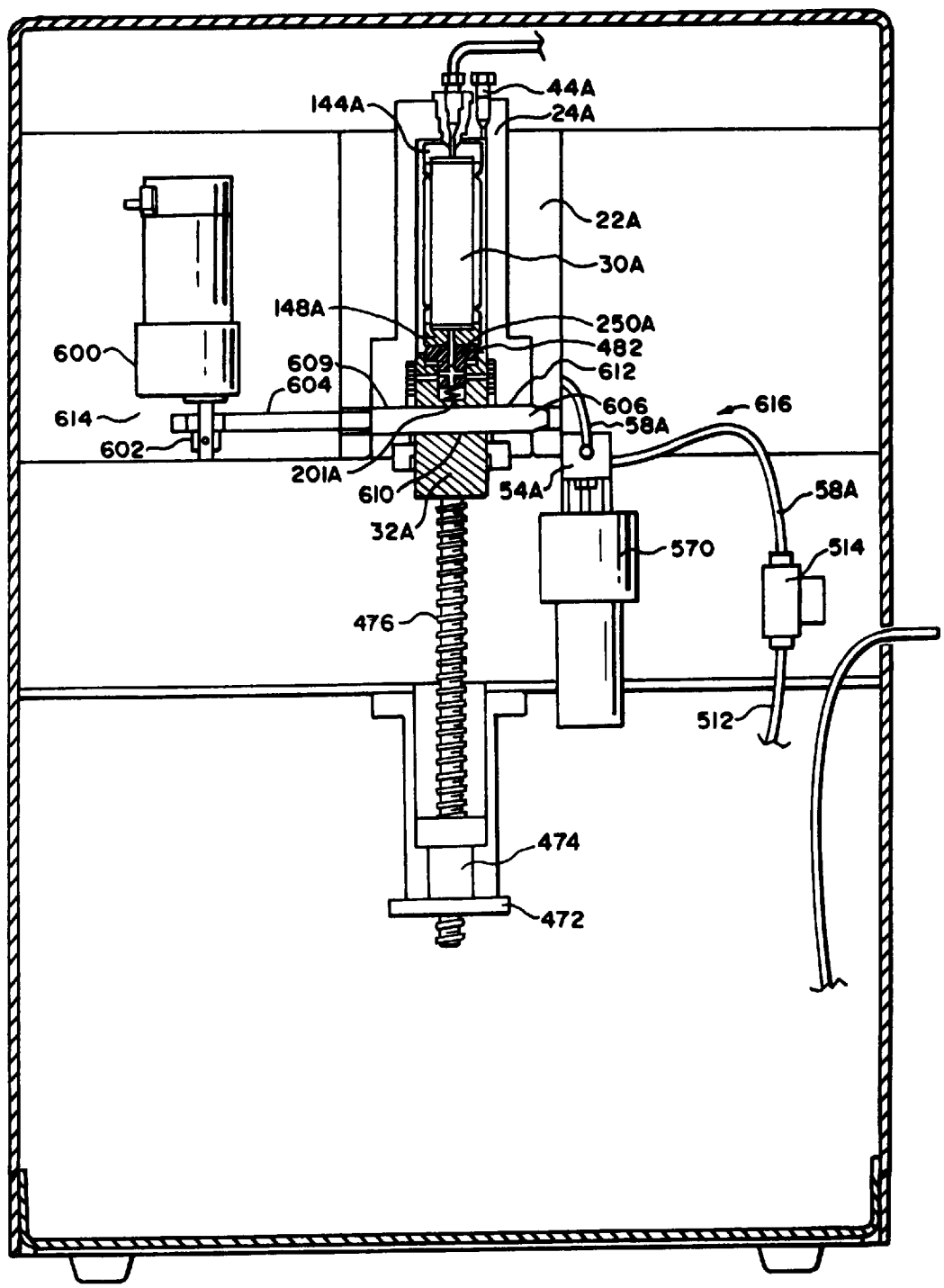
FIG. 6 is a sectional view taken through lines 6—6 of FIG. 4.

In FIG. 6, there is shown a sectional view, partly simplified, taken through lines 6—6 of FIG. 4 having a locking mechanism 614 for locking plug 32A into the pressure vessel 24A and a control mechanism 616 for controlling the extraction fluid. As best shown in this view, the locking mechanism 614 includes a gear motor 600, a pinion 602, a rack 604, a locking pin 606, a hole 609 in the pressure vessel 24A and a hole 610 in the piston or end piece or breach plug 32A and a hole 612 through the other side of the pressure vessel 24A. Instead of a pin 606, a yoke of the type conventionally used as a Winchester 94 rifle locking mechanism advantageously may be used. This type of locking mechanism is a yoke mounted to a pinion 602 and rack 604 as shown in FIG. 6. In this mechanism, a plate with a slot cut out of it to form a yoke is moved by the rack and pinion to pass under the plug 32A to hold it against pressure and provide strong support therewith by further engaging slots in the pressure vessel 24A. The aforementioned slot in the plate provides clearance for the screw 476.

In operation, the gear motor 600 is caused by the control system 450 (FIG. 4) to drive locking pin 606 through the opening 609 n the pressure vessel 24A, through the opening 610 in the piston 32A and through the opening 612 in the pressure vessel 24A by rotating the pinion 602 to drive the rack 604 that carries the locking pin 606, thus locking the cartridge 30A (FIG. 4) in place within the pressure vessel 24A.

To control the flow of extracting fluid from the pump 12 (FIG. 1) into the pressure vessel 24A and cartridge 30A, the control mechanism for extracting fluid includes the gear motor 570 and valve 54A that is connected at one end to the conduit 58A that extends from line 512 and pressure transducer 514 to the conduit 58 which passes into the heat exchanger 40 (FIG. 1). In operation, the gear motor 570 under the control of the control system 450 opens the valve 54A to permit the flow of extracting fluid into the cartridge 30A and pressure vessel 24A during an extraction operation. It also rotates in the opposite direction after extraction is complete to close the valve 54A.

The sample cartridge 30A (FIG. 4) is composed of a tubular sleeve or body portion 140A (FIG. 4) and end pieces 144A (FIG. 4) and 464A (FIG. 4). The end pieces 144A and 464A are made of stainless steel or an inert plastic and carry a stainless steel frit or filter disk centered in the interior of each. The flat, narrowed ends of the tubular sleeve 140A seal against PTFE washers around the frits which seal against the end pieces at the location between the diameters of the filter disks and the inside diameters of the end pieces 144A or 464A respectively.

In FIG. 7, there is shown a supercritical fluid extraction system 10 having a pumping system 12, a supercritical fluid extractor 13, a pressure transducer 15, a variable restrictor system 11 and collection system 19. The pumping system 12 pumps supercritical fluid through the fluid extractor 13 where it dissolves sample. The sample and supercritical fluid then flows from the fluid extractor 13 through the conduit 31 where it influences tha pressure transducer 15 to indicate pressure on electrical conductors 47 and to the variable flow restriction system 11 into the collection system 19.

During this process, the variable restriction system 11 modifies the pressure of the supercritical fluid in such a way as to control the density and solvating power of the fluid and permits abrupt expansion of the supercritical fluid to control where the analytes come out of solution. The expansion of the supercritical fluid is controlled to avoid the requirement for flushing of a restrictor and associated connecting conduit to remove the sample from them.

To pump supercritical fluid, the pumping system 12 includes a pump 23 and a pump controller 25 connected to the extractor 13 through the tubing 27. Clean, supercritical extraction grade $CO_2$ enters a conventional syringe pump 23 and is pressurized to supercritical pressures. A suitable pump controller 25, monitors and controls the pressure developed in the pump. The, controller and pump provide for measurement of fluid pressure and fluid flow rate. The controller also provides a pressure set point and pressure controller for constant pressure operation and a flow set point and flow controller for constant flow operation.

A suitable syringe pump may be an Isco Model 260D Syringe Pump and a suitable controller may be an Isco "D" Series Syringe Pump Controller. Both are available from Isco Inc., 4700 Superior, Lincoln, Nebra. 68504 U.S.A. The supercritical fluid is transferred to an extractor. Suitable extractors are disclosed in U.S. Pat. No. 5,094,753 and are available from the aforementioned Isco, Inc., under the designation ISCO Model SFX 2-10 Supercritical Fluid Extractor. The fluid is heated within the extractor to supercritical temperatures while maintaining supercritical pressure.

The analytical sample is within an extraction chamber inside the extractor 13 under plug 29, and the supercritical fluid extracts the analytes from the sample. The extraction chamber has a fluid inlet for extraction fluid to extract the sample and an outlet for fluid with extracted analyte in solution.

To receive the analyte, the collection system 19 includes a tube 34, an orifice tip 39 at the end of the tube 34, a collection vessel 37, collection solvent 35 within the collection vessel 37, a pierceable septum 41 and a vent tube 43. The supercritical fluid with dissolved analytes flows from the outlet of the extractor through tubing 31 to pressure transducer 15 and then to the variable restriction system 11 through transfer tubing 33. If the transfer tubing 31, transducer 15, tubing 33 and restrictor 11 are not heated, the supercritical fluid may cool to a liquid before reaching the orifice tip 39. This is often of no consequence as the liquid may satisfactorily solvate the analyte and the orifice tip serves to depressurize either supercritical fluid or liquid.

The orifice tip 39 of the variable restriction system is immersed in the collection solvent 35 in a collection container 37. The rate at which the supercritical fluid is discharged into the collection fluid is set by control knob 17 on the variable restriction system 11. At the discharge orifice 39 of the variable restriction system 11, the supercritical fluid or liquid expands into a gas and bubbles through the collection solvent 35, depositing the extracted analyte in the collection solvent.

To insure that as much as possible of the analyte is deposited in the collection solvent 35 or collection container, the supercritical pressure conditions are maintained all of the way down to the orifice tip 39. The collecting tube has a pierceable septum 41 covering its mouth. The septum is pierced by the probe of variable restrictor 11 and by vent tube 43. The vent tube may be led to a fume hood (not shown) in case the gas issuing from it is toxic or flammable. Conductors 47 receive pressure representing electrical signals from the transducer, which signals are used to control pressure as explained hereinafter.

In FIG. 8, there is shown a partly-schematic, partly-sectioned view of a manually-controlled variable-valve restrictor assembly 11 having a valve adjustment section 1013, a temperature control section 1015 and a needle valve section 1011. The needle valve section 1011 is: (1) adjusted as to orifice opening size by the valve adjustment section 1013 to which it is connected to control the pressure in the pressure chamber or column by controlling the release of fluid; and (2) is positioned to provide the effluent directly into a collection chamber environment to avoid loss of sample and the use of time in removing sample from tubing. The temperature control section 1015 controls the temperature of the effluent at the orifice to avoid undesired cooling.

As shown in FIG. 8, the restrictor valve is of the needle valve type and the needle valve section includes a metering, restriction, or expansion area 1248, a control needle 1256, a control needle tip 1257, a barrel tube 1234, a barrel tube tip 1233, a fluid-passing orifice 1240 and a fluid connection hole 1287. The control needle 1256 cooperates with the hole 1287 to carry the flow of effluent into the needle valve where it is received in a space between the barrel tube 1234 and control needle 1256 that leads to the expansion area 1248. At the expansion area 1248, the barrel tube tip 1233 and control needle tip 1257 cooperate to control the expansion and release of the effluent through the fluid-passing orifice 1240 directly into the collection environment.

To permit fluid flow to the clearance area, there are a connecting annular clearance between control needle 1256 and hole 1287 and an annular clearance between the inside diameter of barrel tube 1234 and the coaxial needle 1256. These provide clearance for fluid flow from the fitting 1282 down to the metering, restriction, or expansion area 1248 of the valve where the pressure drop takes place. For this purpose, the control needle tip 1257 rotates and reciprocates within the barrel tube 1233 varying the size of the fluid-passing orifice at expansion area 1248.

The point angle of the needle tip 1257 is more acute than that of the female seat in the barrel tip 1233, making the narrowest portion of the orifice at the far distal surface of the tip at 1240. The needle point angle is 20 degrees inclusive, and the seat angle in barrel tip 1233 is 30 degrees inclusive, but any combination resulting in the needle point having a substantially more acute angle than the seat works, such as a diffference angle between the two in the range of between one degree and 70 degrees. Narrow needle angles and narrow difference angles provide for finer regulation of orifice adjustment.

The expansion of the supercritical fluid occurs essentially at the discharge opening 1240 of the tip 1233, 1257, making the extent of conduit exposed to expanded extraction fluid almost without length, so the expansion occurs in contact with the collection solvent, and the analyte precipitates from the extraction fluid directly into the collection solvent or other collecting trap.

Supercritical pressure is maintained down to the orifice or restriction region 1240 of the distal end of the barrel tip, which is inserted into a collection solvent or other collection trap. The distance between point of the needle tip 1257 and the recessed seat in the barrel tip forms a variable orifice at 1240 which controls the flow rate.

To adjust the pressure and flow rate at the variable orifice 1240, the adjustment section 1013 includes an adjustment knob 1266, a control needle head 1265, male and female screw threads 1264, and an actuation nut 1268. The needle is adjusted using knob 1266 which is fastened to the control needle head 1265 for rotation therewith. The upper end of the needle 1256 is silver soldered into a recess in the underside of control needle head 1265 for rotation and reciprocation with the control needle head and adjustment knob 1266 and head 1256 within the control actuation nut 1268. The control actuation nut includes internal threads that cooperate with the external threads on the control needle head.

With this arrangement, rotating the knob 1266 threads the needle head 1265 and needle 1256 up and down through female threads in the actuation nut 1268. The resulting vertical motion causes the space between the end of the needle tip and the end of the barrel tip to vary, developing a variable orifice 1240. Expanded fluid is then discharged directly into the collection fluid or into the collection vessel. In this design, the entire needle and knob assembly (1257 through 1266) rotates with respect to the barrel tip 1233.

The control needle 1256 extends past the end of barrel 1234 and passes with several thousandths of an inch clearance through hole 1287 in block 1260. This clearance provides for supercritical fluid flow from supply tubing (not shown) and through a conventional compression fitting connector, not shown in FIG. 8, screwed into conventional female compression fitting 1282 for a $\frac{1}{16}$" tubing connector.

To permit fluid flow, there are connecting annular clearance between control needle 1256 and hole 1237, the annular clearance between the inside diameter of barrel tube 1234 and the coaxial needle 1256. These provide clearance for fluid flow from the fitting 1282 down to the region of silver soldered joints 1280 and 1281. Past these joints, the fluid flows through the annular region between control needle 1256 and barrel tip 1233, and between needle tip 1257 and barrel tip 1233, and on to the region of fluid restriction 1240.

Sealing around needle 1256 is effected by canted helical spring-activated Teflon flanged seal 1262, available from Bal-Seal Engineering Company, Inc. 620 West Warner Avenue, Santa Ana, Calif. 92707-3398, U.S.A. The seal is captivated between block 1260 and seal retainer block 1261. Four screws, one of which is shown as 1269 in the figure, clamp blocks 1260 and 1261 together through force exerted by the screw heads upon support block 1263. These screws are #4X ¾" cap screws. Seal 1262 prevents supercritical fluid from the port 1282 from leaking away from the metering region 1240 and towards the adjustment knob 1266.

The expansion of the supercritical fluid occurs essentially at the discharge opening 1240 of the tip 1233, 1257, making the extent of conduit exposed to expanded extraction fluid almost without length, so the expansion occurs in contact with the collection solvent, and the analyte precipitates from the extraction fluid directly into the collection solvent.

Supercritical pressure is maintained down to the orifice or restriction region 1240 of the distal end of the barrel tip, which is inserted into a collection solvent or collection vessel. The distance between point of the needle tip 1203 and the recessed seat in the barrel tip forms a variable orifice at 1240 which controls the flow rate, and is adjusted using knob 1266.

For such adjustment, the control needle head 1265 is finely threaded, using 80 threads per inch. Rotating the knob 1266 threads the needle 1256 up and down through action of female threads in the actuation nut 1268 upon needle head 1265. The resulting vertical motion causes the space between the end of the needle tip and the end of the barrel tip to vary, developing a variable orifice 1240. Expanded fluid is then discharged directly into the collection fluid or into the collection vessel. In this design, the entire needle and knob assembly (1257 through 1266) rotates with respect to the barrel tip 1233.

The concentric arrangement of barrel 1233–1234 and needle 1256, 1257 allow the probe of the apparatus to be made to any suitable length. Five or six inches is typical. Buckling of the needle due to compressive loading is prevented by the inside diameter of barrel 1233, 1234, which supports the smaller needle 1257, 1256. The barrel experiences a tensile loading, counteracting the buckling tendency of the needle. These two components working in unison provide for a mechanically stable probe, regardless of length.

The needle tip 1257 is preferably made of 17-7 PH stainless steel which has been hardened to CH900 which produces a strength of about 280,000 pounds per square inch. The barrel tip 1233 should preferably be softer than the needle tip, although still hard. A recommended material is type 15-7Mo stainless steel hardened to RH950 which produces a strength of about 180,000 pounds per square inch. The needle tip 1257 is silver soldered to control needle 1256 at the region 1281. The distal region of tip 1257 is water cooled during this silver soldering process so that the heat from the soldering does not adversely affect its hardness. Barrel tip 1233 is silver soldered to barrel tube 1234 at region 1280. The pointed or distal end of barrel tip 1233 is water cooled during silver soldering to prevent the heat from adversely affecting its hardness.

The major outside diameter of barrel 1234 and barrel tube 1234 is 0.125" in the embodiment of FIG. 8. The inside diameter is 0.075" and length is 6 inches. The diameter of control needle 1256 is 0.062" in the embodiment shown. The diameters of needle tip 1257 and barrel tip 1233 are stepped down near their distal ends to provide more space for a restrictor heating element and thermal and electrical insulation around the heating element. Following along the valve in the general direction of adjustment knob 1266, barrel tube 1234 progresses through electrical insulator ring 1237, beyond which barrel holding flange 1236 is silver soldered to it.

The barrel tube 1234 may be made of 316 stainless steel. Barrel holding flange 1236 may be made of type 303 stainless steel. Electrical insulator ring 1237 is machined from polyetheretherketone plastic. The barrel tube 1234 ends inside of an extension of recess 1288 in connection port block 1260. The four screws, one of which is indicated at 1274, are each type #4-40X ⅜" cap screws, one of which is indicated at FIG. 8. They captivate flange 1236 and barrel tube 1234 between barrel holder block 1223 and connecting port block 1260. Gasket 1291, a washer of 0.005 inch thick polytetrafluoroethylene, effects a seal between flange 1236 and block 1260 and prevents leakage of fluid.

The control needle 1256 is silver soldered to needle head 1265 at region 1259. Needle head 1265 carries fine, 80 thread per inch male screw threads (¼-80 UNS), shown at 1264. These threads cooperate with female threads inside the central bore of actuation nut 1268. Actuation nut 1268 is made of Nitronic 60 stainless steel for resistance to wear and galling. Rotation of brass adjustment knob 1266 rotates needle head 1265 and its threaded region 1264 because of the action of set screw 1267 within the adjustment knob. Rotation of threads 1264 with respect to fixed threads and nut 1268 imparts reciprocating and rotating motion to control needle 1256 and its tip 1257. This provides adjustment of the restrictor orifice 1240 and therefore regulation of flow of fluid entering fitting 1282 and exiting the orifice 1240. Metal parts whose material is not otherwise indicated may conveniently be made of type 303 stainless steel.

The seat in the barrel tip 1233 should be very hard, and the tapered tip of needle tip 1257 should be harder yet so that it does not deform or "ring". The needle tip 1233 may be made of type 15-7Mo stainless steel hardened to RH 950 (180 ksi tensile) and the needle 1257 may be made of cold drawn 17-7PH stainless stell hardened to CH 900 (280 ksi tensile). Preferably the end of the outer wall 1202 of the barrel tip is coned for punching through septum 1108 across collecting tube 37 (FIG. 7).

In FIG. 9 there is shown a partly broken away, partly sectioned view of a variable restrictor forming a portion of the assembly of FIG. 8 and in FIG. 10 there is shown an enlarged fragmentary sectional view of the restrictor of FIG. 9. The needle tip 1257 shown in FIG. 8 is not shown in either FIG. 9 or FIG. 10 but a heater for heating the restrictor is shown comprising a winding 1201 of resistance wire 1243 that is connected to the temperature control section 1015 (FIG. 8). This heater is used to electrically heat the barrel tip 1233 in the vicinity of the metering or restriction region 1240. The helical coil 1201 comprises approximately 30 turns of resistance wire 1243 having a high temperature coefficient of resistance.

The wire 1243 is Pelcoloy (registered trademark of Molecu-Wire Company), 0.004" diameter insulated with a polyimide coating with a thickness of about 0.00025". This wire is composed of 70% nickel and 30% iron and has a temperature coefficient of +4,500 parts per million per degree celsius.

One end of the wire 1243 is resistance welded to the barrel tip 1233 at location 1241. (FIG. 10). The other end of the coil is led up the barrel and resistance welded at location 1235 onto step 1244 of electrical connection ring 1238.

To insure a good thermal contact between the wire 1243 and the barrel, the barrel is first given a coating of uncured epoxy resin mix (Epoxylite Corp. type #5403) underneath the location upon which the wire is to be set. When the wire is wound on the barrel through the epoxy resin 1242, the epoxy resin fills all of the gap between the wire and the barrel. The epoxy is also placed along the length of wire 1243 which extends from the coil to the resistance weld at electrical connection at 1235. Electrical connection ring 1238 lies on the step 1245 of electrical insulator ring 1237.

Ring 1237 is machined from polyetheretherketone plastic resin and insulates the electrical connection ring 1238 from the barrel 1234. The assembly as indicated is heated to 150 degrees Celsius to polymerize the epoxy resin 1242. The assembly as shown in FIG. 9 is placed in a conventional injection mold and 3/16 inch outside diameter plastic sheath 1239 is molded over the heating coil 1201 and the barrel 1234–235 to provide both electrical and thermal insulation. A chemically resistant plastic resin is used for molding sheath 1239 so as also to provide chemical resistance when the end 1240 is immersed deeply into a collecting liquid as shown in FIG. 7. Hoechst-Celanese VECTRA A115 liquid crystal polymer is satisfactory for this purpose. Preferably this molded assembly is stress-relieved at 250 degrees Celsius before uses.

From FIG. 9 it is apparent that, if a voltage is applied between electrical connection ring 1238 and barrel holding flange 1236, an electric current flows through ring 1238, resistance weld 1235, wire 1243, heating coil 1201, resistance weld 1241 (FIG. 10), barrel tip 1233, barrel 1234 and flange 1236. This heats the barrel tip 233 in the region of the metering restriction tip 1240, therefore heating the metering orifice and preventing the formation of either ice or precipitated analyte. Preferably the heating is effected through a temperature controller which senses temperature by substantially constantly monitoring the electrical resistance of the aforedescribed circuit.

Most of the resistance of this circuit is within the heating coil 1201, and its large temperature coefficient of resistance is used to provide a temperature feedback signal through the variation of electrical resistance between the electrical connections at 1238 and 1236. Temperature controllers which operate on the principle of sensing the temperature of the heating element itself are described in Robert W. Allington U.S. Pat. No. 4,438,370 and in co-pending U.S. patent application Ser. No. 08/027,257, the disclosure of which is incorporated herein by reference. This method of temperature sensing is preferred to avoid the bulk and difficulty of thermal insulation and electrical connection associated with the use of a thermocouple.

In FIG. 11 there is shown a schematic view of the temperature control section 1015 used to control the temperature of the variable restrictor and having for this purpose a four-pin connector plug 1229, two current supply leads 1221 and 1228, two voltage sensing leads 1246 and 1247, electrical conection lug 1227. The current supply lead 1228 and voltage sensing lead 1246 electrically connect the four pin connector plug 1229 to the lug 1227 and the current supply lead 1221 and the voltage sensing lead 1247 connect the four pin connector plug 1229 to brass electric contact ring 1225 (FIG. 8 and FIG. 11) The electrical conection lug 1227 is screwed by screw 1270 (FIG. 8) to block 1263 The four-pin connector plug 1229 is connected to the a controller within computer 2100 (FIG. 18) and the four leads 1228, 1227, 1246 and 1221 are used for heating current and the resistance (voltage) sensing according to the Kelvin method. To this end, leads 1228 and 1246 terminate in electrical conection lug 1227 which is connected by screw 1270 (FIG. 8) to block 1263 which is in electrical contact with block 1261 which is in electrical contact with block 1260 which is in electrical contact with block 1223 which in turn is in electrical contact with flange 1260 which is silver soldered to the barrel 1234. The other two leads, 1221 and 1247, of connector plug 1229 are soldered at 1226 to brass electric contact ring 1225 carrying setscrew 1222 which holds it in mechanical and electrical contact with electrical connection ring 1238 which in turn is electrically connected to wire 1243.

A temperature controller within computer 2100 (FIG. 18) passes a current through wires 1221 and 1228 and therefore through the heating coil 1201. The voltage developed across heating coil 1201 in response to this current is conducted to leads 247 and 246 and back to the sensing input of the temperature controller.

As the temperature controller delivers the current through leads 1221 and 1228 the heating element in 1201 increases in temperature and therefore increases in resistance. This causes the voltage drop across it, which is brought through leads 1247 and 1246, to increase by a disproportionately larger amount. This is sensed by the controller to determine the temperature of the heating element.

When the temperature of the heating element reaches the set point temperature of the controller, the controller decreases the current through leads 1221 and 1228 and thereby regulates the temperature of the heating element to the desired amount. Electrical insulator block 1224 covers and captivates contact ring 1225. Block 1224 may be machined from ultra high molecular weight polyethylene.

In FIG. 12, there is shown another embodiment of variable restrictor 1018A having as its principal parts a body portion 1052A, an inlet port 1050A, a heater 1080, a probe 1054A and a tip 1088. A Watlow Firerod (trademark of Watlow Electric Co., 12001 Lackland Road, St. Louis, Mo. 63146, U.S.A.) cartridge heater 1080, model C1E13 or similar is fitted into a drilled hole in the body to maintain supercritical temperature in the apparatus. These heaters operate on 120V, supplied through wires 1082 and 1084. The cartridge supplies supplemental heat when current is applied, providing additional heat to the supercritical fluid so that it is kept at supercritical temperatures in the extractor.

To control the temperature, a thermocouple (not shown) is mounted in a hole 1086 in the body, within 0.063" from the fluid path, and is electrically connected to a temperature controller (not shown). The heater is turned on and off by the temperature controller to maintain the desired temperature as measured by the thermocouple. Heat is transferred from the cartridge to the valve body 1052A, and from the valve body to the probe 1054A and to the fluid primarily by conduction.

The probe barrel tip end 1202 (FIG. 8) may be used as a variation of tip 1088 and probe 1054A shown in FIG. 12. Tip 1088 and probe 1054A permit the tip 1088 to be threaded into the probe 1054A and thus allow for repair and replacement. The tip style 1088 results in a slightly longer discharge conduit 1068A, but still is only about 3/16" long. Because of its short length and its increasing diameter which enlarges from the variable orifice to the surrounding outside region, the effect of the conduit is negligible. The mating orifice surfaces are sections of a sphere, rather than ones as in FIG. 8.

In FIG. 13, there is shown, a still another embodiment of variable restriction system 1018B adapted to be motor driven for automated control having an inlet port 1050B, a motor 1110, an encoder system 1118, a probe barrel 1505, a movable needle 1504 and a partially spherical portion 1515 at the tip of the probe. Supercritical fluid containing dissolved analyte enters through port 1050B, with seal 1107 preventing the loss of fluid along the needle. The port 1050B and seal 1107 are identical to those in FIG. 8, items 1282 and 1286, but other port configurations and seal designs would function equally well. The supercritical fluid then flows to the tip 1505 through the annular space between the needle 1504 and the probe barrel 1504. The diameters of the needle 1054 and barrel 1504 are the same as in FIG. 8. As was described in FIG. 8, supercritical pressures are maintained up to the tip 1503 of the probe.

A 48 pitch, 40 tooth worm gear 1114, which in the preferred embodiment may be purchased from Winfred Berg, is loosely positioned on the shaft 1106. A 48 pitch, single start worm 1108 is attached to the shaft of motor 1110, which is a Lo-Cog (registered trademark of Pittman Motor Co., Harleyville, Pa. 19438–003) D-C Servo Motor, model 9413, manufactured by Pittman. This worm 1108 is engaged with the worm gear 1104, so that the rotation of the motor armature 1112 causes the worm gear 1104 to rotate.

As the worm gear 1104 rotates in a first direction, it contacts pin 1114, causing the threaded shaft 1106 to rotate also, opening the restrictor valve. An opposing torsion spring 1116 part number SPR3-5 purchased from W. M. Berg, Inc. 499 Ocean Avenue, East Rockaway N.Y. 11518, U.S.A. causes the shaft 1106 to rotate in the opposite direction when the motor 1110 is reversed, closing the restrictor. The torsion spring 1116 generates about 10 ounce-inches of torque when the valve is closed.

When the restrictor properly closes by rotary force from the spring 1116, pin 1114 separates from a slot in gear 1104. Motor 1110 drives the valve open but can only permit it to close by spring force. This prevents the motor from driving the restrictor closed too tightly. The design is motor to open, spring to close. A quadrature position encoder system 1118 provides an electrical signal of motor rotor position and therefore valve needle position.

The spring 1116 closes the restrictor, applying enough force at the closed position to nearly stop the fluid flow, but not enough to cause galling of the needle tip 1515 or barrel tip 1503. The torsional spring force, working through the 5/16-48 cooperating threads 1120 in shaft 1106 and packing nut 1109 generate a vertical force of about 23 pounds on tip 1058B by the needle 1056B is provided to allow the needle 1504 to not rotate independently of rotation of the shaft 1106, thereby reducing the possibility of galling of the needle tip 1515 during closing.

Slip joint 1122 comprises a hard thrust ball 1124 located between the top of a recess drilled in the bottom end of shaft 1106 and the top end of needle 1056B. This allows the shaft to force the needle down without rotating it. A loosely-fitting disk 1122 of stainless steel type 303 with an outside diameter of 0.125" and a thickness of 0.063", silver soldered to the needle 1504 allows the shaft 1106 to raise the needle.

A hollow screw 1126 holds the disk in a matching hole in the end of shaft 1106. A slight clearance (about 0.0005") between the disk 1122, the hollow screw and disc 1126 and the shaft 1106 allows the needle 1059 to not rotate with respect to rotary motion of the shaft 1106, but does not allow significant vertical play. This creates a rotation slip joint at 1122, which prevents the needle tip 1515 from rotating with respect to barrel tip 1503 at full closure of the restrictor. Forced rotation of the needle tip 1515 with respect to the barrel tip 1503 when the needle 1504 is closed results in wear and galling of the area where the needle tip and the barrel tip contact.

Shaft 1106 is threaded with 5/16-48 UNS threads 1120, and the rotation of shaft 1106 in one direction moves the needle tip away from the barrel tip. The shaft 1106 is threaded at 1120 into the packing nut 1109 of the restrictor, generating a vertical motion of the needle 1504 as the shaft 1106 rotates. This vertical motion causes the spacing between the needle tip 1515 and the barrel tip 1503 to change, resulting in a change in the orifice area which controls the flow. The threads 1120 are coated with an anti-seize lubricant or similar to prevent wear and galling of the threads, which experience about 23 lbs. of axial loading in operation.

Figure 14:
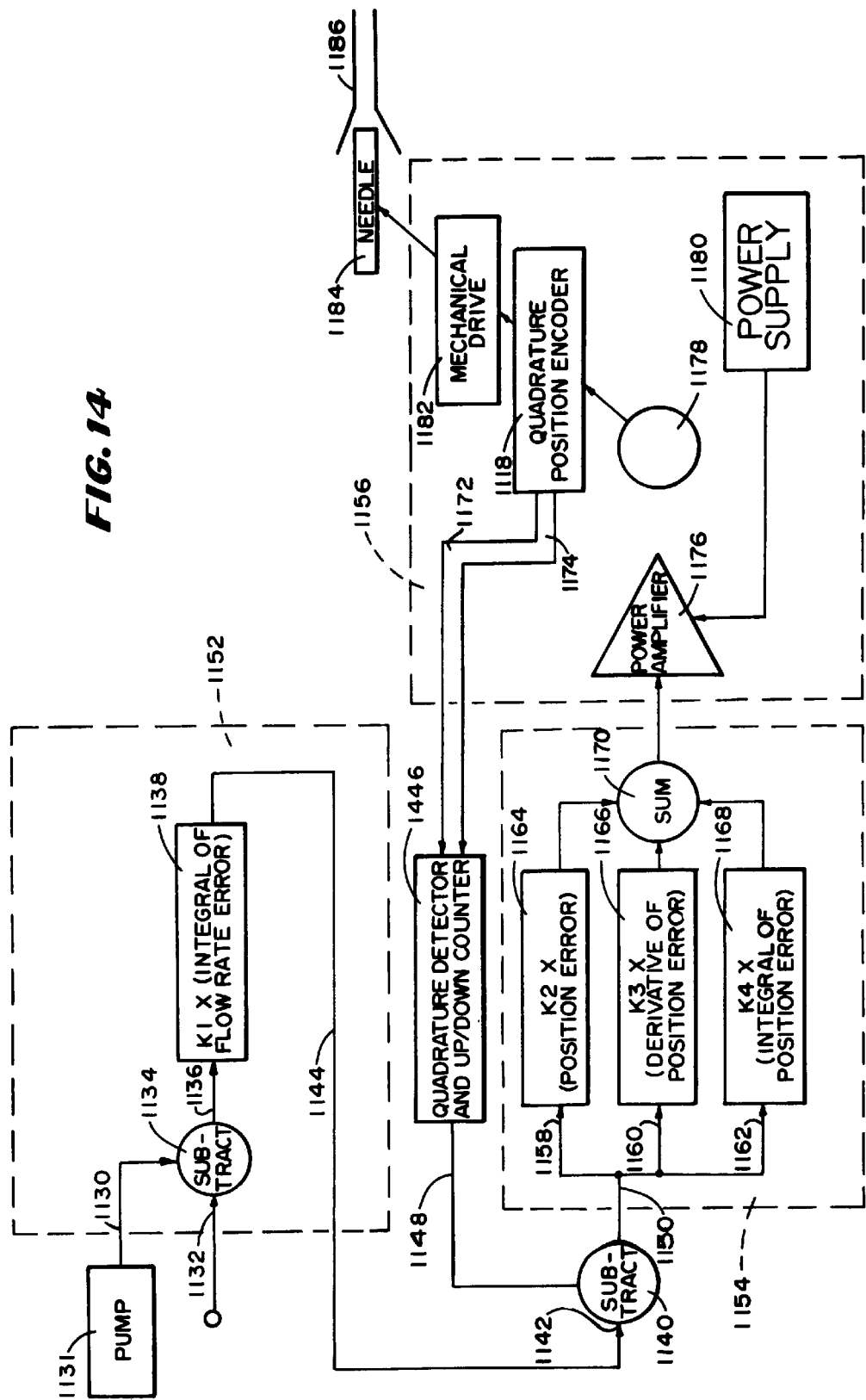
FIG. 14 is a block diagram of a circuit usable in accordance with the embodiment of FIGS. 7 and 13.

In FIG. 14, there is shown a block diagram of the restrictor and the controller for the restrictor. This controller may be used for control of the motorized variable restrictor for automatic independent control of the pressure within, and fluid flow rate through, an associated supercritical fluid extractor or supercritical fluid chromatograph. In this embodiment, the pump sets a constant pressure and the restrictor sets a constant flow.

The restrictor controller of FIG. 14 has a motor angular position set point signal generator 1152, a servo amplifier 1154, a restrictor-valve control circuit 1156, an up/down counter and decoder, a subtractor 1142, a needle 1184 and a valve seat 1186. An Isco "D" series pump 1131 keeps the system at constant pressure and the restrictor is servo-operated to maintain a desired flow rate.

A flow rate feedback signal on the flow rate feedback conductor 1130 is read from the volume (piston displacement) sensor in the syringe pump 1131. Thus, no gas flow rate measuring transducer is required at the outlet. This pump piston feedback signal is subtracted from the flow rate set point signal on the flow rate set point conductor 1132 entered by the opera to in a signal subtraction circuit 1134. The result is a flow rate error signal on conductor 1136 (a difference) which is integrated and multiplied by a constant K1 in multiplier 1138 and is sent to a second subtraction circuit 1140 as a valve motor angular position set point signal applied to input 1142 through a conductor 1144.

The restrictor valve position is sensed by motor shaft position encoder 1118, converted to motor position by quadrature detector/counter 1146 and presented as valve motor position signal on conductor 1148.

The valve motor angular position signal on conductor 1148 is subtracted from the motor angular position set point signal 1142, resulting in a valve position error signal on conductor 1150. This signal is applied to a servo circuit 1154. An amount equal to the constant K2 times the position error signal on conductor 1158, plus a constant K3 times the rate of change of position error on conductor 1160, and plus a constant K4 times the integral of the position error on conductor 1162 is then numerically summed in adder 1170 and the power amplifier 1176 is controlled based on this sum from 1170.

The power amplifier 1176, deriving power from power supply 1180, excites the valve motor 1178, causing it to rotate. A quadrature position encoder 1118 attached to the motor shaft 1178, signals the current position and direction of rotation using two phase signals 1172 and 1174. These signals 1172 and 1174 are measured by the quadrature detector and up/down counter 1146, which provides the valve motor angular feedback signal 1148 to the position subtraction circuit 1140.

The motor 1178 is also attached to the mechanical drive 1182 that moves and positions the needle 1184 with respect to the seat 1186. This can be any mechanism that translates the rotational motion of the motor 1178 into a position adjustment of the needle 1184, such as the mechanism described above in FIG. 13.

In FIGS. 15 and 16, there is shown a front elevational sectional view and a side elevational sectioned view of a motor controlled restrictor operated by spring compression, but having substantially the same principal parts as the embodiment of FIG. 13. Mechanically, the closing force is supplied by spring compression, rather than by a torsion spring. In this arrangement, the needle 1190 can be positively prevented from rotating during closing, preventing destructive galling of the needle tip 1192.

The opening motion is provided by motor 1178, a Lo-Cog (registered trademark of Pittman Motor Co., Harleyville, Pa. 19438–0003) D-C Servo Motor, model 9413, manufactured by Pittmann. Any suitable motor or mechanical device creating rotational motion at enough torque would work as well.

A 64 pitch, 11 tooth gear, supplied by Pittman attached to and part of motor 1178, rotates a 64 pitch, 192 tooth 20° pressure angle Delrin™ (DuPont) spur gear 1196, purchased from Forest City Gear, part number 69-0943-237. Spur gear 1196 is mounted to a support spool 1198, machined from 17-4 PH stainless steel, hardened to Rockwell C42-48. Spool 1198 is threaded onto 182FM (Carpenter Technologies) stainless steel shaft 1200 with 5/16-48 UNS threads. The shaft 1200 is prevented from rotating by clamp 1202, which is held to the shaft by friction force created by a #4-40 cap screw 1204 (FIG. 16). The rotation of clamp 1202 is prevented by pin 1206, which travels in a slot 1208 in the support plate 1210. The rotation of spool 1198 results in a vertical motion of shaft 1200, which presses against the spring retainer 1212 at 1218, lifting the needle 1190. The needle 1190 is attached to the spring retainer 1212 by a compression fitting (Vespel™ DuPont ferrule) 1214, which is compressed and held in place by compression nut 1216.

As the spring retainer 1212 is lifted by action of motor 1178, gear 1196, spool 1198 and shaft 1200, the helical compression spring 1220 is compressed. When this spring 1220 is compressed flat, the mechanism stalls the motor 1178, limiting the distance the needle 1190 can be lifted.

When the motor 1178 is operated in the opposite direction, closing the variable orifice 1192, the shaft 1200 is lowered, and the spring 1220 force the needle 1190 downward. A type 316 stainless steel wear spacer 1222 is used to prevent damage to the aluminum top block 1224 by spring 1220. Once the variable orifice is fully closed, shaft 1200 separates from the spring retainer 1212, and the variable orifice is held closed by spring force only.

When the orifice 1192 is fully closed, the spring 1220 is still somewhat compressed, and hold the orifice 1192 closed with 20 to 40 lbs. of force. As the motor 1178 continues to lower the shaft 1200, the shaft 1200 contacts the seal capture nut 1217 at 1228, causing the motor 1178 to stall. This limits the distance shaft 1200 can move downward, eliminating the need for shaft position switches.

The spool 1198 and gear 1196 assembly rotates freely on ball bearings 1236, and is supported by spacers 1238 from the bearings 1236. Bearings 1236 are lightly pressed into the support plates 1240 and 1242. Shaft 1200 is about 0.001" smaller in diameter than the inner diameter of bearings 1236, and can freely move vertically inside the bearing 1236.

The needle 1190 is attached to the spring retainer 1212 using a compression ferrule 1214 and nut 1216. This method allows the needle 1212 to be positioned during assembly and adjusted if necessary. The needle 1212 is prevented from buckling in operation by being contained throughout its length inside the spring retainer 1212, shaft 1200, seal capture nut 1217 and probe 1234. Throttling of the supercritical fluid takes place between the narrow coned end 1192 of the needle 1190 and a broader angled female cone in tip 1230.

Supercritical fluid enters the apparatus through a compression fitting port 1232, and flows in the annular space created by the probe 1234 and the needle 1190. The fluid is prevented from flowing upwards along the needle 1190 by the PTFE seal with canted coil backing spring 1248, type X15829 made by Bal-Seal and described above. A 303 stainless steel backing ring 1244 holds the seal 1248 in place in the body 1250, and is retained by a seal backing nut 1217. A 303 stainless ring 1246 is soldered to the probe 1234, and makes a metal to metal seal with the body 1250 due to the compression action of the holding nut 1252. optionally, a gasket washer can be incorporated to facilitate sealing. The fluid path formed is as small as possible, to reduce dead volumes and prevent the necessity of washing out the apparatus. None of the drive components and anti-rotation features are in the fluid path.

The components of the apparatus are held together by two parallel side plates 1210 and 1254. A spring support block 1224 transfers the spring force to the side plates 1210 and 1254, which transfers the spring force to the spacer blocks 1276 and 1278 and body 1250. The probe 1234 is attached to the body 1250 with the holding nut 1252, and holds the tip 1230. The spring force is transferred to the tip through this path, and results in a tensile loading of the outer tube of the probe.

The upper end of the spring 1220 transfers the spring force to the spring retainer 1212, which transfers the force to the needle 1190 through the compression ferrule 1214 held in place by the nut 1216. This results in a compressive force on the needle 1190 that produces the tensile force in the probe 1234. The needle 1190 can be driven downwards into tight fit within the tip 1230 only through force from the spring 1220. The motor 1178 can lift the needle away from the tip and against the springs. Force from the motor does not lower the needle, and therefore the action of the valve is "motor-to-open/spring-to-close". This prevents damage to the end 1192 of the needle and to the seat within tip 1230. The motor position is sensed by encoder 1256. The motor is indicated as 1178 in FIGS. 14 and 17.

Figure 17:
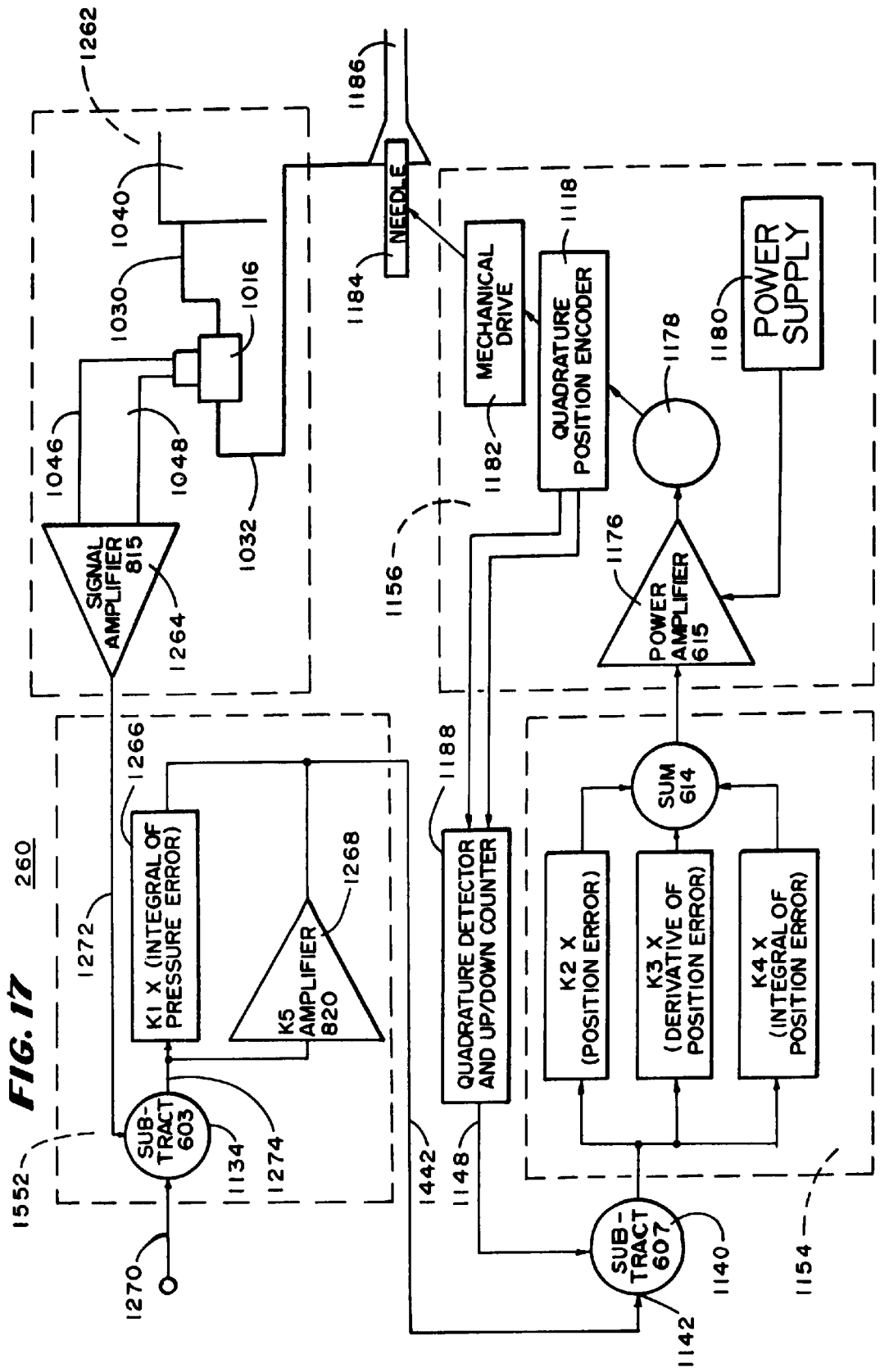
FIG. 17 is a block diagram of another embodiment of circuit usable with the embodiments of FIGS. 7, 13

In FIG. 17, there is shown another automatic restrictor control embodiment in which the pump sets a constant flow and the restrictor sets a constant pressure. The restrictor and restrictor controller have a motor angular position set point signal generator 1152, an up/down counter 1188, a subtractor 1140, a servo amplifier 1154, a restrictor valve control circuit 1156, a movable needle 1184, a valve seat 1186 and a pressure monitoring system 1262. The pump (not shown) driven by motor 1178 supplies the fluid to the apparatus as a constant volumetric flow and the restrictor regulates the expansion process by controlling the pressure.

In cooperation with the circuit of FIG. 17, the pressure transducer 1016 monitors pressure in tubing 1030 connected to the outlet of supercritical fluid extractor 1040 and in connecting tubing 1032 upstream of the variable restrictor needle 1184 and seat 1186. An electrical signal from the transducer is carried on output of the amplifier on lead 1272 is a pressure feedback signal. The pressure feedback signal 1272 is subtracted from a desired pressure set point 1270 using a subtraction circuit 1134. The result is a pressure error 1274 signal, which is multiplied at amplifier 1268 by a constant K4 and integrated at 1266. The outputs of amplifier 1268 and integrator 1266 are added together and create a valve motor angular position set point signal on lead 1142. This valve motor angular position set point signal is logically and functionally identical to the motor angular position set point based on flow rate 1142 (FIG. 14). The remainder of the control circuit is the same as in FIG. 14, except that since the principal feedback is pressure instead of pump piston displacement, the restrictor controls pressure rather than flow rate.

From the above description, it can be understood that the supercritical extractor or supercritical fluid chromatograph of this invention has several advantages, such as for example: (1) it reduces the amount of sample that is coated onto the inside walls of the tubing; (2) it reduces the time and expense of removing contaminants caused by prior samples from tubing; (3) it collects a large amount of sample, particularly by avoiding the escape of volatile sample; (4) it is particularly adaptable to automatic operation of an extractor; and (5) it offers a restrictor that does not clog, either with ice or analyte.

Figure 18:
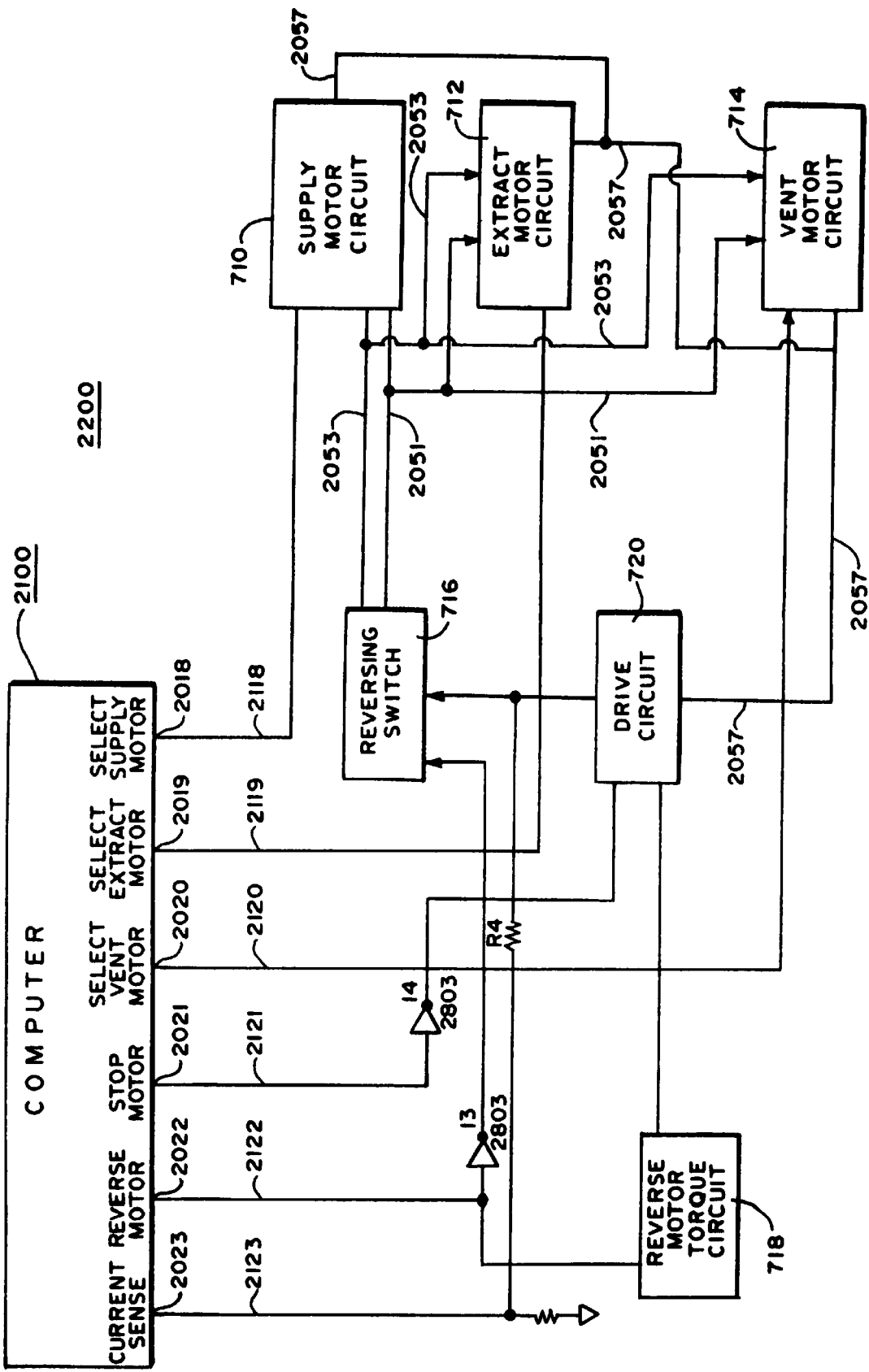
FIG. 18 is a block diagram of the circuitry for operating the system.

In FIG. 18, there is shown a block circuit diagram of the control circuitry 2200 for gear motor 570 (FIGS. 4, 5 and 6) which operates supercritical fluid supply valve 54A(FIG. 6), gear motor 574 (FIG. 5) which operates extraction valve 50A (FIG. 5), and gear motor 573 (FIG. 4) which then operates valve 52A (FIG. 4).

The control circuitry 2200 includes a programmer or other computer 2100, controlling a supply motor circuit 710, an extract motor circuit 712 and a vent motor circuit 714 to control the valves 54A(FIG. 6), 50A(FIG. 5) and 52A(FIG. 4), respectively, a reversing switch 716, a drive circuit 720 and a reverse motor torque circuit 718. The computer 2100 is electrically connected to the supply motor circuit 710, the extract motor circuit 712 and the vent motor circuit 714 through a conductors 2118, 2119 and 2120 electrically connected to output terminals of the computer 2100.

The drive circuit 720 supplies power to a reversing switch 716 that is also electrically connected to the supply motor circuit 710, the extract motor circuit 712 and the vent motor circuit 714 to apply power to the selected one of those motors with a polarity that controls the direction of movement of the motors to open a valve or close a valve. The reversing switch 716 is electrically connected to conductor 2122 from a port 2022 in the computer to activate the reverse direction for closing the valve. This port is electrically connected to the reverse motor torque circuit 718 which controls the amount of torque in opening the valve and is for that purpose electrically connected to the drive circuit 720. A feedback circuit on conductor 2057 is electrically connected to the supply motor circuit 710, extract motor circuit 712 and vent motor circuit 714 to provide a feedback signal to the controller which controls the stopping of the motor when the valves close fully. The stop motor signal comes from conductor 2121 from the port 2021 in the computer or programmer 2100.

In the preferred embodiment, a programmable computer with timing circuits is utilized. It is the same computer used to operate the embodiment of FIG. 3. However, a manual switch can be used instead which switch is connected to a positive voltage supply to energize the corresponding motor when closed.

The control circuit 2200 includes a supply motor circuit 710, an extract motor circuit 712, a vent motor circuit 714, a computer or programmer 2100, a reversing switch 716, a drive circuit 720 and a reverse motor torque circuit 718. The supply motor circuit 710, extract motor circuit 712 and vent motor circuit 714 open and close corresponding ones of the valves 54A, 50A and 52A.

To control the valves, the computer or programmer 2100 has a plurality of output conductors that determine which valve is to be moved and the direction in which it is to be moved. This, in the preferred embodiment, is the computer which operates the extractor 10A (FIG. 3) but may be any timing device or indeed, instead of a programmer, manual switches may be used to close circuits to 15-volt DC voltages to open and close the valves as desired by an operator.

In the preferred embodiment, conductors 2118, 2119 and 2120 are connected to outputs 2018, 2019 and 2020, respectively, of the computer or programmer 2100 and to corresponding ones of the supply motor circuit 710, extract motor circuit 712 and vent motor circuit 714 to select those valves for opening or closing. A low-level signal on lead 2127 attached to computer output port 2021 is electrically connected through inverter 2026 to the drive circuit 720 to cause it to supply power to the selected valve through the reversing switch 716 which is electrically connected to the port 2023 through conductor 2123 to the reversing switch 716 and drive circuit 712.

The reversing switch 716 is electrically connected through conductors on the same cartridge may be made by leaving the sample cartridge 30A in place and advancing only the collection reel. The cycle of opening the valves and extracting is then repeated until the number of extractions from the single sample cartridge 30A (FIG. 3) have been made and the extractant deposited in a number of successive collection vials.

Figure 19:
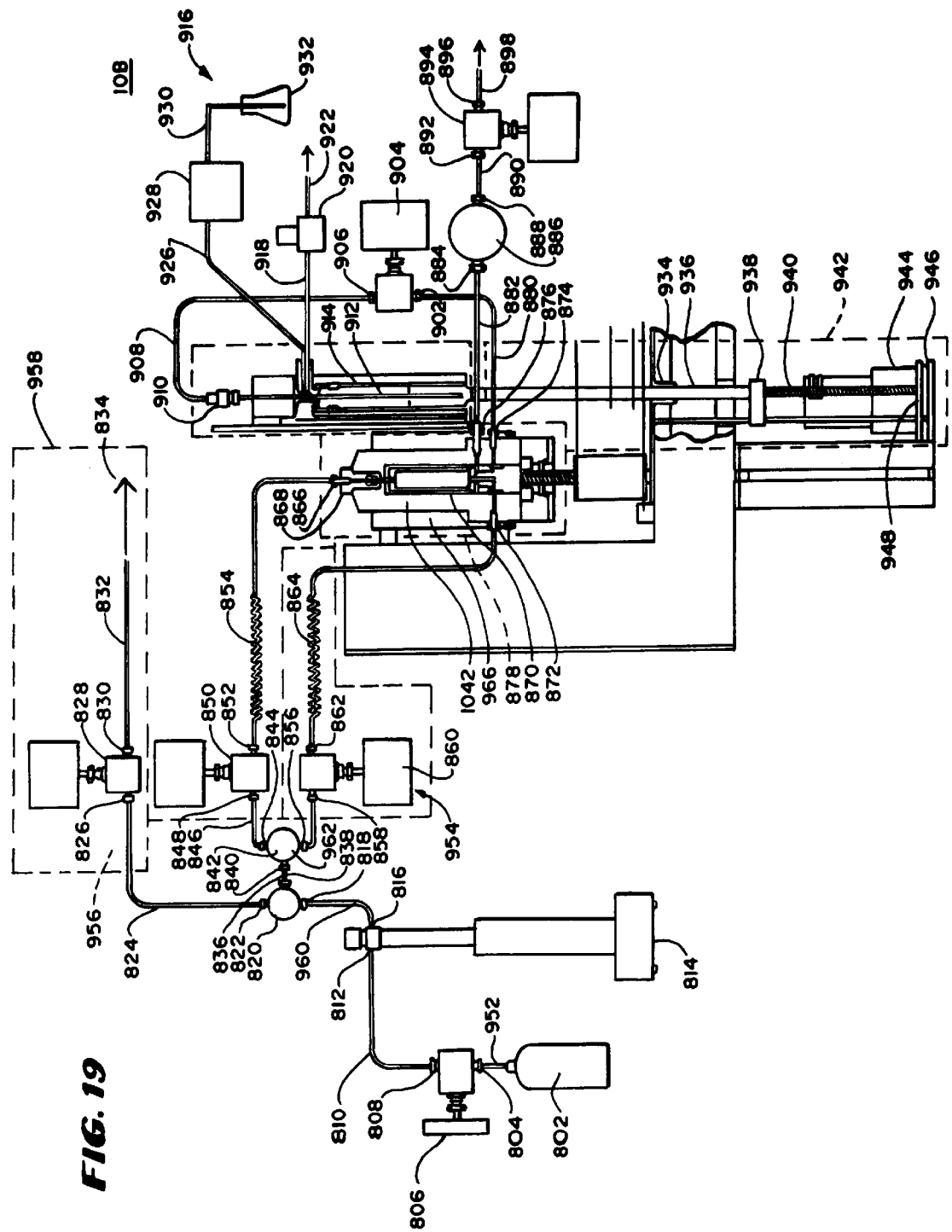
FIG. 19 is a schematic diagram illustrating another embodiment of automated supercritical fluid extraction.

In FIG. 19, there is shown a schematic fluidic diagram of an automated supercritical fluid extraction system 10B similar to the supercritical fluid extraction systems 10 (FIG. 1) and 10B (FIG. 3) having a pumping system 814, a fluid-extraction assembly 878, and a collection system 916.

To supply extracting fluid to the pumping system 814, the tank 802 communicates with the pumping system 814 through tubing 952, a manual valve 806 and a fitting 804 for the valve 806. The outlet of the valve 806 is connected to the inlet port 812 of the pumping system 814 through the tubing 810 which is connected to the valve 806 by fitting 808 and to the pump by another fitting not shown.

The outlet of the pumping system 814 communicates with the fluid-extraction assembly 878 through two different lines, the inlet valve system 956 (enclosed by dashed lines) and the wash valve system 954 (also enclosed by dashed lines). The pumping system 814 also communicates with the collection system 916 through the cooling valve system 958.

Prior to an extraction, a sample cartridege 870 is moved into the pressure chamber in the manner described above in connection with the embodiment of supercritical fluid extractor 10B (FIG. 3). The pump supplies clean extracting fluid from a source of extracting fluid to one port in the breech plug assembly so that it flows adjacent to the seals to clean them and out of the fluid extracting assembly 878. This fluid does not flow during extracting of a sample.

During an extraction the pump communicates with the sample cartridge 870 located in the fluid-extraction assembly 878 through the inlet valve system 956. The fluid flow path goes from the pump to tee connector 820 through tubing 960 which is connected by fittings 816 and 818. The first tee 820 is connected to a second tee 842 through tubing 838 and fittings 836 and 840.

One outlet of the second tee 842 is connected to an electrically-actuated valve 850 by tubing 846 which is connected using fittings 844 and 848. This electrically-actuated valve 850 is described in U.S. Pat. No. 5,173,188 issued Dec. 22, 1992, form application Ser. No. 07/847,652, filed Mar. 5, 1992, in the names of Robin R. Winter, Robert W. Allington, Daniel G. Jameson and Dale L. Clay, the disclosure of which is inco rporated by reference. The electrically-actuated valve 850 is connected to the inlet housing 868 through a coiled heat exchanger 854 and fittings 852 and 866. In FIG. 19, this heat exchanger, actually located in a recess in aluminum temperature control jacket 966, is shown removed for clarity. A heating element and temperature-sensing thermocouple (neither are shown) are imbedded in the jacket 966. A conventional temperature controller regulates the heating to control the temperature of the jacket and therefore the temperature of extraction vessel 1042.

Pressurized supercritical $CO_2$ is heated in the heat exchanger 854 and enters the extraction vessel 1042 and the interior of the sample cartridge 870. This fluid entry is from the top of the extraction vessel and sample cartridge through an inlet housing as will be explained in greater detail hereinafter.

The inlet housing splits the flow during the initial fill when the chamber is pressurized between the outside and the inside of cartridge 870. The inlet housing is sealed to prevent leakage and to prevent fluid from communication with the surroundings. Inside the cartridge 870 is a void space above the sample. After passing through the void space and sample the fluid enters a nozzle of the breech plug below the cartridge 870.

During extraction there is no fluid flow in tubes 864 or 882 used to clean the breech plug seals as briefly described above. The fluid from the extraction cartridge enters an opening in the nozzle of the breech plug 1010 and proceeds up and around the upper seal and down and around the lower of the seals that seal the breech plug to the pressure vessel. This design eliminates any dead space and, hence, extractant loss. The fluid flow is sufficient to wash out the seals in less than a minute with clean fluid.

A washout port is provided for this purpose. This port communicates directly with the pumping system 814 through the wash valve system 954. This wash valve system 954 communicates with pumping system 814 through the second tee 842. This tee is connected to an electrically-actuated valve 860 by tubing 962 and fittings 858 and 856.

The connection from the valve 860 and the wash out port is provided by a heat exchanger 864 which is actually, physically, located in a recess (not shown) in aluminum temperature control jacket 966. This heat exchanger is connected by fittings 862 and 872. The heat exchanger is made of $\frac{1}{16}$" tubing with 0.005 I.D. This small inside diameter is to reduce the volume of the tube to minimize fluid and extract from becoming trapped inside during the extraction cycle when the wash valve is closed.

During washing, valve 850 is closed and fluid in the radial passage within the breech plug 1010 is stationary. Fluid 1022 (FIG. 20) entering the wash port 1046 is directed to the same point 1024 that the fluid from the cartridge reaches just before it diverges to pass over the inner surfaces of the seals. From this point, whether the fluid is from the wash port or cartridge the flow path is the same. The fluid flows through the seals in a split circular path as will be described better in connection with FIG. 21. The fluid converges and exits through the outlet port at fitting 874, the valve 904 and to the collection system. This washing takes place after each extraction to prevent cross-contamination.

After the extraction is complete, valves 850, 860 and 904 are closed. The fluid in the pressure vessel chamber remains stagnant until the pressure is released by vent valve 894. This valve is an electrically-actuated valve and is connected to the chamber through tubing 882 with fittings 876 and 884, and to the over pressure safety diaphragm 886 with tubing 890 and fittings 888 and 892. The fluid is then routed away from the unit to a point of safe disposal through tubing 898 which is connected to valve 894 by fittings 896. The fluid exiting the tube is a gas.

The fluid exiting the outlet port for extractant is routed to restrictor 912 in the collection system 916. Located along this path is tubing 880 which connects the outlet port to the electrically-actuated outlet valve 906 through fittings 874 and 914. The fluid is then routed to a filter 910 by tubing 908 which is connected using fitting 906. Fluid passes through the filter and then through the restrictor 912 which is inserted into vial 914.

The extractant is partitioned within the collection solvent in the vial 914 and the gas leaves through tubing 926. A septum retains gas pressure in the vial and the port maintains pressure with the backpressure regulator 920.

Figure 20:
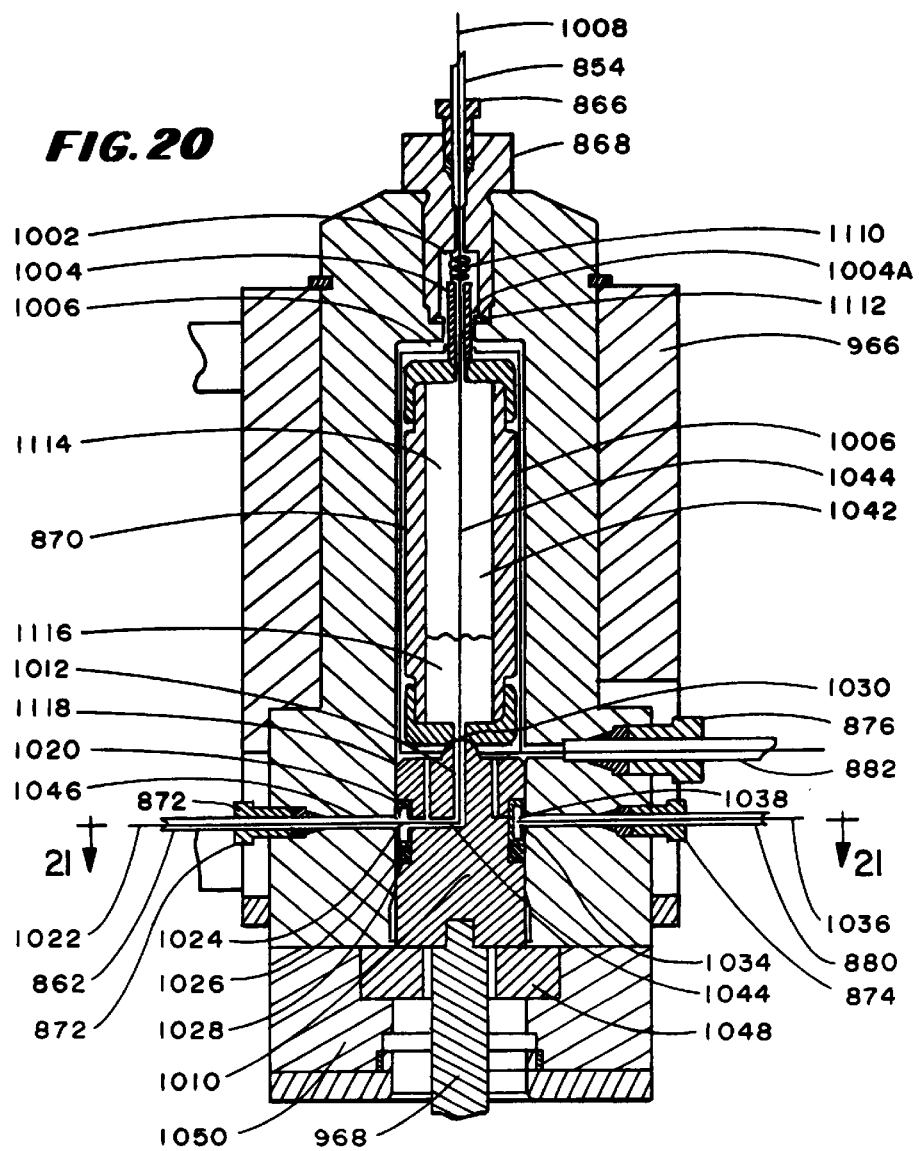
FIG. 20 is a sectional view of one embodiment of extraction chamber, cartridge, breech plug, and flow splitter.

In FIG. 20, there is shown a fragmentary sectional view of the fluid extraction assembly 878 having as its principal parts the cartridge 870, an outlet port at fitting 876 connected to tubing 882, an extracting fluid inlet port fitting 866, a cleaning inlet port fitting 872 and a pressure vessel cleaning fluid outlet port fitting 876.

In operation, pressurized supercritical $CO_2$ is heated in the heat exchanger 854 and enters: (1) the outer chamber space 1006 between the pressure vessel walls and the cartridge through tubing 1008; and (2) the interior 1014 of sample cartridge 870. This fluid entry is through inlet housing 868.

The inlet housing 868 splits the flow during the initial fill when the chamber is pressurized. The flow is split between the outside 1006 and the inside 1014 of cartridge 870. The flow splitter consists of a chamber 1002 inside the inlet housing 868, a spring 1110, and a nozzle 1004. The inlet housing 868 is sealed to prevent leakage and to prevent fluid from communication with the surroundings by a washer seal 1112.

In the preferred embodiment, the seal is made from a soft metal such as copper. The spring 1110 forces the nozzle 1004 against the cartridge and prevents direct communication of fluid between the inside 1014 and space 1006 outside of the cartridge. However, during initial pressurization the nozzle 1004 splits the fluid flow between the inside and outside of cartridge 870 by passing some of the fluid through its center and the rest along slits 1004A along its length on the outside.

The point at which the fluid splits is in a small chamber 1002 located in the inlet housing. The fluid then passes between the nozzle 1004 and washer seal 1112 before entering the chamber space 1006. The design is such that the pressure between the inside and outside of the cartridge is nearly equal at all times. Before and during extraction there is no fluid outflow through tubing 882. The fluid in the space 1006 is static or stagnant during extraction.

Inside the cartridge 870 is a void space 1014 above the sample 1016. After passing through the void space 1014 and sample 1016 the fluid enters the nozzle 1030 of the breech plug 1010.

The breech plug assembly consists of the breech plug 1010, lower seal 1026, seal spacer 1034, upper seal 1020, outlet port or point 1038 and a port tube 1012. During extraction there is no fluid flow in tubes 864 or 882. The fluid from the extraction cartridge enters an opening in the nozzle 1030 of the breech plug 1010 and proceeds through the port tube 1012 which is press fit into breech plug 1010.

The port tube 1012 transports the fluid to the center 1024 of the upper and lower breech plug seals 1020 and 1026. It also locks the orientation of the seal spacer 1034. There are two openings in the seal spacer, one at the port tube 1012 and the other near the outlet port or point 1038. The fluid diverges at point 1024 into a four way split flowing up and around the upper seal and down and around the lower seal. The seal spacer 1034 takes up the space between the seals, thereby forcing the fluid into the seals. This design eliminates any dead space and, hence, extractant loss. The fluid flow is sufficient to wash out the seals in less than a minute with clean fluid.

A washout port is provided for this purpose. This port communicates directly with the pumping system 814 through the wash valve system 954 (FIG. 19). This wash valve system 954 communicates with pumping system 814 through the second tee 842. This tee is connected to an electrically-actuated valve 860 by tubing 962 and fittings 858 and 856.

Figure 21:
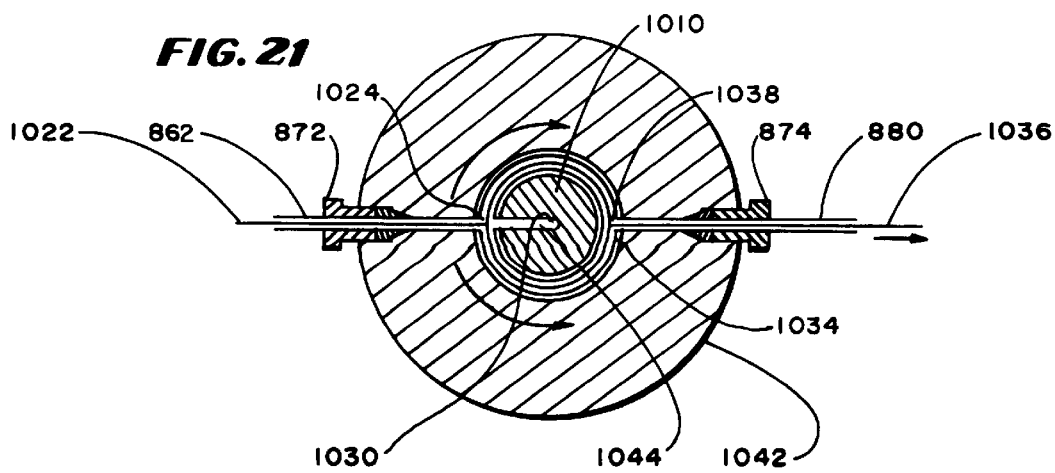
FIG. 21 is a sectional view of the chamber of FIG. 20 taken through lines 21—21 in FIG. 20.

During washing, valve 850 is closed and fluid in passage 1044 is stationary. Fluid 1022 (FIG. 20) entering the wash port 1046 is directed to the same point 1024 that the fluid from the cartridge will reach just before it diverges to pass over the inner surfaces of the seals. From this point, whether the fluid is from the wash port or cartridge the flow path is the same. The fluid flows through the seals in a split circular path as can be seen in FIG. 21 and converges at point 1034. From here it exits through the outlet port 1038 and to the collection system. This washing takes place after each extraction to prevent cross-contamination.

After the extraction is complete, valves 850, 860 and 904 are closed. The fluid in chamber 1006 remains stagnant until the pressure is released by vent valve 894. This valve is an electrically-actuated valve and is connected to the chamber through tubing 882 with fittings 876 and 884, and to the over pressure safety diaphragm 886 with tubing 890 and fittings 888 and 892. The fluid is then routed away from the unit to a point of safe disposal through tubing 898 which is connected to valve 894 by fittings 896. The fluid exiting the tube is a gas.

The fluid exiting the outlet port is routed to restrictor 912 in the collection system 916. Located along this path is tubing 880 which connects the outlet port to the electrically-actuated outlet valve 906 using fittings 874 and 914. The fluid is then routed to a filter 910 by tubing 908 which is connected using fitting 906. Fluid passes through the filter and then through the restrictor 912 which is inserted into vial 914.

In FIG. 21, there is shown a sectional view through lines 21—21 of FIG. 20 showing the seals between the breech plug 1010 and the extraction vessel 1042 and the wash or cleaning inlet port and outlet port at fittings 872 and 874 respectively. The arrows show the circulating of the wash fluid from point 1024 in counterclockwise and clockwise directions between the upper and lower seals from the fitting 872 and out of the fitting 874.

Figure 22:
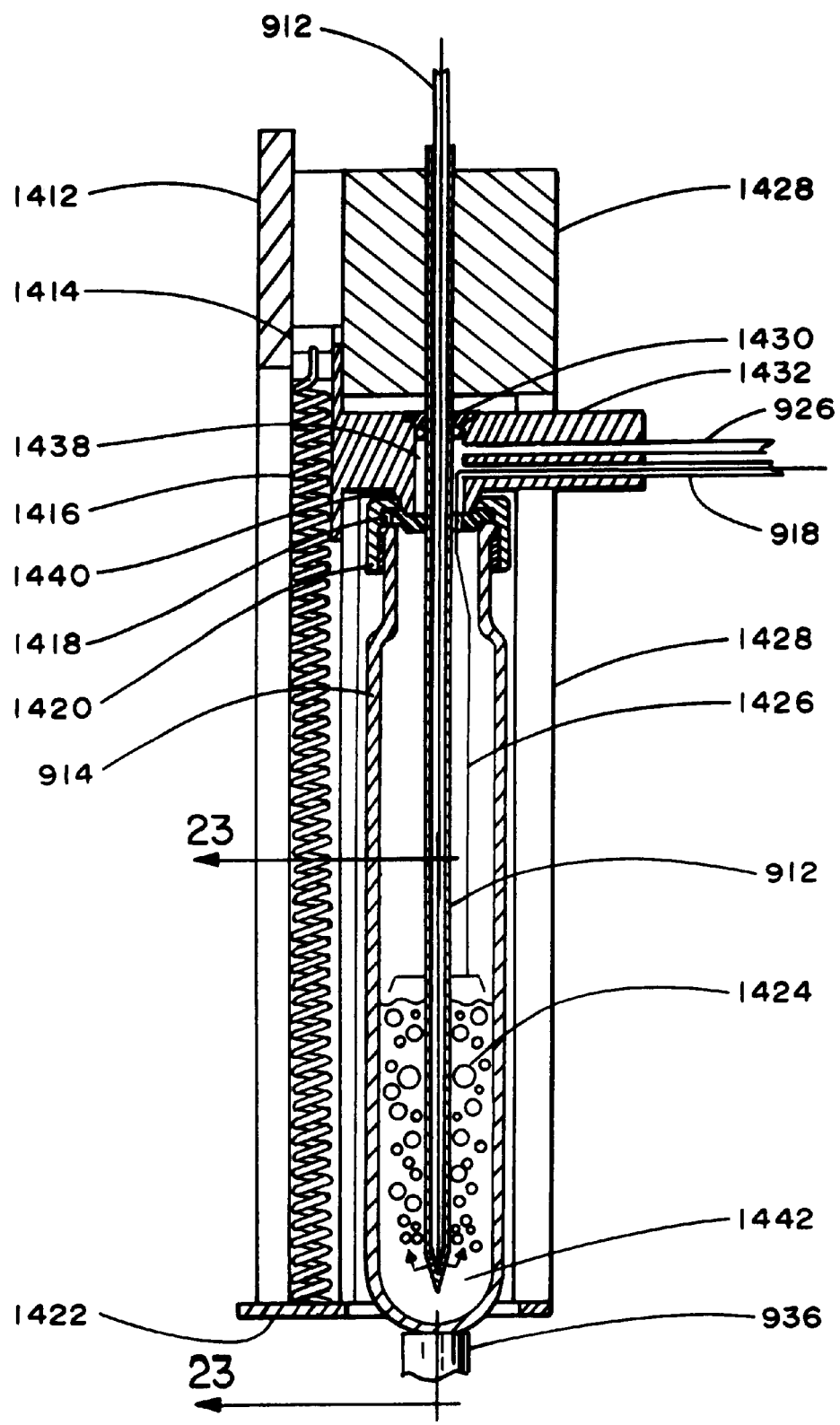
FIG. 22 is a sectional view of the vial septum piercing and solvent collection system assembly.

In FIG. 22, there is shown a fragmentary sectional view of the collection system 916 having as its principal parts a restrictor 912, a solvent 1442, a push tube 936, a vial 914, solvent port or tubing 926 and septum 1418. The fluid containing extract flows through restrictor 912 and exits as a gas at the bottom of vial 914. The expanded gas bubbles 1424 rise upward through solvent 1442 leaving the extract behind in the solvent.

The gas 1426 above the solvent continues rising and passes through a slit in the septum 1418. The septum is held to the mouth of vial 914 by vial cap 1420. The slit in the septum provides a passage for the restrictor. The septum is made of silicone rubber or other flexible, elastic material with a Teflon backing. The restrictor opens the slit in the septum in such a manner that an opening is formed on both sides of the restrictor through which the gas exiting the vial passes. Gas enters a large opening 1438 in the vial guide 1432. The vial guide is sealed against the septum by spring 1416. The other end of spring 1416 is anchored to bottom piece 1422. The large opening 1438 is also sealed by a flange seal 1430 around the restrictor.

The restrictor 912 may be a capillary tube restrictor formed of stainless steel tubing, available from Sterling Stainless Tube Corporation of Englewood Colo. Typical useful solvents are liquid dichloromthane and liquid isopropanol. The septum is make of silicone rubber or other flexible elastic material with a Teflon backing (Teflon is a trademark for tetrafluoroethyline fluorocarbon polymers sold by DuPont de Numours, E. I. and Co., Wilmington, Del., 19898).

This design prevents the gas from communicating with the surroundings. The gas passes through tube 918 to a back-pressure regulator 920 (FIG. 19). This regulator causes pressure to build inside the collection vial and decreases collection solvent and extract losses. Misting is essentially eliminated. Also, elevated pressure minimizes the violent bubbling that occurs and allows the amount of solvent to be measured.

A pressure of 40 to 50 psig is satisfactory, as are other pressures in the range of 20 to 200 psi. The gas leaving regulator 920 is routed to a proper disposal point through tubing 922. Also, the vial guide is designed such that if the pressure exceeds a safe value the pressure forces vial guide 1432 up and breaks the seal. This prevents the pressure from exceeding the safety limit of the glass collecting vial. Nevertheless, the vial is located in an enclosure to decrease the risk due to its shattering from the pressure. Control of collecting vessel temperature by refrigerated bath and control of vessel pressure by multiple, manually operated, needle valves is described by Nam, et al. Chemosphere, 20, n. 7–9, pp. 873–880 (1990).

Although the slitted septum 1418 is not entirely air-tight when the vial 914 is lowered from restrictor 912 and placed in the vial rack (not shown), the septum substantially prevents evaporation of collection solvent and extract when the vial is in the vial rack. The slit tends to re-close.

If additional solvent is needed in the vial, some may be pumped in from a reservoir 932 using pump 928. The fluid is pumped from the reservoir 932 through tubing 930 and then to the vial guide through tubing 926. The fluid enters the opening 1438 inside the vial guide 1432. It then enters the interior of the vial through the same openings in the septum slit from which the gas escapes.

Elevated pressure and reduced temperature generally increases trapping efficiency. Therefore, a provision for precooling and maintaining the collection solvent temperature is provided. Also, low collection solvent temperature may create a problem with restrictor plugging and ice formation.

Figure 23:
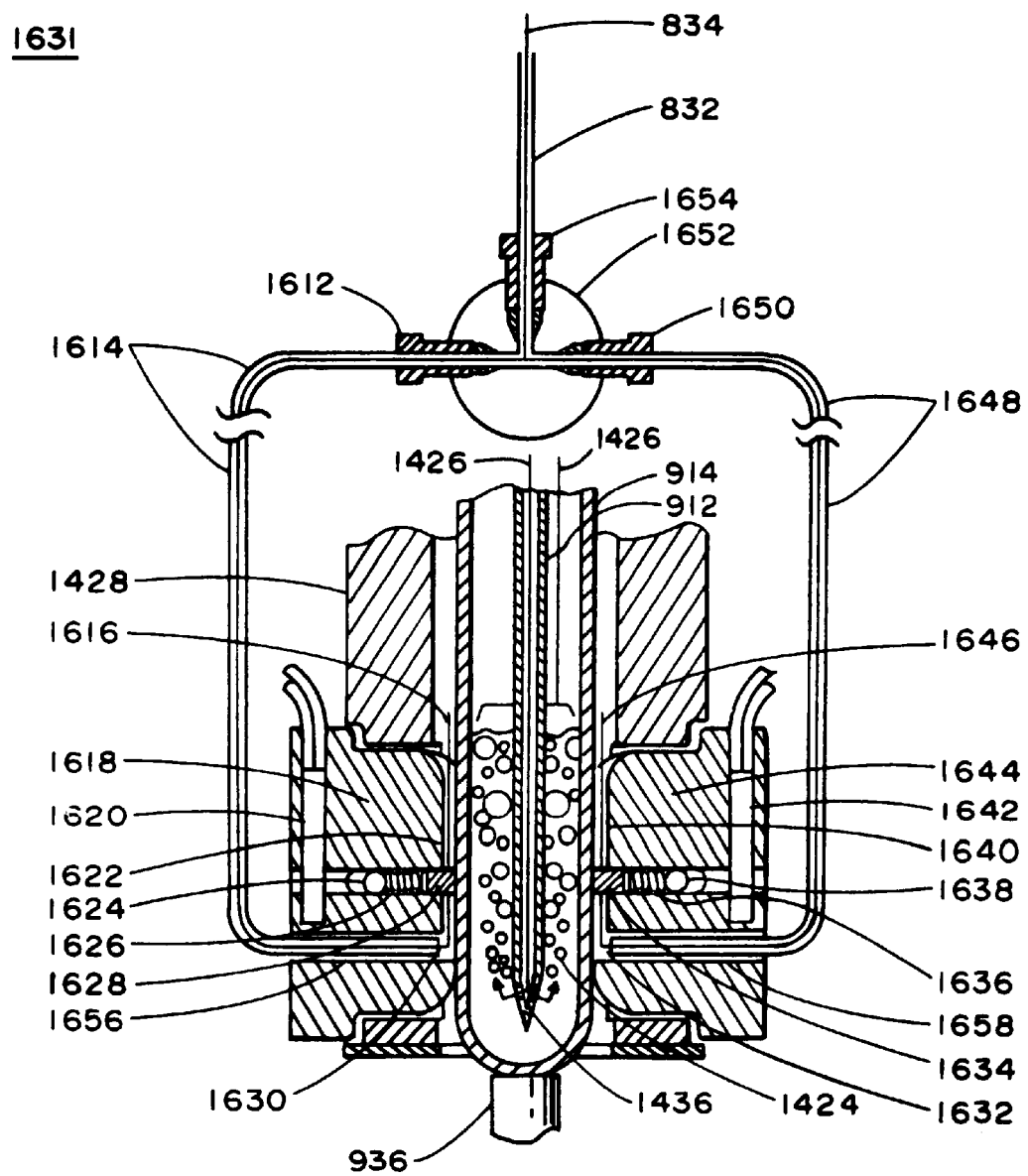
FIG. 23 is another sectional view of the piercing and solvent collection system assembly taken through the vial heater and cooler.

In FIG. 23, there is shown a heating and cooling device 1631 having as its principal parts cooling lines 1614, 1648 and 832, blocks 1618 and 1644 and electric heaters 1620 and 1642. The heaters and coolers are arranged to be selectively in thermal contact with the collection vial 914.

For this purpose, lines 1614, 1648 and 832 communicate with the pump through the valve cooling assembly 958 (FIG. 19). This assembly is connected to the first tee 820. The connection is made by tubing 824 which is attached to the electric valve 828 by fittings 822 and 826. This valve is then connected to another tee 1652 located above the collection system.

This connection is made by tubing 832 and fittings 830 and 1654. Fluid 834 enters tee 1652 and is split in two directions. The fluid then flows through two restrictor cooling tubes 1614 and 1648 which are attached to the tee by fittings 1612 and 1650. This pair of restrictors must be made of a flexible material and the preferred embodiment is stainless steel capillary. Vaporization of liquid $CO_2$ supplied by line 832 cools the collection vial 914 and its contents. Each restrictor provides the same function to opposite sides of the vial. Therefore, each component which controls the temperature of the vial is duplicated on either side.

The blocks 1618 and 1644 to which the restrictor cooling tubes are routed, are spring-clamped onto opposite sides of the vial. These blocks are located in the collection system housing 1412. This housing is preferably made of a non-heat-conducting material such as plastic. Each block is attached to the housing by spring pins, 1624 and 1638. The opening in the block in which the pin passes through are slots. This allows the blocks not only to move toward and away from the vial but to rotate as well. This allows the blocks to be forced out of the way by the vial as it is lifted into position. The rotation makes it easier for the blocks to clear the vial cap 1420 which is larger than the vial 914. Without rotation the blocks may bind when the vial is lifted.

The blocks 1618 and 1644 are forced against the vial by spring 1626 and 1636. These springs are larger than the slots and are inserted in an opening in the side of each block and held in place by set screws, 1628 and 1634. The blocks 1618 and 1644 are made from aluminum which transfers heat from the electric heaters 1620 and 1642 which are also located in the blocks.

Heat is transferred by conduction from the heaters to the surface of the vial. The heaters 1620, 1642 and the $CO_2$ supply valve 828 are controlled by a conventional temperature controller equipped with a thermocouple (not shown) in thermal contact with liquid-filled portion of the vial 914.

To cool the vial, the cooling lines are routed into openings 1656 and 1658 in the blocks. These openings go all the way through the block and allow the cold $CO_2$, which exits the restrictor capillary tubing at points 1630 and 1632, to be directly against the vial. There are small grooves, 1622 and 1660, located along side of the blocks. They form pathways which guide the $CO_2$ along the sides of the vial to increase cooling. The $CO_2$ gas at points 1616 and 1646 is vented to the surroundings and is driven away by natural or forced air convection. This produces the maximum amount of cooling in the least amount of time since this technique does not require that the blocks be cooled before vial cooling begins.

The vial 914 is raised by vial lift 942. This is best illustrated in FIG. 19. The gear motor 944 drives gear 946. This gear is attached to the drive screw 940. The drive screw is held in place by bearing 948. As the drive screw rotates, rotational motion is translated into linear motion by guide nut 938. This nut is attached to the push tube 936 which in turn lifts the vial. The guide nut is prevented from rotating by the guide rod 952 which is anchored top and bottom. The push tube 936 is guided by a linear bearing 934.

After extraction, fluid is discharged from the chamber region 1006 through tube 882, past overpressure blowout plug safety device 886, valve 894 which is opened at this time, and atmosphere vent tube 898. The blowout safety device 886 is always in communication with the chamber 1006, and incorporates a blowout disc that ruptures at a pressure of 12,500 psi. This protects the extraction vessel 1042 (FIG. 20) from dangerous rupture, as it is designed to hold a pressure in excess of 50,000 psi. The normal maximum operating pressure within the extraction vessel 1042 is 10,000 psi.

In order to achieve down flow in the automated unit, the $CO_2$ inlet and a flow splitter must be relocated to the top of the chamber. These devices must fit within the confines of the upper section of the chamber and are contained in an assembly which consists of an inlet housing, spring, nozzle and seal washer. This flow splitter assembly allows the pump to communicate with the inside and outside of the extraction cartridge. The nozzle and spring are captivated in the housing by the seal washer and the nozzle and spring are positioned as such that the spring forces the nozzle out of the housing and into the chamber.

When a cartridge loaded into the chamber compresses the nozzle back into the housing, the force from the spring creates a seal between the nozzle and the cartridge. This prevents fluid in the outer chamber space 1006 from entering the cartridge unless it diffuses through the tortuous path back up around the outside of nozzle 1004.

The washer seal which holds the nozzle in place also seals the housing and prevents fluid from leaking to the outside environment. During an extraction, the fluid enters the housing 868 and flows through a pathway to cavity 1002 where the spring and nozzle are located. From this cavity, the fluid can communicate with either the cartridge or the chamber. The nozzle has a pathway through its center which directs fluid from the cavity to the inlet of the cartridge. Also, there is a slit down the side of the nozzle which creates a pathway from the cavity to the chamber. This design is such that the pressure will remain the same inside and outside the cartridge when filling and during extractions.

After the fluid has passed through the cartridge, and hence the sample, it contains extract from that sample. The fluid must pass through an opening in the breech plug, flow across the seals and exit through the outlet port. During extraction the seals are constantly swept by extraction fluid carrying progressively less and less extract. This prevents accumulation of extract on the seals. Therefore, this flow path must not have any dead space or stagnant regions.

To avoid dead space, the outlet port in the breech plug is oriented 180 degrees from the outlet port of the chamber. This forces the fluid to sweep around the full circumference of the seals. There is a tube 1012 pressed into the outlet port of the breech plug which directs the fluid to the center of the seals. The fluid is forced up into the seals by the seal spacer 1024 which is located between the seals 1020 and 1028. The fluid diverges into four different directions and converges at the chamber outlet port.

To ensure that the seals are clean, a washout port is provided. This port communicates with the pump and delivers clean fluid to the same point that the outlet of the breech plug does. This clean fluid from the pump washes not only the seals but all the tubing including the restrictor which is located downstream.

The collection vial is lifted into the collection system assembly by the vial lift, cooled to a preselected temperature, and then heated or cooled (if necessary) to maintain that temperature. Also, the vial is sealed such that pressure may be maintained and controlled in the vial, and gases are vented to a proper location.

The vial lift mechanism operates independently from the sample cartridge lift which allows vials to be changed at any time during or after the extraction process without depressurizing the extraction chamber. This mechanism is driven by a gear motor and consists of the motor, drive screw, guide nut, and push tube. The drive screw and guide nut converts the rotation of the motor to linear motion which then lifts the vial to the collection assembly.

This collection assembly contains a vial guide, flanged restrictor seal, spring, stationary restrictor, and a collection system housing 1412. The restrictor is anchored by block 1428 to the housing and is centered over the vial. The vial guide is restrained by the assembly housing but is designed such that it may slide up and down its length. There is a large opening in the guide that contains a flanged seal 1430 that the restrictor passes through as the guide moves. This seal and the seal provided by the truncated cone 1440 bearing against septum 1418 prevent communication of gases and vapors in the large opening with the surroundings.

Before the vial is lifted up, the vial guide 1432 has been pulled near the bottom piece 1422 (FIG. 22) by the action of tension spring 1416. The vial first comes into contact with truncated cone 1440 located on the vial guide. This cone enters the hole in the top of vial cap 1420 and causes the vial to center itself on the vial guide before the stationary restrictor becomes inserted through the vial septum 1418.

The septum is held in place by a vial cap 1420 and has a slit which allows the restrictor to pierce through and then close up when it is removed. When there is no vial in the collection system, housing tension spring 1416 pulls down vial guide 1432. The vial lift raises the vial until it contacts the lowered vial guide. Then it lifts both the vial guide and the vial until they have reached the proper location which is when the stationary restrictor is about 0.25 inches from the bottom of the vial, as shown in FIG. 23. The spring 1416 connected between the guide and housing forces the guide down onto the vial septum thereby creating a seal between the two. This seal and the seal 1430 around the restrictor allows pressure to build up in the vial.

The vial guide has 5 basic functions, which are: (1) it guides the vial to the proper position; (2) its spring forces the vial off of the restrictor and back into the vial rack when the vial lifter lowers the vial and this prevents the vial from catching in the collection assembly if it is covered with frost due to cooling; (3) it seals against the vial septum to the truncated cone 1440 and around the restrictor and this seal is capable of holding at least 50 psig; (4) it has a port for adding collection solvent to the vial; and (5) it has a port which vents the extraction gases and vapors.

The replenishment solvent port 926 intersects with the large opening 1438, which the restrictor goes through, on the vial guide. Collection solvent is pumped into the vial through this port from a reservoir. The solvent passes through the port, the large opening and enters the vial through a gap in the septum. This gap is created on either side of the round restrictor when the restrictor is pressed through the pre-made slit in the septum. The solvent is prevented from communicating with the outer environment by the seal between the septum and the vial guide, and also the seal around the restrictor.

The vent port, which intersects the large opening, is connected to a regulator that controls the pressure inside the vial. The gases coming from the restrictor exit the vial through the same slit and gaps around the restrictor that the solvent from the solvent port passes through. Then the gases pass through the large opening port and on to the regulator. From the regulator the gases and vapor are routed to a point of proper disposal.

The temperature of the vial is controlled by heaters and $CO_2$ expansion devices imbedded in two aluminum blocks. These blocks are spring loaded against the vial and are curved on the mating surface such that there is full contact with the vial walls. Also, they are held in place by a pin anchored to the collection system housing. This pin passes through a slot in the blocks and a spring located between this pin and the block is what forces the block against the vial. This pin and slot arrangement enables the blocks to float over the vial cap and vial by rotating as well as move in and out.

The heaters imbedded into the block heat the vial by conduction through the aluminum block. The cooling lines, which communicate with either a $CO_2$ tank or pump, are inserted into an opening in each block which passes all the way through to the vial. This arrangement allows the $CO_2$ to expand from the cooling lines and come into direct contact with the vial without having to cool the entire heating block first. The vial housing, which contains the blocks, is made of plastic which resists heat transfer thereby reducing the thermal mass which is heated or cooled to reach the desired temperature.

The parameters that are controlled for the extraction process include the chamber and heat exchanger temperature, the collection solvent temperature and collection vial pressure, the extraction time and extraction pressure, the wash time and whether multiple vials are needed for the extraction. A conventional microprocessor collecting controller provides all of the control functions.

Prior to the start of an extraction sequence, the valves, refill valve 806, cooling valve 828, inlet valve 850, wash valve 860, and outlet valve 904 are closed. The only exception is the vent valve 894 which may be left open for now.

If the pumping system 814 is empty, the refill valve 806 is opened to allow the $CO_2$ cylinder 802 to communicate with the pumping system 814. The pump is then activated to refill. When complete, refill valve 806 is closed and pumping system 814 is switched to run and is pressurized to the desired extraction pressure.

A vial 914 and cartridge 870 are lifted into position in the manner described previously. A sample cartridge 870 is lifted into position by cartridge elevator 808 which supports Nitronic 60$^R$ breech plug 1010. The breech plug is locked in place by a Nitronic 60 split locking bar 1048 which locks and unlocks through motion perpendicular to the plane of FIG. 20. The operation is similar to that of the locking mechanism of a Winchester model 94 rifle. The locking bar is captivated to the extraction vessel 1042 by slotted plate 1050. The plate 1050 and vessel 1042 are made of 17-4 PH stainless steel hardened to H1050. The material choices of 17-4 PH and Nitronic 60 are made for strength, corrosion resistance and resistance to galling.

After the pumping system 814 is pressurized, the vent valve 894 is closed and the inlet valve 850 is opened. The pumping system 814 now communicates with the chamber 1042 and pressurizes chamber 1042, the interior 1014, 1016 of cartridge 870 and its exterior 1006 through the flow splitter 1002, 1004, 1110.

While the chamber 1042 is pressurizing, the vial 914 may be cooled if desired. If so, the cooling valve 828 is opened allowing the pumping system 814 to communicate with the cooling restrictors 1614 and 1648. The vial 914 will continue to be cooled until it reaches the selected temperature. At this time the heaters 1620 and 1642 may be turned on by their associated temperature controller to regulate this temperature, unless a very low temperature is selected.

When the pumping system 814 has pressurized the chamber 1042 to its selected pressure, the outlet valve 894 is opened. The pumping system 814 is now communicating with the restrictor and hence the vial 914. The fluid flows through the heat exchanger 854, is heated to supercritical temperature, and enters the cartridge at a selected supercritical temperature. After passing through the sample 1016 the fluid proceeds to the restrictor 912 through the breech plug 1010 and seals 1020 and 1026. At the vial 914 the pressure builds due to the pressure regulator 920 located downstream of the vent port. When the preset, regulated pressure inside the vial is reached, the gas and vapors will proceed to a disposal point.

If during the extraction, additional collection solvent is needed in the collection vial 914, a pump 928 is activated and fluid is pumped from reservoir 932 to the vial 914.

This extraction process continues for the preselected time interval and at the end the process is either terminated and a new cartridge 870 and vial 914 are loaded or only vial 914 may be changed along with any of the extraction parameters such as temperature and pressure. If the latter is chosen, the outlet valve 904 is closed and the wash valve 860 is opened for a preselected interval. At the end of the wash interval, wash valve 860 and outlet valve 904 are closed and the vial 914 is lowered and a new one inserted in a manner described previously. At this time the outlet valve is reopened if all the parameters are stabilized.

When the sample cartridge has been extracted, a new vial 914 is selected, which may be a wash vial. A group of several wash vials may be used in sequence after each collecting vial. For each, the wash valve 860 is opened for another preselected interval and the vial loading and unloading process is repeated until the new collection vial is loaded. The same group of wash vials can be used to wash all of the collecting vials because the dilution of contaminants is exponential for each wash vial change.

After this cycle, when no further changing of vials is required, the outlet valve 904 and inlet valve 850 are closed and the vent valve 894 is opened for a length of time sufficient to vent the chamber. When the chamber is at atmospheric pressure the sample cartridge 870 and vial 914 are unloaded and unit is ready for the extraction sequence to be repeated on another sample.

The embodiment of FIGS. 19–23 may be modified to provide a variable restrictor similar to the variable restrictors of FIGS. 7–13. In such a modification, a simplified probe assembly and point restrictor similar to that disclosed in FIG. 8, but much simplied, is used instead of a restrictor tube such as the restrictor 912.

In this modification the adjustable orifice at 1240 is formed and controlled differently so as to avoid the need for the needle tip 1257 and the mechanism that adjusts its position with respect to the barrel tip 1233 to control the pressure in the extractor, the tubing between the extractor and the point restrictor and to control the rate of release and the expansion of effluent into the collection environment. In this modification, the point restrictor is formed between the end of the probe and the adjacent surface of the collection container.

The rate of release of effluent is controlled by adjusting the distance between the end of the probe and the bottom wall of the collection container. This distance can be adjusted by moving the push rod 936 up or down as described in connection with FIGS. 19, 22 and 23 while holding the probe stationary or by moving the probe such as with an electromagnet or screw drive with respect to the bottom wall of the collector container. The distance between the tip of the probe and the wall of the container controls the rate of release of the fluid from the probe.

Figure 24:
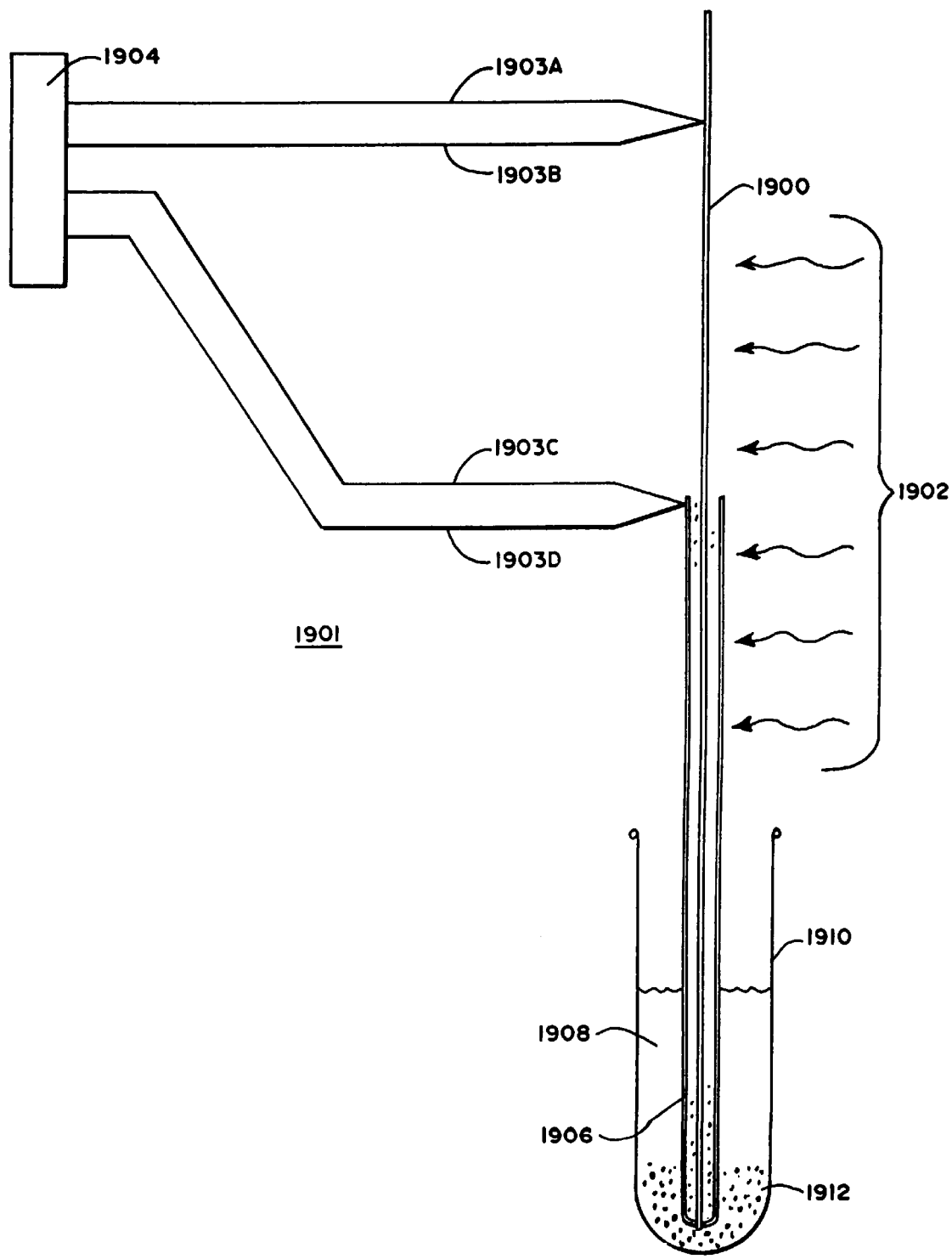
FIG. 24 is a schematic diagram of another embodiment of collection system.

In FIG. 24, there is shown a simplified schematic view of one embodiment 1901 of a novel collector assembly that may be used in the embodiments of FIGS. 1–24 having as its principal parts a capillary tube 1900 having a control channel 2003, a temperature sensing device 1904, thermally insulating sleeve 1906 and a collecting tube 1910. The capillary tube 1900 communicates with an outlet port of the extractor and extends through the thermally insulating sleeve 1906 into the cold collection trap 1908 within the collection tube 1910. Its temperature is sensed for control purposes by the temperature sensing device.

During collection the extractant within the capillary tube 1900 is preheated as a result of the extraction process. Because the tube passes through a coaxial insulating sleeve which extends into the cold collecting trap where the extractant is discharged, the extractant within the capillary tube 900 retains most of its heat as it flows through the capillary tube into the collection liquid.

Heat flow to the outlet end of the capillary is primarily carried by Joule heating from a longitudinal electric current provided along the length of the capillary but as also added by the current along the enthalpy in the fluid. In some embodiments, the capillary tube is metal and in these embodiments, especially if it is a high thermal conductivity metal such as nickel or molybdenum, the capillary tube or other restrictor does not have to be heated as far as its outlet end because the high thermal conductivity carries the heat to the end. In the preferred embodiment, the capillary tube 1900 may be made of Type 304 stainless steel. Suitable stainless steel tubes are available from Sterling Stainless Tube Corporation, Englewood, Colo.

In addition to the preheating caused by the hot fluid from the extractor, heat may be added to the extractant within the capillary tube from an additional external source before or while the the capillary tube is within the collection solvent to cause the capillary tube 1902 to be at the desired temperature at the point where it is measured by temperature sensing device 1904 and thus to cause the extractant to be within the desired temperature range when it enters the cold trap.

In the embodiment of FIG. 24, additional heat may be transmitted to the capillary tube 1900 through contact with hot fluid indicated as the arrows 1902 impinging upon the capillary tube. The hot fluid 1902 may be a gas such as air or a liquid such as a mixture of ethylene glycol and water. The fluid providing the heat is itself heated by conventional means, not shown in FIG. 1, to the desired temperature. This temperature is controlled by conventional feedback means (not shown) in accordance with the temperature sensed by temperature sensor 1904 and a temperature setpoint means. The temperature sensor 1904 senses the electrical resistance of the capillary tube 1900 and hence, through its temperature coefficient of resistance, its temperature. Resistance is sensed by the voltage-current method through Kelvin leads 1903A, 1903B, 1903C and 1903D.

The lower end of capillary tube 1900 is within thermally insulating sleeve 1906, which may be any material with low thermal conductivity and a high degree of chemical inertness. PEEK (a registered trademark of ICI) is a satisfactory material and may be utilized as a machined sleeve which is thermally shrunk onto the capillary for a tight fit or is injection molded onto the capillary with a conventional injection molding machine and a conventionally suitable mold. Coaxial insulating sleeve 1906 dips into collecting solvent 1908 contained within collecting tube 1910. Suitable collecting solvents often are dichloromethane or isopropanol. The wall of the sleeve 1906 is mechanically and electrically connected at 2012 to the outer wall of the capillary tube 1900 to seal the space between the capillary tube 1900 and the inner wall of the sleeve 1906 against the collecting fluid 1908 and provide a complete electrical circuit that includes the measuring device 1904 with the outlet 2001 of the capillary tube 1900 opening into the collecting fluid 1912.

During extraction, bubbles 1912 issue from the outlet end of the capillary tube 1900, which is flush with the lower end of sleeve 1906. The solvent 1908 dissolves the extract contained in the bubbles. The efficiency of removal of extract from the gas stream represented by bubbles 1912 is usually improved by lowering the temperature of solvent 1908 by means of a cooling means (not shown in FIG. 24) in thermal contact with collecting tube 1910. Efficiency of collection for collection of relatively highly volatile extracts is also improved by operating the interior of collecting tube 1910 under positive pressure. Such pressurization means and cooling means are not shown in FIG. 24.

The insulation type and thickness is selected to reduce the heat added to the extractant to a minimum and yet cause the temperature of the extractant to be within the desired range so that it is sufficiently hot to prevent it or its compenent parts from freezing or depositing within the capillary tube but is not so hot as to reduce the partitioning between the extract and the extractant so as to cause extract to bubble away with extractant. Pressurizing the collection tube permits a higher temperature to be used. Generally the thickness of the insulation will be in the range of 0.001 inches to one-quarter inch. The thermal conductivity is generally no greater than 50 British thermal units (Btu's per hour, per square foot, per inch for 1 degree Fahrenheit.

Figure 25:
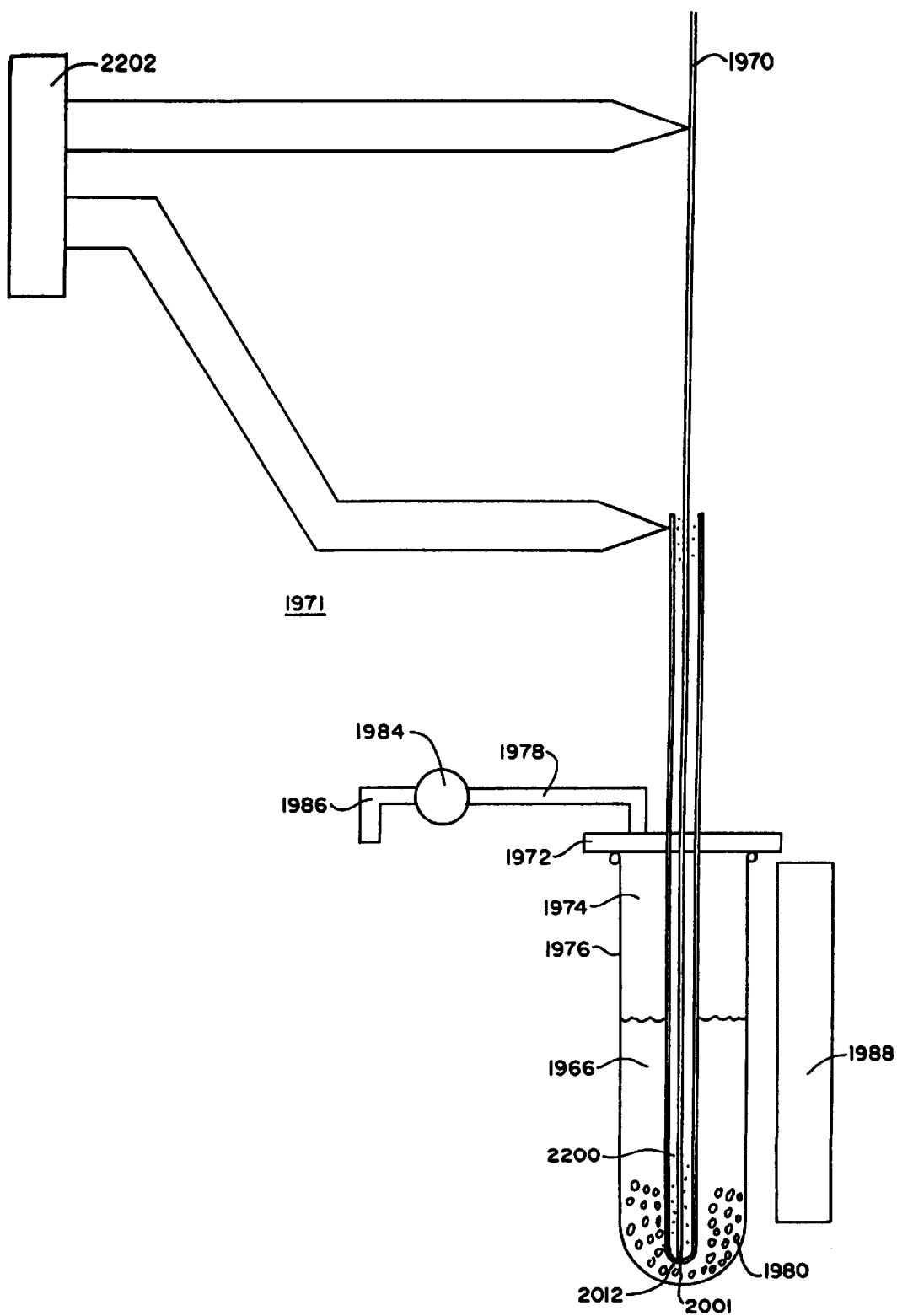
FIG. 25 is a schematic diagram of still another embodiment of collection system.

In FIG. 25, there is shown a simplified schematic view of still another embodiment 1971 of extractor having as its principal parts a capillary tube 1970, a temperature sensing device 2202, thermally insulating sleeve 2200 and a collecting tube 1976. The capillary tube, temperature sensing device, thermally insulating sleeve and collecting tube are substantially the same as the corresponding parts of the embodiment 1901 of FIG. 27 and operate in the same manner.

In FIG. 25, there is shown means for applying positive pressure to the collecting solvent 1966. A collecting solvent such as dichloromethane or isopropanol is usually satisfactory. As in FIGS. 24 through 34, heating element 1968 controls the elevated temperature of capillary restrictor tube 1970 and its fluid contents. Gas tight cover 1972 encloses the space 1974 above collecting solvent 1966 contained in collecting tube 1976. Gas tight ports in cover 1972 allow passage of capillary tube 1970 and gas removal tube 1978. The capillary tube 1970 is immersed in collecting solvent 1966.

Bubbles 1980 exiting the capillary tube raise the pressure in space 1974. This pressure is communicated by tube 1978 to backpressure regulator 1984. When the pressure in space 1974 reaches the setting of backpressure regulator 1984, the regulator starts to open and discharges gas from the extractant through discharge tube 1986.

By properly adjusting the setting of regulator 1984, a pressure for optimum collection efficiency within the collecting tube 1976 is established. Typical pressure settings range from 200 psi down to 5 psi. Cooler 1988 in thermal contact with tube 1976 sets a reduced temperature in the collecting liquid solvent 1966 as described in FIG. 34. Temperature and pressure control of a collection vessel is disclosed in Nam, et. al, *Chemosphere*, 20, No. 7–9, pp. 873–880 (1990). Nam's disclosure does not provide for heating of a restrictor nor for regulated control of pressure. Neither is there disclosure of insulation of the restrictor.

Figure 26:
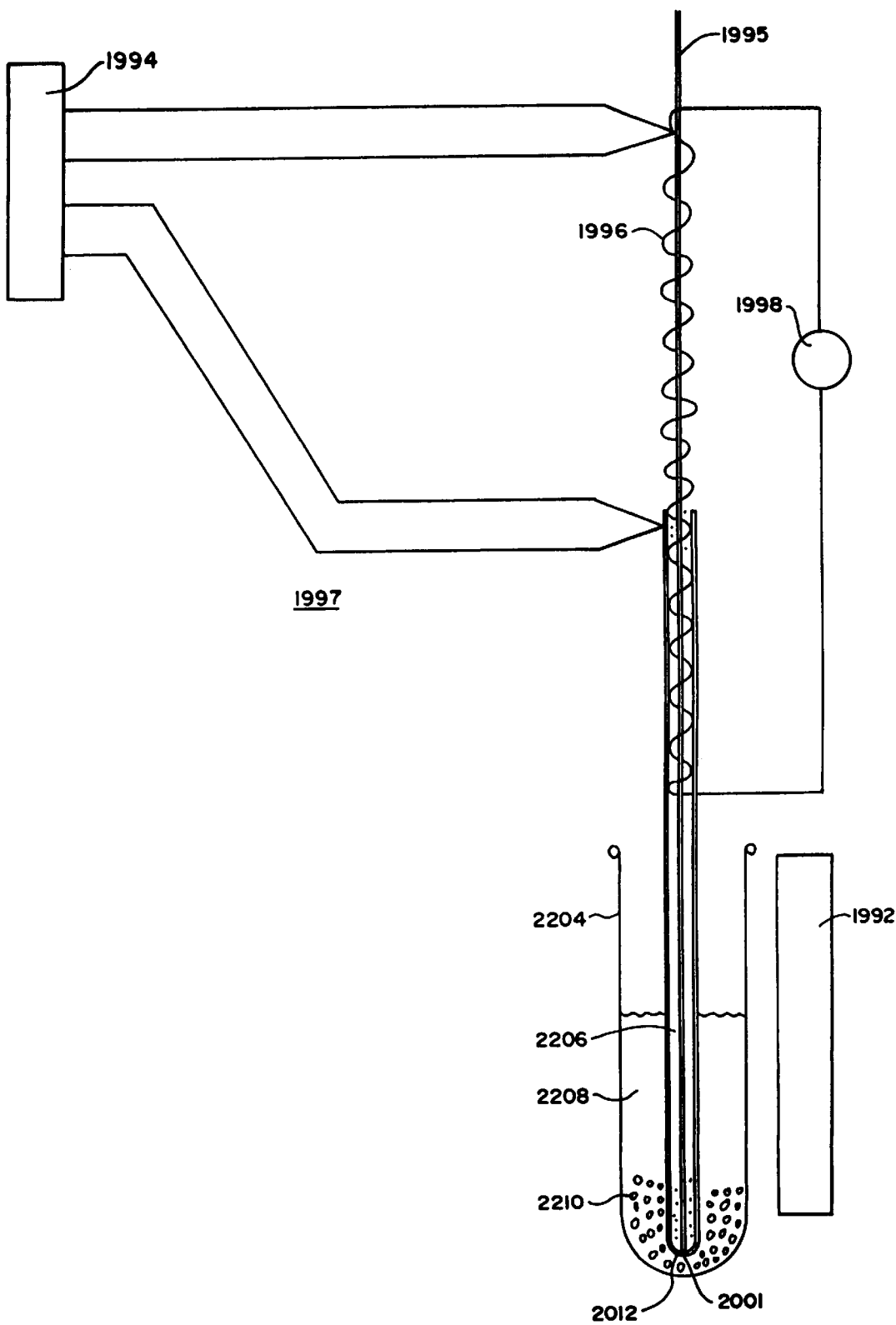
FIG. 26 is a schematic circuit diagram of still another embodiment of collection system.

FIG. 26 shows a temperature control mechanism similar in concept to that of FIG. 34. Instead of using the electrical resistance of the capillary tube 1952 as the heating element, a helical coil of resistance wire 1996 is wrapped around the capillary tube instead. This is advantageous when the capillary tube is not an electrical conductor. It is not necessary that the heating element 1996 be wrapped as a helical coil around the capillary tube. It may be disposed as a coil beside the capillary tube, or disposed in a zigzag pattern beside the capillary tube, or in a straight line beside the capillary tube, etc. In any event, the heater should be in thermal contact with the capillary tube. As in FIG. 25, temperature sensing element 1992 cools the collecting fluid. Temperature sensor 1994 is connected to a conventional temperature controller (not shown) which sets the voltage or current produced by direct current or low frequency alternating source 1998 which effects the heating of heating element 1996. This provides for controlling the temperature of the capillary and the fluid contained within it at the location of temperature sensing element 1994.

The preferred embodiment of this invention consists of two coaxial stainless steel tubes separated by an insulating layer.

Figure 27:
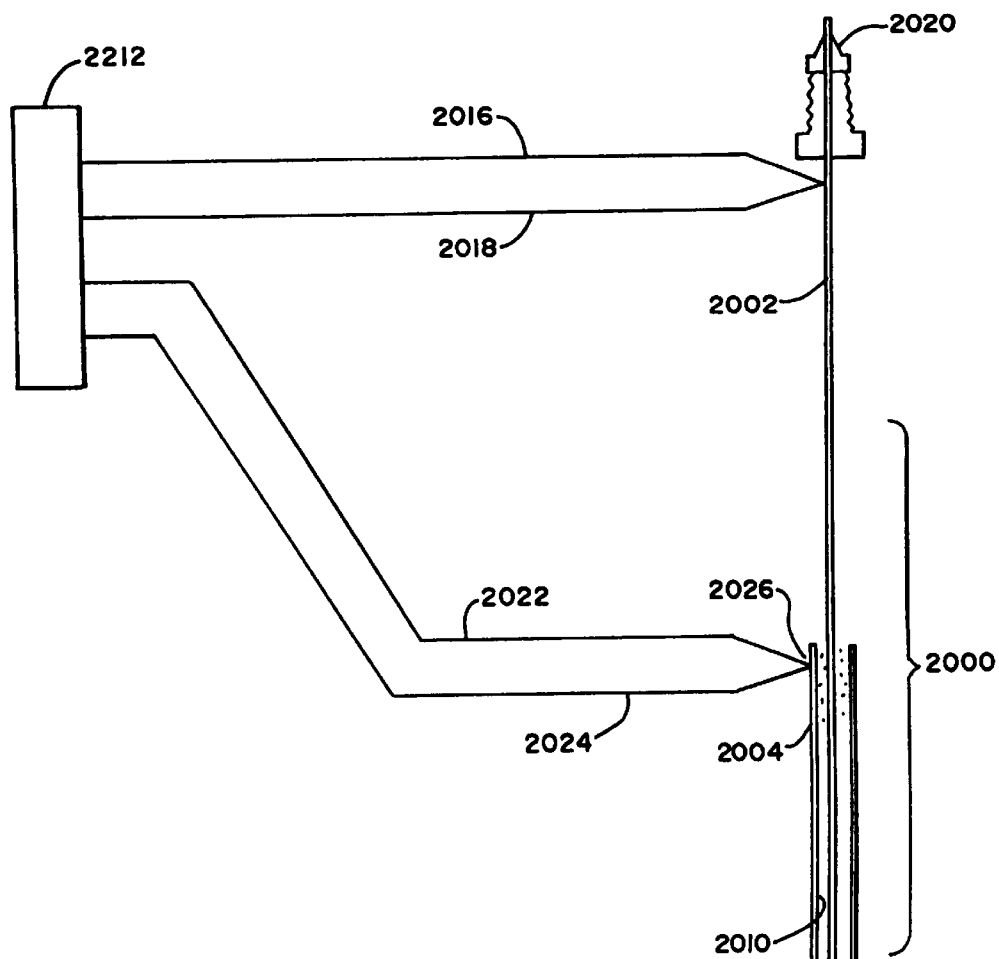
FIG. 27 is a schematic circuit diagram of a modification which may be made to previous embodiments.
Figure 28:
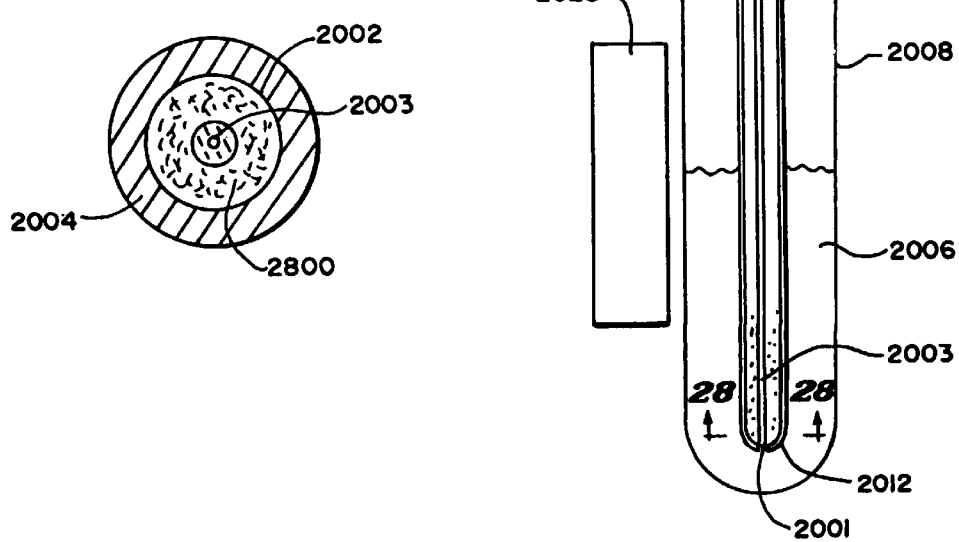
FIG. 28 is a sectional view taken through lines 28—28 of FIG. 27.

In FIG. 27, the restrictor is generally indicated as 2000. In this embodiment, the capillary tube is heated all of the way to its outlet end. The heating means depicted in FIGS. 24, 25, or 26 can be incorporated in the embodiment of FIG. 27 or any other embodiment in which heating extends substantially to the end of the capillary as well as embodiments in which the added heat or enthalpy in the fluid stream within the capillary or thermal conduction along the capillary, carries enough heat down to the outlet end to prevent extract deposition or ice formation within the capillary near its outlet end. In the preferred embodiment, the capillary is electrically heated along its length by passing a current through the capillary.

As shown in FIG. 27, the inner tube 2002 is a capillary tube having an internal diameter of 2 to 400 micrometers and an external diameter of 0.001 to 0.200 inch. The preferred embodiment incorporates an internal capillary tube with an inside diameter from 20 to 100 micrometers and an outside diameter smaller than the usual $\frac{1}{16}$ inch so that less current is required to heat it. Hereafter, the internal capillary tubing will be referred to as the capillary. The outer coaxial tube 2004 serves as the current return path for the resistance heating of the capillary, and as a barrier against the surrounding collection solvent 2006 in collecting tube 2008.

If necessary, the outer tube also provides rigidity for piercing a collecting trap vial septum. There is sufficient clearance between the outer diameter of capillary 2002 and the internal diameter of outer tube 2004 to allow for a coaxial insulating layer 2010. The insulating layer reduces heat flow from the heated capillary 2002 to the outer tube 2004 which is at a lower temperature. The insulating layer also prevents electrical conduction between the capillary and the outer tube. The insulation can be any suitable thermally insulating, heat resistant material such as woven fiberglass tubing or high temperature plastic tubing. A simple dead air space may also be sufficient insulation if spaced electrical insulating washers are incorporated to prevent short circuit.

Resistive heating of a restrictor tube without temperature control or insulation is described in Wright, et. al, in *Anal. Chem.* 59, pp. 38–44 (1987). However, in the subject invention the temperature of the capillary and of the flowing fluid within it is measured in the region where the fluid is in the heating zone. A coaxial thermal insulator allows the outlet end of capillary tube 1952 to be hot even though it is immersed in cold collection solvent.

Evacuation of the space between tubes further improves insulating performance but usually is not necessary. Glass fiber insulation 2800 (FIG. 28) between outer tube 2004 and inner capillary tube 2002 is usually satisfactory. At the outlet end of the restrictor, the capillary and outer steel tube are mechanically sealed and electrically connected at 2012 (FIGS. 24, 25, 26 and 27) to provide a current return path. This brazed connection also serves as a fluid barrier to prevent collection solvent from penetrating the insulating layer 2010. The connection can be made by tapering the outer tube down to the outer diameter of the capillary and welding the joint between tubes. The connection also can be constructed by an appropriate conventional soldering or brazing procedure.

A 304 stainless steel outer tube with a length of 8 inches, an outside diameter of 0.083 inch and an inside diameter of 0.063 inch is used. This provides a slender structure which is easily used with a variety of collection traps. If the tip of the outer tube is not intended to be tapered, such as for the purpose of piercing the septum of a septum vial, the connection may be made by bridging the gap with a brazed metal disc or with brazing material.

Wires 2016 and 2018 are electrically connected to the same point near the input end (fitting 2020) of the restrictor. Fitting 2020 is connected to the high pressure outlet of a supercritical extractor. Wires 2022 and 2024 are connected to the end 2026 of the outer tube 2004 which is electrically insulated from the capillary 2002. Wires 2016 and 2024 are used to pass current through the capillary providing resistance heating. Wires 2018 and 2022 are Kelvin voltage measurement leads which do not conduct the heating current. Wires 2018 and 2022 permit accurate measurement of the voltage along the capillary 2002 plus the voltage along the outer tube 2004 which is then used to measure and control the capillary temperature.

The electrical resistance of capillary tube 2002 is much greater than the resistance of outer tube 2004, so the voltage between the wires 2018 and 2022 give a good measurement of the voltage along capillary tube 2002. Fitting 2020 is connected to the fluid outlet of an extraction system such as an Isco model SFX-220. The outlet end of the restrictor is submerged in collection solvent 2006 when the extract is to be collected. Collection solvent 2006 is cooled by cooling element 2028 in contact with collecting tube 2008. Preferably, cooling element 2028 provides its cooling effect by evaporation of liquid carbon dioxide brought from a supply vessel not shown in the figure. Cooling the collection solvent 2006 improves the trapping efficiency of semi-volatile extracts. Pressurization of collecting tube 2008 in the manner shown for collecting tube 1976 in FIG. 25 is also recommended to increase the trapping efficiency.

The electrical connection at the capillary outlet end loses heat from the capillary in the outer region near the joint 2030 to the surrounding fluid since most good electrical conductors are also good thermal conductors. However, it is generally satisfactory to maintain restrictor temperatures in excess of +50° C. with simultaneous collection fluid temperatures below −50° C.; a temperature difference in excess of 100° C.

Alternate constructions reduce heat loss at the capillary outlet end by insulating it from the external tube and collection solvent. One such device combines the external tube and the insulating layer using a suitable thermally insulating material such as chemically resistant plastic. Plastics such as Teflon (a registered trademark of DuPont) and PEEK have acceptable properties. Such materials are electrical insulators.

In this case, the electrical current return and voltage-sensing connections to the capillary outlet end is made through electrical wires routed with the capillary through its external insulating tube and electrically insulated from the capillary. Similar separate wiring of the current return is shown schematically in FIG. 34. The electrical connection is made at a point near the capillary outlet end but inside the insulating layer tube and therefore thermally insulated from the solvent.

With this construction, only the small annular ring represented by the end of capillary tube is exposed to the cold solvent. If it is not necessary to heat the submerged portion of capillary, the outlet electrical return connection can be made at the point on the capillary somewhat above its lower end.

Prior heating methods with feedback control of capillary tube temperature apply heat to the exterior of the capillary tubing from an external heat source with the temperature of the heat source being controlled. This method generally incorporates a resistive heating element, a means to transfer heat from the heating element to the capillary exterior, a temperature sensor that measures the temperature of the external heat source and a feedback temperature controller. Using a suitable metal or metal-coated quartz capillary tube, the heating, heat transfer, and temperature sensing functions are incorporated into a single device wherein the actual temperature of the capillary tube is directly measured.

A small outside diameter metallic capillary has sufficient resistance to electric current flow such that it functions as the heating element which heats the extractant as it flows through the capillary. The temperature of the extractant fluid is controlled by controlling the current flow through the capillary. The performance of this directly heated capillary is superior because the extractant fluid is in direct contact with the heating element. The temperature sensing is also superior because the sensing element, the capillary tube itself, is in direct contact with the fluid whose temperature is being measured. Utilizing the linear resistance-temperature characteristic of the metal capillary tubing, the temperature of the capillary tubing is computed from its resistance. This capillary restrictor in conjunction with a computer or analog controller form a closed loop temperature control system which maintains a preset capillary temperature.

The restrictor temperature control can be obtained with an analog circuitry-based temperature controller but the temperature could be controlled equally as well by using a computer control system incorporating such features as division, subtraction, servo amplification and and the like. In either event, a computer element is used as a model for temperature setpoint control or programming because this is the simplest and clearest method to accomplish this function.

The electronics necessary to measure the capillary resistance include a means to apply an electric potential and a means to measure the current flow. Since the capillary is being heated by applying a potential difference or electric field, the same electric power means is used to heat the capillary and to measure its resistance. Rather than build a precise power amplifier to supply an accurate, known voltage, it is less expensive to use a less accurate power amplifier and measure the voltage applied as well as the resulting current flow. The current is measured by any conventional means such as voltage drop across a fixed resistor.

Figure 29:
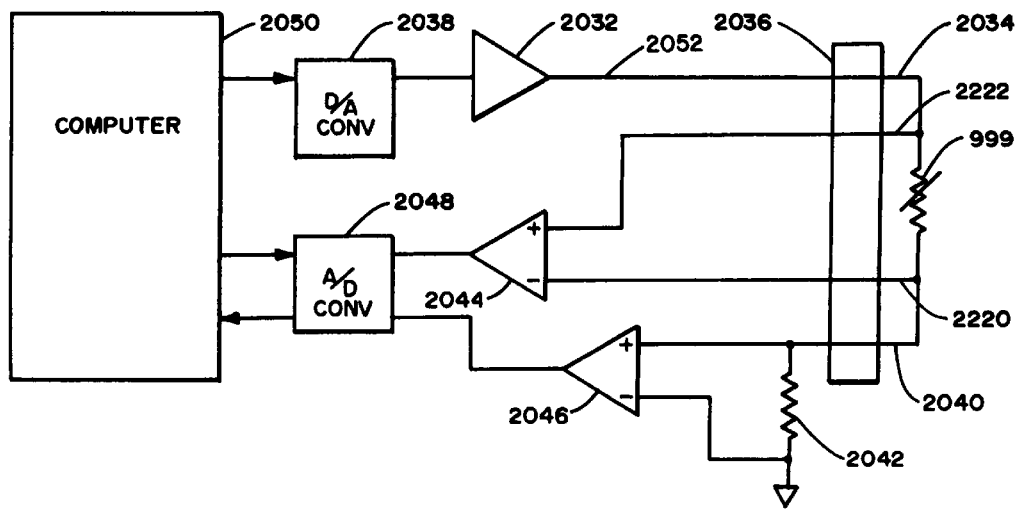
FIG. 29 is a schematic circuit diagram of an interface and computer control system useful in measuring and controlling the temperature of restrictors in accordance with the embodiments of FIGS. 1–29.

In FIG. 29 is a diagram of a general interface and computer control system 2051 which measures and controls the temperature of a metal capillary restrictor tube. One end of the capillary restrictor is connected to the power amplifier 2032 by wire 2034 through connector 2036. The computer drives the power amplifier 2032 through D/A converter 2038. The output current from power amplifier 2032 flows through wire 2034, through the electrical resistance provided by the circuit path through the capillary 999, wire 2040, and through current sensing resistor 2042 to the power return. The voltage across the capillary is amplified by differential amplifier 2044. The current through the capillary generates a proportional voltage across resistor 2042. The voltage proportional to current is amplified by differential amplifier 2046. The voltage and current signals are digitized by multiplexing A/D converter 2048. The computer 2050 measures the voltage across and current through the capillary. The resistance is then computed by division. The relationship to temperature is described by the equation 1. The temperature can then be calculated by equation 2.

The parameter $R_o$ is measured automatically by the interface and control system of FIG. 29 at a known temperature such as at ambient temperature before the restrictor is heated. This is done by the computer 2050 causing D/A 2038 and amplifier 2032 to provide a very small r.m.s voltage at lead 2052. This allows the resistance measurement to be made without heating the restrictor appreciably.

If a fast A/D converter circuit is used, the voltage and current measurements can be made during a voltage pulse having a duration which is short compared to the thermal response time of the capillary. In this $$R=R_o*(1+KT) \quad \text{Equation 1}$$

Where R=capillary resistance at temperature T
$R_o$=capillary resistance at 0° Centigrade
K=temperature constant for the capillary metal
(K is about 0.001 for type 304 stainless steel. For a maximum overall temperature range of 250° C., this reflects a 25% change in resistance.)

$$T=(R-R_o)/KR_o \quad \text{Equation 2}$$

$$R_o=R/(1+KT) \quad \text{Equation 3}$$

case, the signal to noise ratio of the measurements is improved by applying the full voltage available from power amplifier 2032. The heating energy is low because the voltage is applied for only a short time. After measuring the resistance R at any known temperature T, $R_o$ is calculated from equation 3.

When the outer tube is used as the current return path, it contributes to the total resistance. Since the outer tube may be at a different temperature than the capillary, its resistance is not necessarily related to the capillary temperature. For most applications, it is not necessary to compensate for the outer tube temperature. The outer tube is designed to have a much larger conducting cross-sectional area than the capillary. For this reason and because it is short, the outer tube resistance does not have a substantial effect on the overall resistance of the measured current path.

The closed-loop temperature control can be performed by several means which control the output of the power amplifier driving the capillary. The power amplifier is adjusted to maintain the capillary resistance at a constant value and therefore maintain a constant temperature. Three means of implementing the control of the capillary temperature will be presented:

1. Place a current sensing resistor in series with the capillary. Amplify the capillary current signal as sensed by this fixed resistor and the capillary voltage using separate gains which are opposite in polarity. The gains are chosen to balance the voltage signal with the current signal at the desired capillary resistance. An imbalance (difference) is amplified by the power amplifier to heat the capillary and maintain the desired resistance. Feedback is completed by amplifying a voltage corresponding to the error in capillary tube resistance.

2. Compute the capillary resistance as the ratio of measured voltage divided by measured current and use this value as the feedback in a closed loop control system which maintains the capillary resistance constant. In addition, the capillary resistance can be used to compute its temperature as described above. The computed capillary temperature is then used as the feedback signal in a closed loop temperature control circuit which accepts temperature as the control input and produces an electric output that both electrically heats the capillary and provides the measurement signals.

3. Place the capillary in one arm of a resistance voltage division circuit in series with a fixed resistor. Maintain the ratio of voltage across the capillary restrictor to the sum of voltages across the capillary and fixed resistor constant. This in effect maintains a constant resistance ratio and therefore, a constant capillary resistance. Feedback is completed by amplifying a voltage corresponding to the error of capillary tube resistance. The capillary resistance can be considered to be one of the four arms in a Wheatstone bridge.

Figure 30:
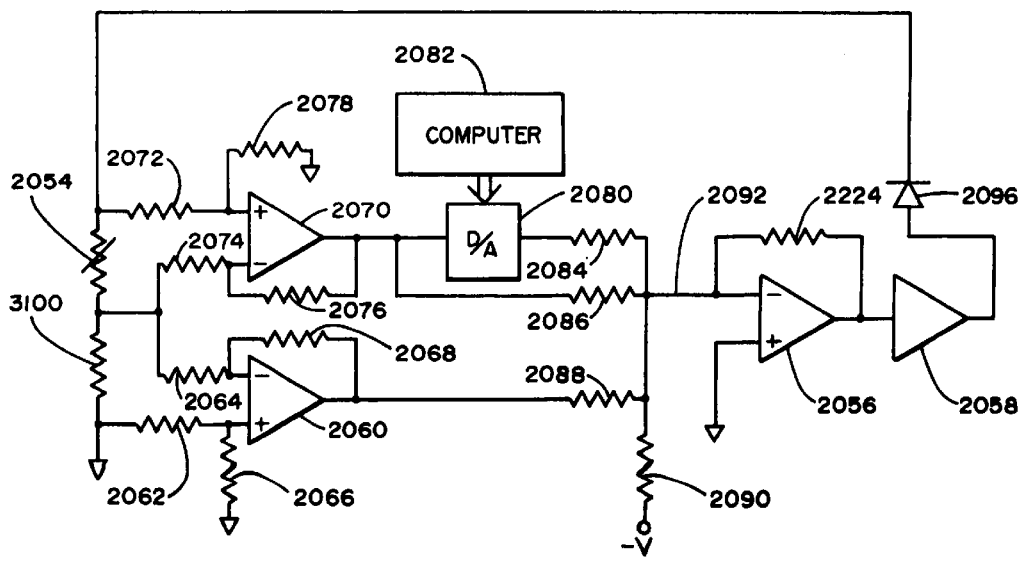
FIG. 30 is a schematic circuit diagram of a circuit useful in sensing the resistance and controlling the temperature of a restrictor in accordance with previous embodiments.

FIG. 30 is a schematic of a circuit that may be used to provide feedback control of the temperature of the capillary tube. This control method is similar to that described in U.S. Pat. No. 4,438,370 the disclosure of which is incorporated herein by reference.

With this circuit, the electrical power is applied to capillary 2054 by servo-amplifier 2058. Current through capillary 2054 is sensed by resistor 3100 and amplified by an inverting differential amplifier composed of amplifier 2060 and gain setting resistors 2062, 2064, 2066, and 2068 which produces a voltage proportional to the capillary current and opposite in polarity. The voltage across capillary 2054 is amplified by a non-inverting differential amplifier composed of amplifier 2070 and gain setting resistors 2072, 2074, 2076, and 2078. The output of amplifier 2070 is applied to the reference voltage input of digital to analog converter 2080.

Computer 2082, which controls converter 2080, selects the percentage of voltage at the output of amplifier 2070 to be applied to resistor 2084. The output of amplifier 2070 is also applied to resistor 2086. Resistors 2084, 2086, and 2088 connect to the summing node 2092 of amplifier 2056. Resistor 2086 and resistor 2084 with the D/A circuit inject a positive current into the summing node which is in variable proportion to the capillary voltage. Resistor 2088 draws an opposing current from the summing node which is proportional to the capillary current.

When these two currents are balanced, the output of amplifier 2056 is zero. The current gain and the voltage gain determine the ratio of capillary voltage to capillary current at which the summing currents will exactly offset each other. Resistor 2090 is connected to a negative voltage -V to turn on amplifiers 2056 and 2058 when the apparatus is turned on. This prevents the circuit from hanging up before heating starts.

This is expressed mathematically in equation 4.

These equations show that the null point can be shifted to a new ratio of voltage to current: a new temperature, by changing either gain $K_1$ or $K_2$. In practice, it is only necessary to change one gain as the desired capillary resistance change is about 25 percent. Therefore, this circuit is designed to change the voltage gain over a range which will adjust the voltage/current ratio by about 25 percent. Resistors 2084 and 2086 are chosen to set the fixed and variable gains to achieve this result. The variable portion of the voltage gain is set by multiplying D/A 2080 with the set point provided by computer 2082.

If the capillary temperature and therefore the capillary resistance is lower than the set point, the positive current into summing node 2092 decreases. In addition, if the output voltage from amplifier 2056 is constant, the current through the capillary increases due to the lowered load resistance. The increased current results in a larger current being drawn from summing node 2092 through resistor 2088. These two current shifts both act to shift the voltage at summing node 2094 below the non-inverting input of amplifier 2056. In response, the amplifier output voltage increases to balance the currents into and out of the summing node. The increased output voltage from amplifier 2056 drives servo-amplifier 2058 which heats capillary 2054, which will increase its resistance and restore the voltage/current ratio selected by the computer. Amplifier 2058 is designed to have a transfer $(K_1*V)-(K_2*I)=0$ or $V/I=K_2/K_1$=capillary resistance    Equation 4

Where V voltage across the capillary

I=current through the capillary $K_1$=voltage gain associated with amplifier 2070, D/A 2080 and resistors 2086 and 2084

$K_2$=current gain $$R = \frac{V}{I} = R_o * (1 + KT)$$    Equation 5

Where V=capillary voltage

I=current through capillary

R=capillary resistance at temperature T $R_o$=capillary resistance at 0° Centigrade K=temperature constant for the capillary metal (K is about 0.001 for type 304 stainless steel. For a maximum overall temperature range of 250° C., this reflects a 25% change in resistance.) function which provides stable control of the capillary temperature. A PID (Proportional-Integral-Derivative) transfer function of the type typically used in control systems is suitable. This closed-loop control system maintains the capillary resistance, and therefore temperature at a selected value. Diode 2096 prevents reverse current flow through the capillary tube 2054 if the temperature of the tube is higher than the set point value.

Figure 31:
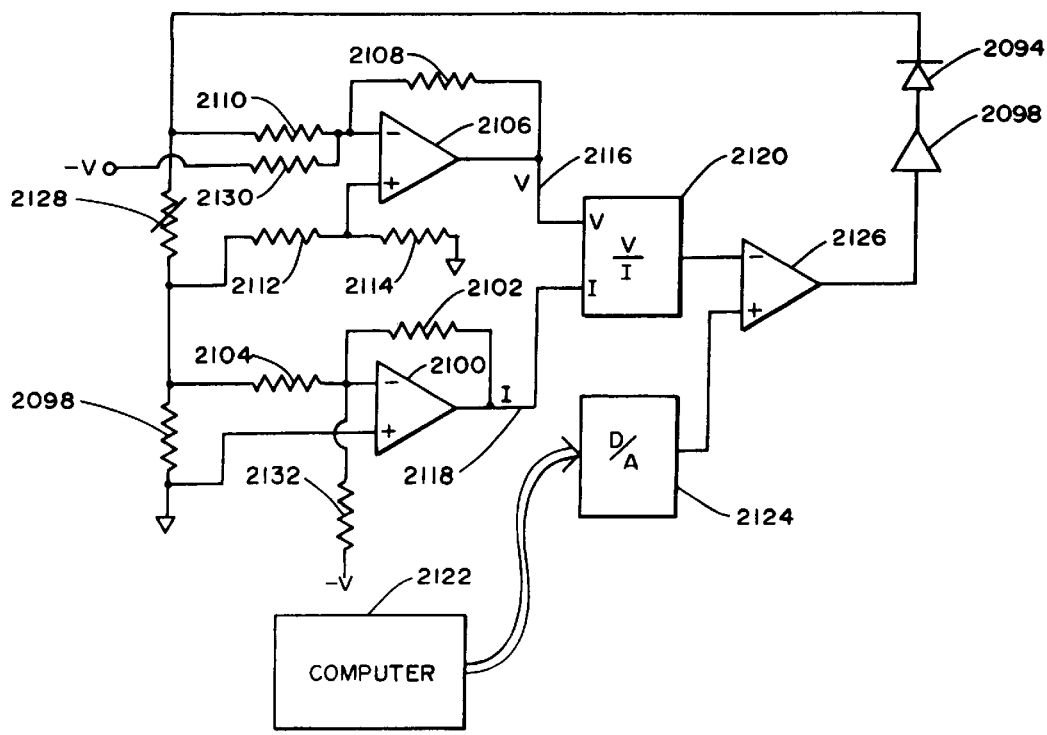
FIG. 31 is a schematic circuit diagram of a circuit that computes the electrical resistance of a restrictor for use in a temperature feedback loop control system.

FIG. 31 is a schematic circuit diagram of a circuit useful in calculating the resistance of the capillary tube for control purposes in accordance with the embodiments of FIGS. 24 to 28. The capillary current is sensed by resistor 2098 and scaled in magnitude by amplifier 2100 and gain-setting resistors 2102 and 2104. The capillary voltage is amplified by a differential amplifier consisting of amplifier 2106 and associated gain-setting resistors 2108, 2110, 2112, and 2114. The voltage signal conducted by wire 2116, and the current signal conducted by wire 2118 enter ratio circuit 2120 where a signal proportion al to the voltage divided by the current is generated. The relationship of resistance to temperature is described by equation 5.

Computer 2122 generates a digital resistance set point which is proportional to the desired capillary temperature. The resistance signal is converted to a voltage by digital to analog converter 2124. The resistance feedback signal from ratio circuit 2120 is subtracted from the resistance set point signal from D/A circuit 2124 by differential amplifier 2126 and this difference or resistance error signal is amplified by power amplifier 2098 to heat the capillary 2128.

The resistor 2130 is led from a negative potential to the inverting input of amplifier 2106 and resistor 2132 is similarly led to the inverting input of amplifier 2100 to insure turn-on of amplifier 2098 when the apparatus is turned on. This prevents the circuit from hanging up before the heating starts. The amplification transfer function is designed to heat the capillary when the resistance, and therefore the temperature, is too low. The transfer function of amplifier 2098 is of the usual proportional-integral-derivative (PID) type used in control systems. Diode 2094 illustrates that the control signal is unidirectional, or that it can only run current through the capillary in one direction. As the capillary heats, its resistance increases until the voltage/current ratio matches the set point from computer 2122. This control system functions as described to maintain a constant ratio of capillary voltage to capillary current and therefore a constant capillary resistance. The theory of operation is the same as given in explanation of FIG. 29, and the same equations apply. Elements such as the ratio computation, and other control computations can be performed by a computer if one is present in the system.

Figure 32:
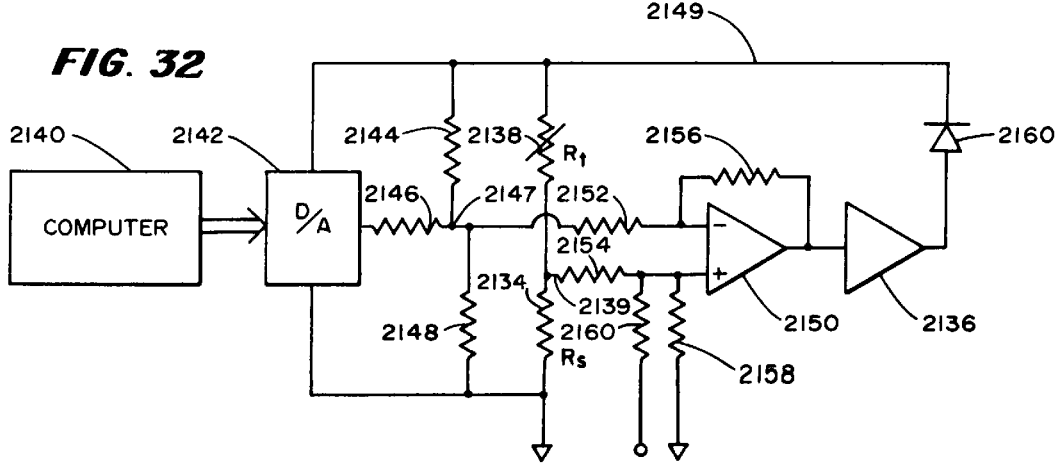
FIG. 32 is a schematic circuit diagram of the bridge circuit useful in the control system for the temperature of a restrictor.

FIG. 32 is a diagram of implementation number three. The capillary 2138 is connected in series with current sense resistor 2134. The voltage $V_2$ across resistor 2134 is equal to the output voltage of amplifier 2136 multiplied by the ratio of resistor 2134 ($R_s$ divided by the sum of resistor 2134 plus the capillary 2138 resistance ($R_t$) as shown in equation 6.

Set point voltage $V_1$ is generated by computer 2140 in conjunction with digital to analog converter 2142. The reference voltage for the D/A converter is the amplifier voltage V (2149) or a voltage proportional to V. In this way, the output of the D/A circuit is equal to the digital input multiplied by the amplifier output voltage V. The D/A output is shifted and scaled by a level shift circuit composed of resistors 2144, 2146, and 2148.

Since the capillary resistance change over a typical operating temperature change of 250° C. is only about 25 percent, it is preferable to shift the D/A output and compress the full scale set point voltage $V_1$ into the operating range of feedback signal $V_2$. The set point voltage $V_1$ is a percentage of servo amplifier output voltage V with the percentage determined by the output of computer 2140. The voltage $V_1$ is subtracted from $V_2$ and amplified by a difference amplifier composed of amplifier 2150 with resistors 2152, 2154, 2156, and 2158. The output current from servo-amplifier 2136 heats capillary 2138 so as to maintain the voltage $V_2$ at the set point voltage $V_1$. Resistor 2160 is lead to positive voltage $V_3$ to turn on amplifier 2150 and 2136 when the apparatus is turned on. This prevents the circuit from hanging up before heating starts. The amplified error signal is applied to capillary 2138 through diode 2160 to heat the capillary. As an example, suppose that the capillary 2138 temperature is lower than desired. The resulting resistance will be lower than the set point value. As a result, voltage $V_2$ will be larger than set point voltage $V_1$. Amplifier 2136 incorporates the usual PID transfer function and amplifies the derived difference or error signal and heats capillary 2138 to increase its resistance and restore the balance between $V_1$ and $V_2$.

As can be understood from the above description, the supercritical extraction technique has several $$V_2 = V*(R_s/(R_s+R_t)) \quad \text{Equation 6}$$

advantages, such as for example: (1) it automates the sample injection and fraction collection part of the extraction process as well as automating the extraction itself; (2) it allows the vials to be changed during the extraction process without depressurizing the extraction chamber; (3) it provides good trapping efficiency; (4) it provides low extract/solvent losses; (5) it provides reduced freezing and plugging of the restrictor; (6) it reduces icing up of the outside of the vial; (7) it permits the conditions of the extraction, such as temperature and pressure, to be changed such as to remove certain substances from the sample matrix and deposit each substance in a separate vial; (8) it is also useful for investigating extraction kinetics by changing the vial during the extraction for examination; (9) it permits the use of different size vials because the stroke of a lift is no longer tied to the extraction cartridge elevator; and (10) it permits the use of multiple wash stations to clean the outside of the restrictor.

Although a preferred embodiment of the invention has been described in some detail, many modifications and variations of the preferred embodiment can be made without deviating from the invention. Therefore, it is to be understood that within the scope of the appended claims the invention may be practiced other than as specifically described.

What is claimed is:

1. A method of supercritical fluid extracting, comprising the steps of:

extracting extract from a sample with an extractant;

adjusting the pressure in the extractor by adjusting a variable restrictor located at least partly within a collector; and expanding the extract and extractant in the collector while avoiding plugging the variable orifice restrictor, wherein the extract directly is collected therein.

2. A method according to claim 1 further including the step of heating at least a portion of the restrictor.

3. A method in accordance with claim 2 wherein the step of heating the restrictor includes the step of applying heat to the restrictor from an external energy source.

4. A method in accordance with claim 2 wherein the step of heating the restrictor includes the step of controlling the flow of heat with a feedback system that controls the application of heat to the restrictor.

5. A method in accordance with claim 1 wherein the step of adjusting the pressure in the extractor comprises the step of adjusting the pressure in the extractor by adjusting a variable restrictor located at least partly within a collector wherein an adjustment means that extends outside of the collector is used to adjust the variable restrictor.

* * * * *